US009764016B2

(12) United States Patent
Janse et al.

(10) Patent No.: US 9,764,016 B2
(45) Date of Patent: Sep. 19, 2017

(54) **GENETIC ATTENUATION OF *PLASMODIUM* BY B9 GENE DISRUPTION**

(71) Applicants: SANARIA INC., Rockville, MD (US); ACADEMISCH ZIEKENHUIS LEIDEN, ZA Leiden (NL); STICHTING KATHOLIEKE UNIVERSTEIT, GA Nijmegen (NL)

(72) Inventors: Chris J. Janse, Leiden (NL); Takeshi Annoura, Tokyo (JP); Shahid M. Khan, Leiden (NL); Ben Van Schaijk, Nijmegen (NL); Ivo H J Ploemen, Nijmegen (NL); Martijn W. Vos, Nijmegen (NL); Robert Sauerwein, Nijmegen (NL)

(*) Notice: Subject to any disclaimer, the term of this patent is extended or adjusted under 35 U.S.C. 154(b) by 55 days.

(21) Appl. No.: 14/434,859

(22) PCT Filed: Jan. 24, 2014

(86) PCT No.: PCT/US2014/013009
§ 371 (c)(1),
(2) Date: Apr. 10, 2015

(87) PCT Pub. No.: WO2014/116990
PCT Pub. Date: Jul. 31, 2014

(65) Prior Publication Data
US 2015/0313980 A1 Nov. 5, 2015

Related U.S. Application Data

(60) Provisional application No. 61/757,072, filed on Jan. 25, 2013, provisional application No. 61/783,326, filed on Mar. 14, 2013.

(51) Int. Cl.
*A61K 39/002* (2006.01)
*A61K 39/00* (2006.01)
*A61K 39/015* (2006.01)

(52) U.S. Cl.
CPC ...... *A61K 39/015* (2013.01); *A61K 2039/522* (2013.01); *A61K 2039/545* (2013.01)

(58) Field of Classification Search
CPC .............. A61K 39/522; A61K 39/5254; C12N 15/111; C12N 2510/00; C12N 2320/50
See application file for complete search history.

(56) References Cited

U.S. PATENT DOCUMENTS

| 4,850,305 A | 7/1989 | Georgi et al. |
| RE35,348 E | 10/1996 | Georgi |

(Continued)

FOREIGN PATENT DOCUMENTS

| CN | 1142887 A | 12/1995 |
| CN | 1213497 A | 10/1997 |

(Continued)

OTHER PUBLICATIONS

Agnandji, S.T., et al., "First results of phase 3 trial of RTS,S/AS01 malaria vaccine in African children," *New Engl J Med* 365(20):1863-1875, Massachusetts Medical Society, United States (2011).

(Continued)

*Primary Examiner* — Ja'Na Hines
(74) *Attorney, Agent, or Firm* — Sterne, Kessler, Goldstein & Fox P.L.L.C.

(57) ABSTRACT

Disclosed herein are mutant *Plasmodium*-species parasites that are genetically attenuated (GAP). They retain the ability to infect a host and invade host hepatocytes but subsequently their development is completely arrested within the liver stage of *Plasmodium* development and the parasites do not reach the blood stage of development. Vaccines and pharmaceutical compositions comprising genetically attenuated *Plasmodium* sporozoites as well as methods of using the same are likewise provided.

14 Claims, 21 Drawing Sheets
(1 of 21 Drawing Sheet(s) Filed in Color)

(56) References Cited

U.S. PATENT DOCUMENTS

| | | | |
|---|---|---|---|
| 5,766,597 | A | 6/1998 | Paoletti et al. |
| 5,983,557 | A | 11/1999 | Perich et al. |
| 7,122,179 | B2 | 10/2006 | Kappe et al. |
| 7,229,627 | B2 | 6/2007 | Hoffman et al. |
| 7,550,138 | B1 | 6/2009 | Waters et al. |
| 8,043,625 | B2 | 10/2011 | Sim et al. |
| 8,268,959 | B2 | 9/2012 | Golding et al. |
| 8,367,810 | B2 | 2/2013 | Sim et al. |
| 8,821,896 | B2 | 9/2014 | Sim et al. |
| 8,992,944 | B2 | 3/2015 | Sim et al. |
| 2005/0208078 | A1 | 9/2005 | Hoffman et al. |
| 2005/0220822 | A1 | 10/2005 | Hoffman et al. |
| 2005/0233435 | A1 | 10/2005 | Kappe et al. |
| 2007/0169209 | A1 | 7/2007 | Hoffman et al. |
| 2011/0033502 | A1* | 2/2011 | Kappe .................. A61K 39/015 424/272.1 |
| 2012/0156245 | A1 | 6/2012 | Hoffman et al. |
| 2012/0288525 | A1 | 11/2012 | Chakravarty et al. |
| 2012/0328645 | A1 | 12/2012 | Hoffman et al. |
| 2013/0224250 | A1 | 8/2013 | Sim et al. |

FOREIGN PATENT DOCUMENTS

| | | |
|---|---|---|
| GB | 1594721 A | 5/1978 |
| JP | 57156421 | 9/1982 |
| JP | 7-289119 | 7/1995 |
| WO | WO 91/16814 A1 | 11/1991 |
| WO | WO 92/11760 | 7/1992 |
| WO | WO 95/26633 | 7/1992 |
| WO | WO 00/74478 A1 | 12/2000 |
| WO | WO 03/087322 A2 | 10/2003 |
| WO | WO 2014/116990 A1 | 7/2014 |

OTHER PUBLICATIONS

Aly, A.S.I., et al., "Targeted deletion of SAP1 abolishes the expression of infectivity factors necessary for successful malaria parasite liver infection," *Molecular Microbiology* 69(1):152-163, Blackwell Publishing Ltd., England (2008).

Aly, A.S.I., et al., "SAP1 is a critical post-transcriptional regulator of infectivity in malaria parasite sporozoite stages," *Molecular Microbiology* 79(4):929-939, Blackwell Publishing Ltd., England (2011).

Annoura, T., et al., "Assessing the adequacy of attenuation of genetically modified malaria parasite vaccine candidates," *Vaccine* 30(16):2662-2670, Elsevier Ltd., England (2012).

Arredondo, S.A., et al., "Structure of the *Plasmodium* 6-cysteine s48/45 domain," *Proc Natl Acad Sci* 109(17):6692-6697, The National Academy of Sciences of the USA, United States (2012).

Carter, R., et al., "Predicted disulfide-bonded structures for three uniquely related proteins of *Plasmodium falciparum*, Pfs230, Pfs48/45 and Pf12," *Mol Biochem Parasitol* 71(2):203-210, Elsevier Science B.V., Netherlands (1995).

Clyde, D.F., et al., "Immunization of man against sporozite-induced falciparum malaria," *The American Journal of the Medical Sciences* 266(3):169-177, Charles B. Slack Inc., United States (1973).

Douradinha, B., et al., "Genetically attenuated P36p-deficient *Plasmodium berghei* sporozoites confer long-lasting and partial cross-species protection," *Int J Parasitol* 37(13):1511-1519, Elsevier Ltd., England (2007).

Ecker, A., et al., "Reverse genetics screen identifies six proteins important for malaria development in the mosquito," *Mol Microbiol* 70(1):209-220, Blackwell Publishing Ltd., England (2008).

Epstein, J.E., et al., "Live Attenuated Malaria Vaccine Designed to Protect Through Hepatic CD8+ T Cell Immunity," *Science* 334:475-480, American Association for the Advancement of Science, United States (2011).

Franke-Fayard, B., et al., "A *Plasmodium berghei* reference line that constitutively expresses GFP at a high level throughout the complete life cycle," *Mol Biochem Parasitol* 137(1):23-33, Elsevier B.V., Netherlands (2004).

Gerloff, D.L., et al., "Structural models for the protein family characterized by gamete surface protein Pfs230 of *Plasmodium falciparum*," *Proc Natl Acad Sci* 102(38):13598-13603, The National Academy of Sciences of the USA, United States (2005).

Guguen-Guillouzo, C., et al., "High yield preparation of isolated human adult hepatocytes by enzymatic perfusion of the liver," *Cell Biol Int Rep* 6(6):625-628, Academic Press Inc. (London) Ltd., England (1982).

Gwadz, R.W., et al., "Preliminary studies on vaccination of rhesus monkeys with irradiated sporozoites of *Plasmodium knowlesi* and characterization of surface antigens of these parasites," *Bull World Health Organ* 57(Suppl 1):165-173, World Health Organization, Switzerland (1979).

Helm, S., et al., "Identification and Characterization of a Liver Stage-Specific Promoter Region of the Malaria Parasite *Plasmodium*," *PLoS One* 5(10):e13653, 9 pages, Public Library of Science, United States (2010).

Hermsen, C.C., et al., "Detection of *Plasmodium falciparum* malaria parasites in vivo by real-time quantitative PCR," *Mol Biochem Parasitol* 118(2):247-251, Elsevier Science B.V., Netherlands (2001).

Hoffman, S.L., et al., "Protection of Humans against Malaria by Immunization with Radiation-Attenuated *Plasmodium falciparum* Sporozoites," *The Journal of Infectious Diseases* 185:1155-1164, Infectious Diseases Society of America, United States (2002).

Ifediba, T. and Vanderberg, J.P., "Complete in vitro maturation of *Plasmodium falciparum* gametocytes," *Nature* 294(5839):364-366, Macmillan Journals Ltd., England (1981).

Janse, C.J., et al., "High-efficiency transfection and drug selection of genetically transformed blood stages of the rodent malaria parasite *Plasmodium berghei*," *Nat Protoc* 1(1):346-356, Nature Publishing Group, England (2006).

Kooij, T.W.A., "Rodent Malaria Parasites: Genome Organization & Comparative Genomics," pp. 1-192, Thesis, Leiden University (2006).

Labaied, M., et al., "*Plasmodium yoelii* Sporozoites with Simultaneous Deletion of P52 and P36 are Completely Attenuated and Confer Sterile Immunity against Infection," *Infection and Immunity* 75(8):3758-3768, American Society for Microbiology, United States (2007).

Lin, J., et al., "A Novel 'Gene Insertion/Marker Out' (GIMO) Method for Transgene Expression and Gene Complementation in Rodent Malaria Parasites," *PLoS One* 6(12):e29289, 13 pages, Public Library of Science, United States (2011).

Lootens, L., et al., "The uPA(+/+)-SCID mouse with humanized liver as a model for in vivo metabolism of 4-androstene-3,17-dione," *Drug Metab Dispos* 37(12):2367-2374, The American Society for Pharmacology and Experimental Therapeutics, United States (2009).

Meuleman, P., et al., "A simple and rapid method to determine the zygosity of uPA-transgenic SCID mice," *Biochem Biophys Res Commun* 308(2):375-378, Elsevier Inc., United States (2003).

Meuleman, P., et al., "Morphological and biochemical characterization of a human liver in a uPA-SCID mouse chimera," *Hepatology* 41(4):847-856, American Association for the Study of Liver Diseases, United States (2005).

Mota, M.M., et al., "Migration of *Plasmodium* sporozoites through cells before infection," *Science* 291(5501):141-144, American Association for the Advancement of Science, United States (2001).

Nussenzweig, R.S., et al., "Protective Immunity produced by the Injection of X-irradiated Sporozoites of *Plasmodium berghei*," *Nature* 216:160-162, Macmillan (Journals), Ltd., England (1967).

Orito, Y., et al., "Liver-specific protein 2: a Plasmodium protein exported to the hepatocyte cytoplasm and required for merozoite formation," *Mol Microbiol* 87(1):66-79, Blackwell Publishing Ltd., England (2012).

Ploemen, I.H.J., et al., "Visualisation and Quantitative Analysis of the Rodent Malaria Liver Stage by Real Time Imaging," *PLoS One* 4(11):e7881, 12 pages, Public Library of Science, United States (2009).

Ploemen, I.H.J., et al., "*Plasmodium berghei* Δp52&p36 parasites develop independent of a parasitophorous vacuole membrane in

(56) References Cited

OTHER PUBLICATIONS

Huh-7 liver cells," *PLoS One* 7(12):e50772, 5 pages, Public Library of Science, United States (2012).
Ploemen, I., "Development and Demise of *Plasmodium* Liver Stage Parasites: The Hunt for a Genetically Attenuated Malaria Vaccine," pp. 1-209, Thesis, Radboud Universiteit Nijmegen (Jun. 2013).
Ponnudurai, T., et al., "Chloroquine sensitivity of isolates of *Plasmodium falciparum* adapted to in vitro culture," *Trop Geogr Med* 33(1):50-54, Foundation Tropical and Geographical Medicine, Netherlands (1981).
Ponnudurai, T., et al., "Cultivation of fertile *Plasmodium falciparum* gametocytes in semi-automated systems. 1. Static cultures," *Trans R Soc Trop Med Hyg* 76(6):812-818, Royal Society of Tropical Medicine and Hygiene, England (1982).
Ponnudurai, T., et al., "Infectivity of cultured *Plasmodium falciparum* gametocytes to mosquitoes," *Parasitology* 98(Pt 2):165-173, Cambridge University Press, England (1989).
Purcell, L.A., et al., "Chemical Attenuation of *Plasmodium berghei* Sporozoites Induces Sterile Immunity in Mice," *Infection and Immunity* 76(3):1193-1199, American Society for Microbiology, United States (2008).
Rénia, L., et al., "A malaria heat-shock-like determinant expressed on the infected hepatocyte surface is the target of antibody-dependent cell-mediated cytotoxic mechanisms by nonparenchymal liver cells," *Eur J Immunol* 20(7):1445-1449, VCH Verlagsgesellschaft mbH, Germany (1990).
Rieckmann, K.H., et al., "Sporozoite Induced Immunity in Man Against an Ethiopian Strain of *Plasmodium falciparum*," *Transactions of the Royal Society of Tropical Medicine and Hygiene* 68:258-259, Royal Society of Tropical Medicine and Hygiene, England (1974).
Roestenberg, M., et al., "Long-term protection against malaria after experimental sporozoite inoculation: an open-label follow-up study," *The Lancet* S0140-6736(11):60360-60367, Lancet Publishing Group, England (2011).
Seder, R.A., et al., "Protection Against Malaria by Intravenous Immunization with a Nonreplicating Sporozoite Vaccine," *Science* 341:1359-1365, American Association for the Advancement of Science, United States (Sep. 2013).
Silvie, O., et al., "A sporozoite asparagine-rich protein controls initiation of *Plasmodium* liver stage development," *PLoS Pathog* 4(6):e1000086, 12 pages, Public Library of Science, United States (2008).
Spring, M., et al., "First-in-human evaluation of genetically attenuated *Plasmodium falciparum* sporozoites administered by bite of Anopheles mosquitoes to adult volunteers," *Vaccine* 31(43):4975-4983, Elsevier Ltd., England (Sep. 2013).
Stewart, M.J. and Vanderberg, J.P., "Malaria sporozoites leave behind trails of circumsporozoite protein during gliding motility," *J Protozool* 35(3):389-393, Society of Protozoologists, United States (1988).
Sturm, A., et al., "Manipulation of host hepatocytes by the malaria parasite for delivery into liver sinusoids," *Science* 313(5791):1287-1290, American Association for the Advancement of Science, United States (2006).
Thompson, J., et al., "Comparative genomics in *Plasmodium*: a tool for the identification of genes and functional analysis," *Mol Biochem Parasitol* 118(2):147-154, Elsevier Science B.V., Netherlands (2001).
Tonkin, M.L., et al., "Structural and biochemical characterization of *Plasmodium falciparum* 12 (*Pf*12) reveals a unique interdomain organization and the potential for an antiparallel arrangement with *Pf*41," *J Biol Chem* 288(18):12805-12817, American Society for Biochemistry and Molecular Biology, United States (May 2013).
Vanbuskirk, K.M., et al., "Preerythrocytic, live-attenuated *Plasmodium falciparum* vaccine candidates by design," *Proc Natl Acad Sci* 106(31):13004-13009, The National Academy of Sciences of the USA, United States (2009).
Van Dijk, M.R., et al., "Genetically attenuated, P36p-deficient malarial sporozoites induce protective immunity and apoptosis of infected liver cells," *Proc Natl Acad Sci* 102(34):12194-12199, The National Academy of Sciences of the USA, United States (2005).
Van Schaijk, B.C.L., et al., "Gene Disruption of *Plasmodium falciparum* p52 Results in Attenuation of Malaria Liver Stage Development in Cultured Primary Human Hepatocytes," *PLoS One* 3(10):e3549, 10 pages, Public Library of Science, United States (2008).
Van Schaijk, B.C.L., et al., "Removal of Heterologous Sequences from *Plasmodium falciparum* Mutants Using FLPe-Recombinase," *PLoS One* 5(11):e15121, 8 pages, Public Library of Science, United States (2010).
Watarai, H., et al., "Methods for detection, isolation and culture of mouse and human invariant NKT cells," *Nat Protoc* 3(1):70-78, Nature Publishing Group, England (2008).
International Searching Authority, International Search Report for International Patent Application No. PCT/US2014/013009, United States Patent Office, Alexandria, Virginia, mailed Apr. 16, 2014, 5 pages.
Janse, C.J., et al., "High efficiency transfection of *Plasmodium berghei* facilitates novel selection procedures," *Molecular & Biochemical Parasitology* 145:60-70, Elsevier B.V., Netherlands (2005).
International Bureau, International Preliminary Report on Patentability and Written Opinion for International Application No. PCT/US2014/013009, Geneva, Switzerland, mailed Aug. 6, 2015, 11 pages.
Alonso, PL et al., Efficacy of the RTS,S AS02A vaccine against *Plasmodium falciparum* infection and disease in young African childen: randomized controlled trial. *Lancet* 364:1411-1420 (2004).
Beier, J.C., "Malaria Parasite Development in Mosquitoes," *Annu. Rev. Entomol.* 43:519-43 (1998).
Belnoue, E., et al., "Protective T Cell Immunity Against Malaria Liver Stage After Vaccination with Live Sporozoites Under Chloroquine Treatment," *The Journal of Immunology* 172:2487-2495, The American Association of Immunologists, United States (2004).
Breman, J.G., et al., "Defining and defeating the intolerable burden of malaria III. Progress and perspectives," *Am. J Trop. Med. Hyg.* 77(Suppl 6):vi-xi, The American Society of Tropical Medicine and Hygiene, United States (2007).
Chattopadhyay et al., "The Effects of radiation on the safety and protective efficacy of an attenuated *Plasmodium yoelii* sporozoite malaria vaccine," *Vaccine* 27:3675-3680 (Jun. 2009).
Clyde, D.F., "Immunity to falciparum and vivax malaria induced by irradiated sporozoites: a review of the University of Maryland studies, 1971-75," *Bulletin of the World Health Organization* 68 (*Suppl.*):9-12, World Health Organization, Switzerland (1990).
Daubenberger, C.A., "First clinical trial of purified, irradiated malaria sporozoites in humans," *Expert Rev. Vaccines* 11(1):31-33, Expert Reviews Ltd, England (2012).
Doolan, D.L., and Hoffman, S.L., "The Complexity of Protective Immunity Against Liver-Stage Malaria," *The Journal of Immunology* 165:1453-1462, The American Association of Immunologists, United States (2000).
Edelman, R., et al., "Long-Term Persistence of Sterile Immunity in a Volunteer Immunized with XIrradiated *Plasmodium falciparum* Sporozoites," *The Journal of Infectious Diseases* 168:1066-1070, Infectious Diseases Society of America, United States (1993).
Editorial. "Malaria, 2010: more ambition and accountability please," *The Lancet* 375:1407, Lancet Publishing Group, England (Apr. 2010).
Engelmann, S., et al., "Transgenic *Plasmodium berghei* sporozoites Expressing β-galactosidase for Quantification of Sporozoite Transmission," *Mol Biochem Parasitol.* 146(1): 30-37, Elsevier, Netherlands (2006).
Epstein, J.E. et al., "Malaria vaccines: are we getting closer?" *Curr. Opin. Mol. Ther.* 9(1):12-24 (2007).
Herrington, D.A., et al., "Safety and immunogenicity in man of a synthetic peptide malaria vaccine against *Plasmodium falciparum* sporozoites," *Nature* 328:257-259, Nature Publishing Group, England (1987).
Herrington, D., et al., "Successful Immunization of Humans With Irradiated Malaria Sporozoites: Humoral and Cellular Responses of

(56) References Cited

OTHER PUBLICATIONS the Protected Individuals," *Am. J. Trop. Med. Hyg.* 45(5):539-547, The American Society of Tropical Medicine and Hygiene, United States (1991).

Hoffman, S.L., et al., "Sporozite Vaccine Induces Genetically Restricted T Cell Elimination of Malaria from Hepatocytes," *Science* 244:1078-1081, American Association for the Advancement of Science, United States (1989).

Hoffman, S.L., et al., "Development of a metabolically active, non-replicating sporozoite vaccine to prevent *Plasmodium falciparum* malaria," *Human Vaccines* 6:97-106, Landes Bioscience, United States (Jan. 2010).

Jiang, J-B., et al., "Induction of retarded exoerythrocytic schizonts by chloroquanide resulting in delayed parasitaemia of *Plasmodium inui* in *Macaca mulatta*," *Acta Pharmacologica. Sinica* 11(3):272-274, Shanghai Institute of Materia Medica (1990).

Kramer, L.D., and Vanderberg, J.P., "Intramuscular Immunization of Mice With Irradiated *Plasmodium berghei* Sporozoites," *The American Journal of Tropical Medicine and Hygiene* 24(6):913-916, The American Society of Tropical Medicine and Hygiene, United States (1975).

Krzych, U., et al., "T Lymphocytes from Volunteers Immunized with Irradiated *Plasmodium falciparum* Sporozoites Recognize Liver and Blood Stage Malaria Antigens," *J. Immunol.* 155:4072-4077, American Association of Immunologists, United States (1995).

Long, C.A., and Hoffman, S.L., "Malaria-from Infants to Genomics to Vaccines,"*Science* 297:345-347, American Association for the Advancement of Science, United States (Jul. 2002).

Luke, T.C., and Hoffman, S.L., "Rationale and plans for developing a non-replicating, metabolically active, radiation-attenuated *Plasmodium falciparum* sporozoite vaccine," *The Journal of Experimental Biology* 206:3803-3808, The Company of Biologists Ltd, England (2003).

Mattig, F.R., et al., "A simple method for the purification of *Eimeria tenella* sporozoites," *Appl. Parasitol.* 34:139-142, Gustav Fischer Verlag Jena, Germany (1993).

Ménard, R., "Knockout malaria vaccine?" *Nature* 433:113-114, Nature Publishing Group, England (2005).

Mueller, A-K. et al., "Genetically modified *Plasmodium* parasites as a protective experimental malaria vaccine," *Nature* 433:164-167, Nature Publishing Group, England (2005).

Mueller, A-K et al., "Plasmodium liver stage developmental arrest by depletion of a protein at the parasite-host interface," *Proc Natl Acad Sci U S A.* 102(8):3022-3027, The National Academy of Sciences, United States (2005).

Nussenzweig, R., "Use of Radiation-attenuated Sporozoites in the Immunoprophylaxis of Malaria," *International Journal of Nuclear Medicine and Biology* 7:89-96, Pergamon Press Ltd, England (1980).

Ockenhouse, C.F., et al., "Phase I/IIa Safety, Immunogenicity, and Efficacy Trial of NYVAC-Pf7, a Pox-Vectored, Multiantigen, Multistage Vaccine Candidate for *Plasmodium falciparum* Malaria," *The Journal of Infectious Diseases* 177:1664-1673, The University of Chicago, United States (1998).

Plowe, C.V., et al., "The Potential role of vaccines in the elimination of falciparum malaria and the eventual eradication of malaria," *J. Infect. Dis.* 200:1646-1649, Oxford University Press, United States (Dec. 2009).

Pombo, D.J., et al., "Immunity to malaria after administration of ultra-low doses of red cells infected with *Plasmodium falciparum*," *The Lancet* 360(9333):610-617, Lancet Publishing Group, England (2002).

Purcell et al., "Chemically attenuated *Plasmodium* sporozoites induce specific immune responses, sterile immunity, and cross-protection against heterologous challenge," *Vaccine* 26(38): 4880-4884, National Institutes of Health, United States (2008).

Rénia, L. et al, "Vaccination against malaria with live parasites ," *Expert Rev. Vaccines* 5:473-481, Future Drugs Ltd, United Kingdom (2006).

Rénia L., "Protective immunity against malaria liver stage after vaccination with live parasites," *Parasite* 15(3):379-383 (2008).

Richie, T.L., and Saul, A., "Progress and challenges for malaria vaccines," *Nature* 415:694-701, Macmillan Magazines Ltd, England (2002).

Rieckmann, K.H., "Human immunization with attenuated sporozoites," *Bulletin of the World Health Organization* 68 (*Suppl.*):13-16, World Health Organization, Switzerland (1990).

Roestenberg, M.D., "Protection against Malaria Challenge by Sporozoite Inoculation," *New England Journal of Medicine* 361(5):468-476, Massachusetts Medical Society, United States (Jul. 2009).

Sedegah et al.,"Cross-protection between attenuated *Plasmodium berghei* and *P. yoelii* sporozoites," *Parasite Immunology* 29:559-565, Blackwell Publishing Ltd, United States (2007).

Spitalny, G.L. and Nussenzweig, R.S., "Effect of Various Routes of Immunization and Methods of Parasite Attenuation on the Development of Protection Against Sporozoite-Induced Rodent Malaria," *Proceedings of the Helminthological Society* 39 (*Special Issue*):506-514, United States (1972).

Trager,W. and Jenen, J.B., "Continuous Culture of *Plasmodium Falciparum*: its Impact on Malaria Research," *International Journal for Parasitology* 27(9):989-1006, Elsevier Science Ltd., Great Britain (1997).

Warburg, A. and Miller, L.H., "Sporogonic Development of a Malaria Parasite in Vitro," *Science* 255(5043):448-450, American Association for the Advancement of Science, United States (1992).

Warburg, A. and Schneider, I., "In vitro culture of the mosquito stage of *Plasmodium falciparum*," *Experimental Parasitology* 76(2):121-126, Academic Press, Inc, United States (1993).

Waters, A.P., et al., "Malaria Vaccines: Back to the Future?," *Science* 307:528-530, AAAS, United States (2005).

Wood, D.E., et al., "The Use of Membrane Screen Filters in the Isolation of *Plasmodium berghei* Sporozoites from Mosquitos," *Bulletin of the World Health Organization* 57(*Suppl. 1*):69-74 (1979).

Wykes, M. and Good M.F., "A case for whole-parasite malaria vaccines ," *Int. J. Parasitol.* 37:705-712, Academic Press, Inc., United States (2007).

International Searching Authority, International Search Report and Written Opinion in Int'l Patent Application No. PCT/US2010/20564, Alexandria, Virginia, mailed Mar. 9, 2010, 12 pages.

European Patent Office, Supplementary European Search Report and Opinion for EP Appl. No. 10731974.1, Munich, Germany, mailed on Aug. 14, 2012, 7 pages.

Arevalo-Herrera, M. and Herrera, S., "*Plasmodium vivax* malaria vaccine development," *Molecular Immunology* 38(6):443-455, Elsevier Science Ltd., England (2001).

Bojang, K.A., et al., "Efficacy of RTS,S/AS02 malaria vaccine against *Plasmodium falciparum* infection in semi-immune adult men in The Gambia: a randomised trial," *Lancet* 358(9297):1927-1934, Elsevier, England (2001).

Clyde, DF et al., "Specificity of Protection of Man Immunized Against Sporozoite-Induced Falciparum Malaria," *Am. J Med. Sci.* 266:398-401, Lippincott Williams & Wilkins, United States (1973).

Collins, W.E., et al., "Adaptation of a strain of *Plasmodium vivax* from Mauritania to New World monkeys and Anopheline Mosquitoes," *J. Parasitol.* 84:619-621, American Society of Parasitologists, United States (Jun. 1998).

Collins, W.E., et al., "Potential of the Panama strain of *Plasmodium vivax* for the testing of malarial vaccines in *Aotus nancymai* monkeys," Am. J. Trop. Med. Hyg. 67:454-458, American Society for Tropical Medicine and Hygiene, United States (Nov. 2002).

Egan JE, et al., "Humoral immune responses in volunteers immunized with irradiated *Plasmodium falciparum* sporozoites," *J Trop Med and Hygiene* 49:166-173, American Society for Tropical Medicine and Hygiene, United States (1993).

Food and Drug Administration, "Guidance for Industry, Content and Format of Chemistry, Manufacturing and Controls Information and Establishment Description Information for a Vaccine or Related Product," fda.gov, accessed at http://www.fda.gov/cber/guidelines.htm, accessed on Sep. 24, 2015 (1999).

(56) References Cited

OTHER PUBLICATIONS

Garfield, R.M. and Vermund, S.H., "Changes in Malaria Incidence After Mass Drug Administration in Nicaragua," *The Lancet* 322:500-503, Elsevier, England (1983).

Gerberg, E.J., "Manual for Mosquito Rearing and Experimental Techniques," American Mosquito Control Association, Inc., Bulletin No. 5 (Jan. 1979).

Grady et al., "Program and Abstracts of the 41st Annual Meeting of the American Society of Tropical Medicine and Hygiene," Supplement to *The American Journal of Tropical Medicine and Hygiene* 47(4):218, American Society for Tropical Medicine and Hygiene, United States (1992), Abstract only.

Hamilton, D.R., et al., "An Integrated System for Production of Gnotobiotic *Anopheles quadrimaculatus*," *Journal of Invertebrate Pathology* 30:318-324, Academic Press, New York and London (1977).

Hurd, H. et al., "In vitro methods for culturing vertebrate and mosquito stages of *Plasmodium*," *Microbes and Infection* 5:321-327, Editions scientifiques et medicales Elsevier SAS, France (2003).

Hurtado, S., et al. "Regular production of infective sporozoites of *Plasmodium falciparum* and *P. vivax* in laboratory-bred *Anopheles albimanus*," *Anals Trop. Med. & Parasit.* 91:49-60, Liverpool School of Tropical Medicine, England (1997).

Kester, K.E., et al., "Efficacy of recombinant circumsporozoite protein vaccine regimens against experimental *Pasmodium falciparum* malaria," *J. Infect. Dis.* 183:640-647, Oxford University Press, United States (2001).

Li, X., et al., "Design of potent CD1d-binding NKT cell ligand as a vaccine adjuvant," *PNAS* 107(29):13010-13015, National Academy of Sciences, United States (2010).

Lin, K., et al., "In Vivo Protection Provided by a Synthetic New Alpha-Galactosyl Ceramide Analog against Bacterial and Viral Infections in Murine Models," *Antimicrobial Agents and Chemotherapy* 54(10):4129-4136, American Society for Microbiology, United States (2010).

Malik, A., et al., "Human cytotoxic T lymphocytes against the *Plasmodium falciparum* circumsporozoite protein." *Proc. Natl. Acad. Sci.* 88:3300-3304, National Academy of the Sciences, United States (1991).

Miller, L.H. and Hoffman, S.L., "Research toward vaccines against malaria,"*Nature Medicine Vaccine Supplement*, 4(5):520-524, Nature America Inc., United States (1998).

Munderloh, U.G, et al., "*Anopheles stephensi* and *Toxorhynchites amboinensis*: aseptic rearing of mosquito larvae on cultured cells," *J Parasit.* 68(6):1085-1091 (1982).

Munderloh, U.G, et al., "Malarial Parasites Complete Sporogony in Axenic Mosquitoes," *Experientia* 41:1205-1207, Birkhäuser Verlag AG (Sep. 1985).

Okiro, E.A., et al., "The decline in paediatric malaria admissions on the coast of Kenya," *Malaria Journal* 6(151):1-11, BioMed Central, UK (2007).

Padte, N.N., et al., "Clinical development of novel CD1d-binding NKT cell ligand as a vaccine adjuvant," *Clinical Immunology* 140:142-151, Elsevier Ltd., United States (2011).

Roestenberg, M.D., et al., "Protection against Malaria Challenge by Sporozoite Inoculation," *New England Journal of Medicine* 361(5):468-476, Massachusetts Medical Society, United States (Jul. 2009).

Rosales-Ronquillo, M.C., et al., "Aspetic Rearing of *Anopheles stephensi*," *Annals of the Entomological Society of America.* 66:949-954, Entomological Society of America (Sep. 1973).

Schofield, L., et al., "Synthetic GPI as a candidate anti-toxic vaccine in a model of malaria," *Nature* 418:785-789, Nature Publishing Group (Aug. 2002).

Schuster, F.L., "Cultivation of *Plasmodium* spp.," *Clinical Microbiology Reviews* 15(3):355-364, American Society for Microbiology, United States (2002).

Smith, D.L., et al., "Revisiting the Basic Reproductive Number for Malaria and Its Implications for Malaria Control," *PLoS Biology* 5:0531-0542, Public Library of Science, United States (2007).

Stoute, J.A., et al., "Long term efficacy and immune responses following immunization with the RTS,S malaria vaccine," *J. Infect. Dis.* 178:1139-1144 (1998).

Tsuji, M., et al., "Progress toward a Malaria Vaccine: Efficient Induction of Protective Anti-Malaria Immunity," *Biol. Chem.* 382(4):553-570, Walter de Gruyter, Berlin and New York (2001).

Vanderberg, J.P., "Development of Infectivity by the *Plasmodium berghei* Sporozoite," *The Journal of Parasitology* 61(1):43-50, The American Society of Parasitologists (1975).

Wu, Y., et al., "Phase 1 Trial of Malaria Transmission Blocking Vaccine Candidates Pfs25 and Pvs25 Formulated with Montanide ISA 51," *PLoS Biology* 3:1-9, Public Library of Science, United States (2008).

Zapata, J.C., et al., "Reproducible infection of intact *Aotus lemurinus griseimembra* monkeys by *Plasmodium falciparum* sporozoite inoculation," *J. Paristol.* 88:723-729, American Society of Parasitologists, United States (Aug. 2002).

Esp@cenet Database, English language abstract of CN1142887A, published Dec. 18, 1995 (listed as document FP6 on the accompanying form PTO/SB/08A).

Esp@cenet Database, English language abstract of CN1213497A, published Oct. 8, 1997 (listed as document FP7 on the accompanying form PTO/SB/08A).

Moser, G., et al., "Sporozoites of Rodent and Simian Malaria, Purified by Anion Exchangers, Retain their Immunogenicity and Infectivity," *J. Protozool.* 25(1):119-124, Society of Protozoologists, United States (1978).

U.S. Appl. No. 14/671,003, Sim, B. Kim Lee, et al., filed Mar. 27, 2015 (Not Published).

Notice of Allowance mailed Sep. 18, 2015 in U.S. Appl. No. 14/671,003, Sim, B. Kim Lee, et al., filed Mar. 27, 2015 (Not Published).

Annoura, T., et al., "Two Plasmodium 6-Cys family-related proteins have distinct and critical roles in liver-stage development," *The FASEB Journal* 28:2158-2170, The Federation, United States (2014).

Van Dijk, M.R., et al., "Three Members of the 6-cys Protein Family of Plasmodium Play a Role in Gamete Fertility," *PLoS Pathogens* 6(4):e1000853, 14 pages, Public Library of Science, United States (2010).

Van Schaijk, B.C.L., et al., "A genetically attenuated malaria vaccine candidate based on *P. falciparum* b9/slarp gene-deficient sporozoites," *eLife* 3:e03582, 18 pages, eLife Sciences Publications, Ltd., England (2014).

\* cited by examiner

A

B

| P. berghei Acc # | motif 1 OxOxC | motif 2 C[F,S,T] | motif 3 [F,I,L]xCxC | signal sequence | Name |
|---|---|---|---|---|---|
| PBANKA_011100 | VSHC | CF | IYCYC | MVQIKKNILJYTHLSYLVYTHKGLEHQCDFNENHTIEJTDTENHDIDN (SEQ ID NO: 104) | P12 |
| PBANKA_011110 | FTFIC | CF | FECSC | MMSIYFWVAIHIFSSFWMIQNIEICDFSRGSLDVALMNNKILIDNNLK (SEQ ID NO: 51) | P12p |
| PBANKA_030600 | VVIIC | CF | FECHC | MGKKKILFYFFTYGIFILILINYEYANNLVKKFQKKDGENIKRNEEP (SEQ ID NO: 52) | P230p |
| PBANKA_030610 | FKIYC | CF | FQCSC | MRKPLIVYLFFSYFFLYIFAKKNDINYGDIGIEQPYCSFMFLEKNIL (SEQ ID NO: 53) | P230 |
| PBANKA_080810 | VAYNC | CF | FRCIC | MSESKKYKWNPVRCLVCWIMLYLILWTNFLDGLNKFNPIKEEGYLYL (SEQ ID NO: 54) | B9 |
| PBANKA_081940 | AIGSC | CS | IMCFC | MEHHAIVLLELIKLIYCNHNEYISYDKTYEYLVDISKNNNRLICVE (SEQ ID NO: 55) | conserved *Plasmodium* protein, unknown function |
| PBANKA_100210 | LFYMC | CS | IVCIC | MKQYEFARHINTYFSVAQNMLFSIFLYYAFSLLIFLSIFVFKMRKALY (SEQ ID NO: 56) | P36 |
| PBANKA_100220 | FMYYC | CF | FICLC | MMKRRIFMYYCFCFLLKYVAFSNVTNPNTTLGHFEICKINIYSGDAE (SEQ ID NO: 57) | p52(p36p) |
| PBANKA_100260 | ITYIC | CF | FYCFC | MKGLLIYTFPFLLKQLSVRSEEYVCDFRAKNYLYDNKDILYCTTNAKP (SEQ ID NO: 58) | P41 |
| PBANKA_100300 | MFLHC | CS | ISCYC | MKDHIKNVCFRKTLLISLLJILKYTKYDYLEKENDEKQKYNSNISSP (SEQ ID NO: 59) | Seq |
| PBANKA_110760 | IVILC | CF | FSCYC | MSKMIHVKNITSILVIVILCLNGITSKKSVDLANLVKNITLNASPG (SEQ ID NO: 60) | P38 |
| PBANKA_111340 | VIIYC | CT | FICKC | MPRLSIFGTLFLWSIFLIIKTNCFYFKVDSELISKDSNIRKCHKEHYL (SEQ ID NO: 61) | PSOP12 |
| PBANKA_120070 | AGGFC | CS | LGCIC | METFFFLLTIMYLLFATRVVNVKAQSEGIIKTKSHEISYDENSRHLYI (SEQ ID NO: 62) | conserved *Plasmodium* protein, unknown function |
| PBANKA_121810 | VLIVC | CS | IACKC | MYVINIYYVLIVCLIGTVLSSPYWGBPLLNDFGNEELNTPKKEKRLHST (SEQ ID NO: 63) | Oocyst capsule protein (Cap380) |
| PBANKA_135960 | LGYKC | CS | FYCIC | MLYFFGNSRFLFFYFFYFVLVIKSSVGKNEYVSPDELNIKTSGFL (SEQ ID NO: 64) | P48/45 |
| PBANKA_135970 | IALVC | CF | IYCRC | MKGFFTGASHVFYLIKGYLSYIIFPNGYVCDFKFNPLVNVLPSINTTG (SEQ ID NO: 65) | P47 |

GENETIC ATTENUATION OF *PLASMODIUM* BY B9 GENE DISRUPTION

CROSS-REFERENCE TO RELATED APPLICATIONS

The present application is the U.S. National Stage of International Application No. PCT/US2014/013009, filed Jan. 24, 2014, which claims priority to U.S. Provisional Patent Application No. 61/757,072, filed Jan. 25, 2013, and U.S. Provisional Patent Application No. 61/783,326, filed Mar. 14, 2013, each of which is incorporated herein by reference in its entirety.

REFERENCE TO A SEQUENCE LISTING

The instant application contains a Sequence Listing, which has been submitted in ASCII format via EFS-Web and is hereby incorporated by reference in its entirety. Said ASCII copy, created on Mar. 31, 2015, is named "2602_0110002_SequenceListing" and is 26,625 bytes in size.

BACKGROUND OF THE INVENTION

Field of the Invention

This invention relates generally to malaria and the study of *Plasmodium* parasites. More particularly it relates to *Plasmodium* parasites genetically attenuated by gene disruption.

Background Art

Over 40 percent of the world's population is at risk for exposure to malaria. More than 250,000 new clinical malaria cases occur annually resulting in 800,000 to 1.2 million deaths most of which are children in sub-Saharan Africa suffering from a severe *P. falciparum* infection [1]. Malaria remains a global health crisis and there is a dire need for a highly effective malaria vaccine.

Recent results from the clinical trials of a malaria vaccine using a single recombinant protein as immunogen, RTS,S subunit vaccine with AS01 adjuvant; have shown modest protection. [2]. Although these results are potentially useful to reduce the global health burden of malaria, a whole sporozoite vaccine approach would provide a broader immunogenic spectrum and should be much more potent in conferring protection, thereby forming the next generation of malaria vaccines. Vaccination with live sporozoites is safe when parasite development is halted prior to the pathogenic post-hepatic blood stage. For this end, attenuation of sporozoites to affect pre-pathogenic liver-stage arrest of parasite development can be accomplished with radiation attenuated sporozoites (RAS) [47], genetically attenuated parasites (GAP) [36], and chemically attenuated sporozoites (CAS) [48]. RAS immunization has a long standing track record of proven efficacy in rodents [3], monkeys [4] and man [5, 6, 7, 47]. Indeed, in a recent clinical trial such a vaccine (Sanaria® PfSPZ Vaccine) protected 6 out of 6 human volunteers at the highest dose level and was completely safe [49]. In rodent models, the protective efficacies conferred by most GAP vaccines are similar to RAS. PfΔp52Δp36 is the only GAP vaccine that has been assessed in humans, but the trial in which the GAP Pf sporozoites were administered by mosquito bite had to be terminated because of breakthrough infections in one volunteer during immunization [50]. Both RAS and GAP vaccination strategies rely on the one hand on complete developmental arrest of the attenuated parasite at the liver stage of development in host hepatocytes in order to prevent breakthrough blood infection and the subsequent signs, symptoms and pathology of malaria, and on the other hand, the requisite immune responses that result in protection.

From a product manufacturing perspective there are advantages of a GAP vaccine approach. It is comprised of a parasite population with a homogeneous attenuation etiology. The genetic attenuation is an irreversible, intrinsic characteristic of the parasite and its attenuation is not dependent upon external (e.g. radiation, host drug metabolism) factors. Furthermore, in the GAP manufacturing process operators are never exposed to a Pf parasite that can cause disease. GAPs go into developmental arrest in the hepatocyte at the time point predestined by the specific gene deletion. Most GAPs that have been examined, like Δp52, Δp36, Δuis3, Δuis4 and Δslarp/Δsap1, arrest at early liver stage. Other GAPs, like Δfabb/f arrest in the late liver stage. Despite this apparent abundance of GAP vaccine candidates, it has proved to be very difficult to generate a safe and protective GAP in *Plasmodium* species of human host range, e.g., *P. falciparum*. For instance, unequivocal orthologs of the uis3 and uis4 genes in *P. berghei* and *P. yoelii* are absent in the *P. falciparum* genome (www.PlasmoDB.org) and can therefore not be made into a vaccine product. Breakthrough infection has also been a problem. In the *P. berghei* model liver stage arrest of the Δp52 [13], the Δp52&p36 and the Δfabb/f [14] parasites was not complete in that these mutants were capable of maturing in the liver in low numbers, resulting in a blood stage infection and malaria pathology in mice. Moreover, very low numbers of replicating Δp52&p36 *P. falciparum* parasites were observed in primary human hepatocyte cultures [14], and a breakthrough infection was observed in a clinical trial of Δp52&p36 *P. falciparum* parasites [50].

Thus, there remains a need for new *Plasmodium* GAP candidates that completely arrest in the liver stage (safety) and with which immunization confers an immune response and long-lasting protection (efficacy). Such a GAP candidate is the focus of this application.

SUMMARY OF THE INVENTION

Disclosed herein are *Plasmodium*-species parasitic organisms that are genetically attenuated by disruption of a first gene that governs a process required for successful liver stage development (e.g., b9, which is normally transcribed and translationally repressed during the sporozoite stage of development, and translationally expressed in the developmental early liver stage of the *Plasmodium* life cycle); and in an embodiment, the additional disruption of at least one other second gene that governs an independent but critical process for successful liver-stage development in the wild type from which the mutant is derived, such that upon infection of the host, the double deletion parasites can infect a subject, invade the host hepatocytes of the subject, but subsequently their development is completely arrested within hepatocytes and the parasite does not reach the blood stage of development.

In an embodiment, the first gene is b9, the gene product of which is B9; lisp2, the gene product of which is sequestrin (LISP2); p52, the gene product of which is P52; or p36, the gene product of which is P36.

In an embodiment, the *Plasmodium* species is a *Plasmodium* of human host range, e.g., *P. falciparum, P. vivax, P. ovale, P. malariae*, or *P. knowlesi*. In a further embodiment, the species is *P. falciparum*.

In an embodiment, the second gene is slarp, lisp1, lisp2, lsa2, lsa3, or any combination thereof.

In an embodiment, genetically attenuated organisms disclosed herein are suitable for clinical, pharmaceutical use in humans as an immunogen in a malaria vaccine for generating an immune response and protecting subjects against contracting malaria. The immunogens comprise aseptically prepared, purified, live, attenuated Plasmodium-species sporozoite-stage parasites of human host range, genetically attenuated by disruption of a first gene, e.g., b9 gene, function and a second gene function such that the sporozoite-stage parasites can infect the subject and invade host hepatocytes but the subsequent development of the Plasmodium organism is arrested at the liver stage within hepatocytes and does not reach the blood stage of development.

In an embodiment, methods of protection from P. falciparum-caused malaria are disclosed. The methods comprise the administration prophylactic malaria vaccine to a subject, e.g., administration of a regimen disclosed herein. The vaccine comprises aseptically prepared, purified, live, attenuated, sporozoite-stage Plasmodium parasites of human host range as immunogen, and the parasites are genetically attenuated by disruption of a first gene, e.g., b9 gene function and a second gene function, such that the sporozoite-stage of the parasites can infect a human subject and invade host hepatocytes but the subsequent development of the Plasmodium organism is arrested at the liver stage within hepatocytes and does not reach the blood stage of development. After administration of vaccine the subject generates an immune response to the parasite, and in a further embodiment, is protected from the pathogenic effects of P. falciparum infection when subsequently challenged.

DESCRIPTION OF THE DRAWINGS

The patent or application file contains at least one drawing executed in color. Copies of this patent or patent application publication with color drawing(s) will be provided by the Office upon request and payment of the necessary fee.

falciparum wt (cytochalasin D treated (cytoD) and untreated), PfΔslarp-b, PfΔslarpΔb9-F7 and PfΔslarpΔb9-G9 parasites. Gliding motility was quantified by determining the percentage of parasites that exhibited gliding motility by producing characteristic CSP trails (≥1 circles) or parasites that did not produce CSP trails (0 circles). (B) Cell traversal ability of *P. falciparum* NF54 and PfΔslarp-b and PfΔslarpΔb9-F7 sporozoites as determined by FACS counting of Dextran positive Huh-7 cells. Shown is the percentage of FITC positive cells. Dextran control (control): hepatocytes cultured in the presence of Dextran but without the addition of sporozoites. (C) In vitro invasion of *P. falciparum* wt, PfΔslarp-b, PfΔslarpΔb9-F7 and PfΔslarpΔb9-G9 sporozoites in primary human hepatocytes. Invasion is represented as the ratio of extra- and intracellular sporozoites by double staining at 3 and 24 hours post infection, determined after 3 wash steps to remove sporozoites in suspension.

Figure 6:
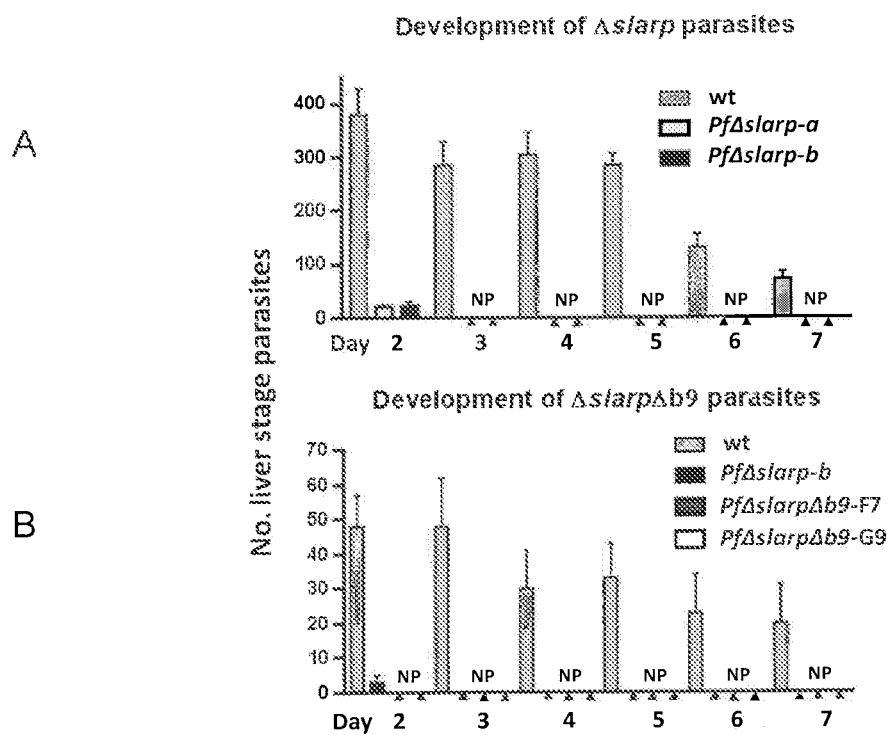

FIG. 6A-B: Development of *P. falciparum* wt, PfΔslarp-a PfΔslarp-b (A, top panel), PfΔslarpΔb9-F7 and PfΔslarpΔb9-G9 (B, bottom panel) liver-stages in primary human hepatocytes. From day 2 to 7 the number of parasites per 96-well was determined by counting parasites stained with anti-*P. falciparum* HSP70 antibodies. The B, bottom panel represents experiments performed in primary human hepatocytes from 2 different donors. No parasites present (NP).

Figure 7:
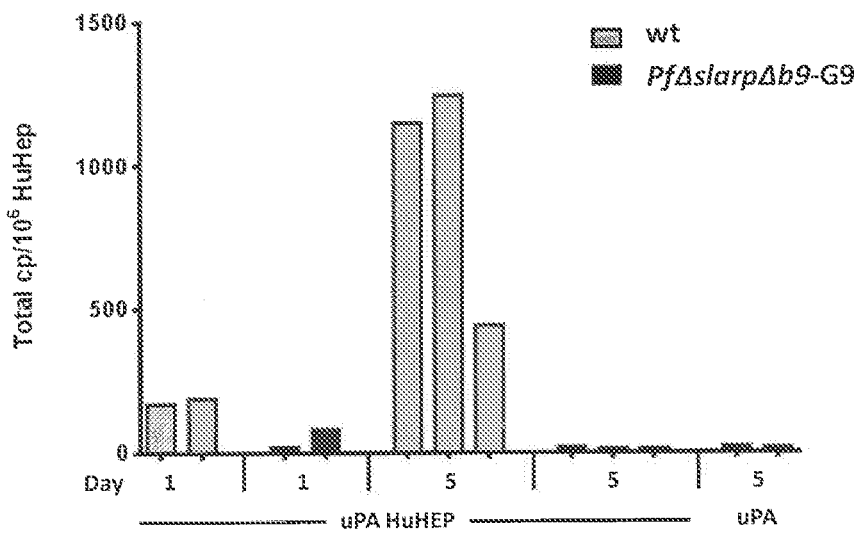

FIG. 7A-B: Development of liver stages of PfΔslarp Δb9 GAP in chimeric mice engrafted with human liver tissue. Mice were infected with $10^6$ wt or PfΔslarpΔb9-G9 sporozoites by intravenous inoculation. At 24 hours or at 5 days after sporozoite infection, livers were collected from the mice and the presence of parasites determined by qRT-PCR of the parasite-specific 18S ribosomal RNA. uPA HuHEP; Chimeric uPA Mice engrafted with human hepatocyte tissue. As controls, uPA mice; not engrafted with human hepatocytes. qRT-PCR results are shown by (A) graph and (B) table.

FIG. 8A-D: Generation and genotype analyses of *P. berghei* mutant; Δb9-a and Δb9-b, (A) Generation of mutant Δb9-a (1309cl1). For Δb9-a, the DNA-construct pL1439 was generated containing the positive/negative selectable marker cassette hdhfr/yfcy. This construct was subsequently used to generate the mutant Δb9-a (1309cl1) in the cl15cy1 reference line. See Table 4 for the sequence of the primers. (B) For the mutant Δb9-b (1481cl4) the pL1499 construct was generated which was used for the generation of the mutant in the PbGFP-Luc Con reference line. See Table 4 for the sequence of the primers. (C and D) Diagnostic PCR (C) and Southern analysis (D) of Pulse Field Gel (PFG)-separated chromosomes of mutant Δb9-a and Δb9-b confirming correct disruption of the b9-locus. See Table 4 for the sequence of the primers used for the selectable marker gene (M); 5'-integration event (5'); 3'-integration event (3') and the b9-ORF. Mutant Δb9-a has been generated in the reference *P. berghei* ANKA line cl15cy1. Mutant Δb9-b has been generated in the reference *P. berghei* ANKA line PbGFP-Luc which has a gfp-luciferase gene integrated into the silent 230p locus (PBANKA_030600) on chromosome (i.e., RMgm-29; http://pberghei.eu/index.php?rmgm=29). For Southern analysis, PFG-separated chromosome were hybridized using a 3'UTR phdhfr probe that recognizes the construct integrated into *P. berghei* b9 locus on chromosome 8, the endogenous locus of dhfr/ts on chromosome 7 and in mutant Δb9-b the gfp-luciferase gene integrated into chromosome FIG. 9: Characterization of the PVM in developing *P. berghei* Δb9 mutants. IFA of wild type and Δb9 infected hepatocytes stained with anti-HSP70 or anti-MSP1 (red) and anti-EXP1 and anti-UIS4 (green)-antibodies at various time points post infection. Nuclei are stained with Hoechst-33342. Bar represents 10 μm.

Figure 10:
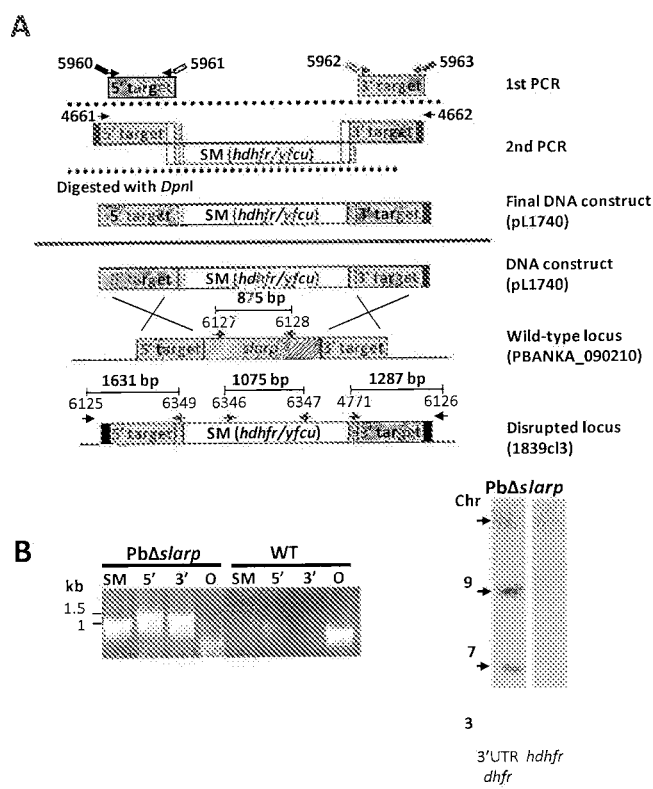

FIG. 10A-B: Generation and genotype analyses of *P. berghei* mutant; Δslarp-a. Generation of mutant Δslarp-a (1839cl3) mutant. For Δslarp-a the DNA-construct pL1740 was generated containing the positive/negative selectable marker cassette hdhfr/yfcy. This construct was subsequently used to generate the mutant Δslarp-a (1839cl3) in the PbGFP-Luc reference line. See Table 4 for the sequence of the primers. (B) Diagnostic PCR and southern analysis of Pulse Field Gel (PFG)-separated chromosomes of mutant Δslarp-a confirming correct disruption of the slarp-locus. See Table 4 for the sequence of the primers used for the selectable marker gene (SM); 5'-integration event (5'); 3'-integration event (3') and the slarp ORF. Mutant Δslarp has been generated in the reference *P. berghei* ANKA line PbGFP-Luc con which has a gfp-luciferase gene integrated into the silent 230p locus (PBANKA_030600) on chromosome 3 (i.e., RMgm-29; http://pberghei.eu/index.php?rmgm=29). For Southern analysis, PFG-separated chromosomes were hybridized using a 3'UTR pbdhfr probe that recognizes the construct integrated into *P. berghei* slarp locus on chromosome 9, the endogenous locus of dhfr/ts on chromosome 7 and the gfp-luciferase gene integrated into chromosome 3. In addition, the chromosomes were hybridized with the hdhfr probe recognizing the integrated construct into the slarp locus on chromosome 9.

Figure 11:
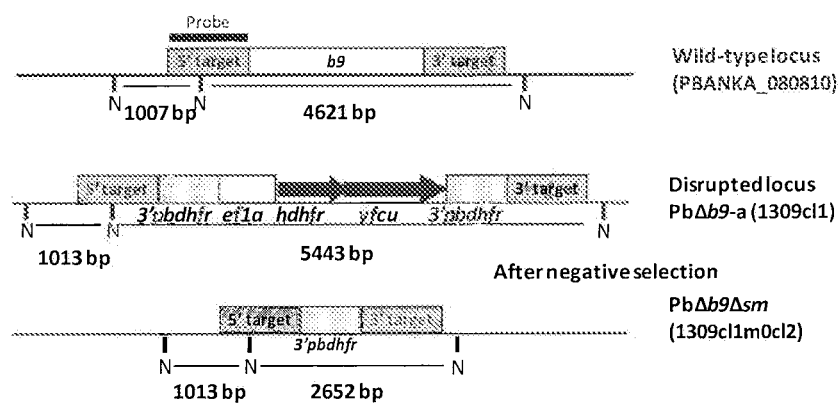
Figure 11:
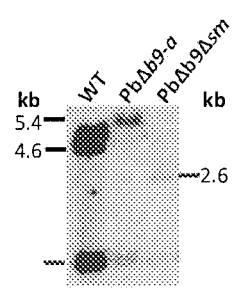

FIG. 11A-B: Generation and genotype analyses of *P. berghei* mutant; Δb9Δsm. (A) Schematic representation of the generation of a selectable marker free Δb9 mutant using the marker-recycling method. The b9 disruption construct containing the hdhfr::yfcu selectable marker (black arrows) flanked by the recombination sequences (3'pbdhfr, shaded boxes) targets the 230p locus by double cross-over homologous recombination at specific target regions (gray boxes). The Δb9-a mutant is obtained after transfection, using positive selection with pyrimethamine and then cloning. Subsequently, the marker-free Δb9(Δsm) mutant is selected by negative selection using 5-FC. Only mutant parasites that have 'spontaneously' lost the hdhfr::yfcu marker from their genome, achieved by a homologous recombination/excision, survive the negative selection. (B) Southern blot analysis was hybridized with a 5' UTR b9 probe (i.e., 5' targeting region). The localization of the restriction enzyme site (N; Nde I) and the expected size of the fragments are shown in Wt (wild type); Δb9-a (b9 deletion mutant) and Δb9Δsm (b9 deletion mutant free of selectable-marker).

Figure 12:
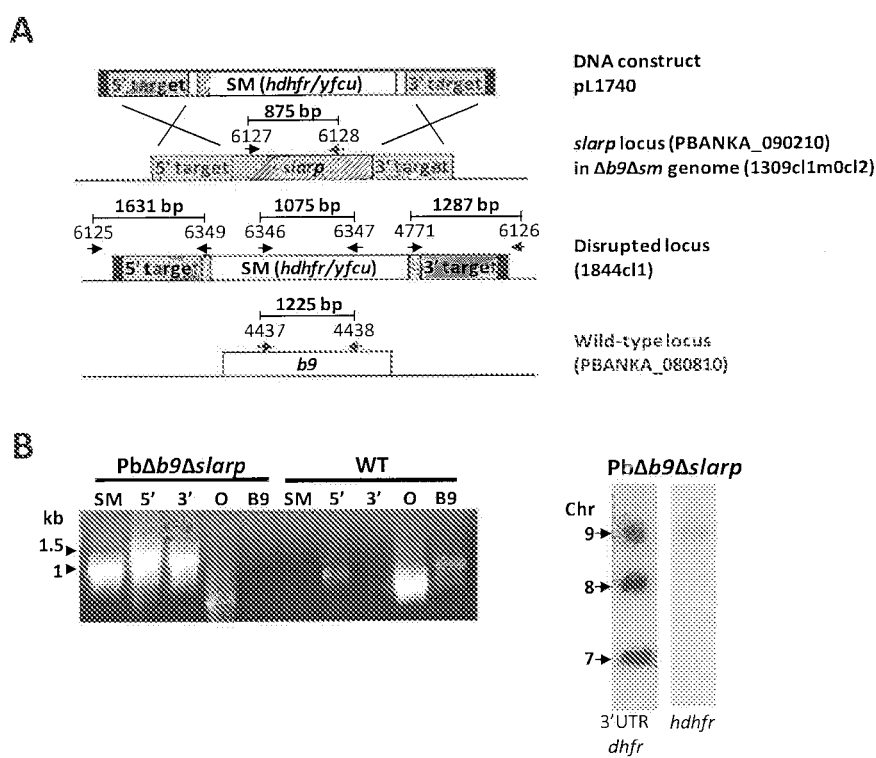

FIG. 12A-B: Generation and genotype analyses of *P. berghei* mutant; Δb9Δslarp. (A) A diagram showing the strategy for generation of mutant Δb9Δslarp. For Δb9Δslarp the DNA-construct pL1740 was generated containing the positive/negative selectable marker cassette hdhfr/yfcy. This construct was subsequently used to generate the mutant Δb9Δslarp in the Δb9Δsm mutant. See Table 4 for the sequence of the primers. (B) Diagnostic PCR and southern analysis of Pulse Field Gel (PFG)-separated chromosomes of mutant Δb9Δslarp confirming correct disruption of the slarp-locus and the b9 locus. See Table 4 for the sequence of the primers used for the selectable marker gene (SM); 5'-integration event (5'); 3'-integration event (3') and the slarp and the b9 ORF. For Southern analysis, PFG-separated chromosomes were hybridized using a 3'UTR pbdhfr probe that recognizes the construct integrated into *P. berghei* slarp locus on chromosome 9, the endogenous locus of dhfr/ts on chromosome 7 and a 3'UTR pbdhfr probe that recognizes the construct integrated into *P. berghei* b9 locus on chromosome 8. In addition, the chromosomes were hybridized with the hdhfr probe recognizing the integrated construct into the slarp locus on chromosome 9.

Figure 13:
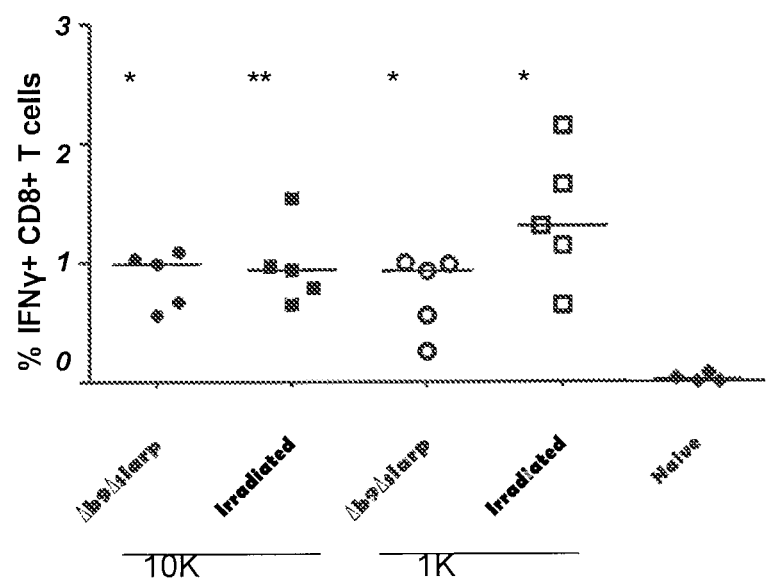

FIG. 13: Liver CD8+ T cells with IFNγ response after immunization with Δb9Δslarp or γ-irradiated sporozoites. Sporozoite specific CD8+ T cell response in the liver of naïve or immunized C57BL/6j mice at C+70 post a Δb9Δslarp or irradiated sporozoites immunization with a 10K/10K/10K or a 1K/1K/1K dose regimen. Intracellular IFNγ production was measured by flow cytometry before challenge in liver. Immunized groups and naive mice responded equally to a polyclonal (PMA/Ionomycine) stimulation (data not shown). *P<0.02; **P<0.001 compared to naïve mice.

Figure 14:
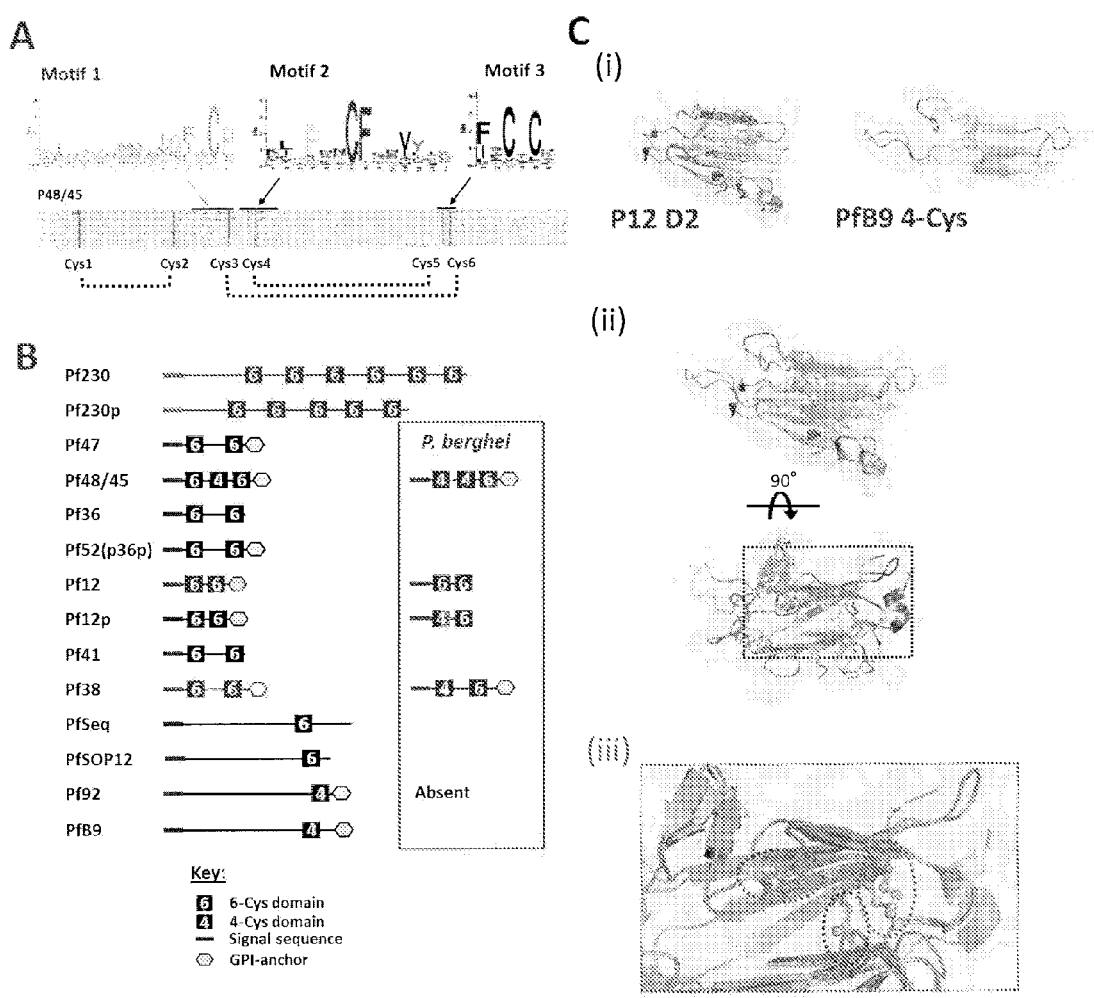

FIG. 14A-C(i)-(iii): Characterization and identification of 6-cysteine and 4-cysteine domains of the 6-Cys family of *Plasmodium* proteins. (A) ClustalW protein sequence alignment of a 6-cysteine domain of P48/45 of *P. berghei, P. yoelli, P. falciparum, P. vivax* and *P. knowlesi* as a type-example of the 6-Cys domain. The domain and the distribution of the conserved cysteines are shown that are predicted to form 3 pairs of internal disulfide bonds (Cys1&2; Cys3&5; Cys4&6). The location of three conserved motifs within the domain (black lines) is shown that were identified by a MEME analysis of 56 6-cysteine domains; these motifs encompass four of the six conserved cysteines. The letters within the MEME motifs refer to the single amino acids code and the relative height of each letter is proportional to the frequency of the amino acid(s) at that position. The 3 di-sulphide bonds within the 6-Cys domain are shown and indicated by dotted lines. (B) Schematic overview of the domain architecture of the 6-Cys family members (t 6-cysteine and 4-cysteine domains shown as black squares and dark blue squares respectively. Predicted GPI anchor sequence (yellow hexagons) and signal sequence (thick red line) are indicated. C(i)-(iii) show comparative modelling of 6-cysteine (Pf12 D2) and 4-cysteine (PfB9) domains: (C(i)) A ribbon diagram of the crystal structure of Pf12 D2 domain (PDB 2YMO) is shown against the predicted structural image of the PfB9 4-Cys domain. (C(ii)) The two structures have been superimposed and two views (i.e. 90° rotation) are displayed. The mixture of parallel and anti-parallel β-strands of both the Pf12 and PfB9 domains closely align together creating in both structures the β-sandwich typical of the s48/45 domain. (C(iii)) A close up of the cysteine bridging between the β-sheets (boxed in black) showing the predicted di-sulphide bonding between Cys3&6 and Cys4&5 (circled in red) in both models structures. The di-sulphide bond between Cys1&2 (circled in blue) is absent in the PfB9 4-Cys domain.

Figure 15:
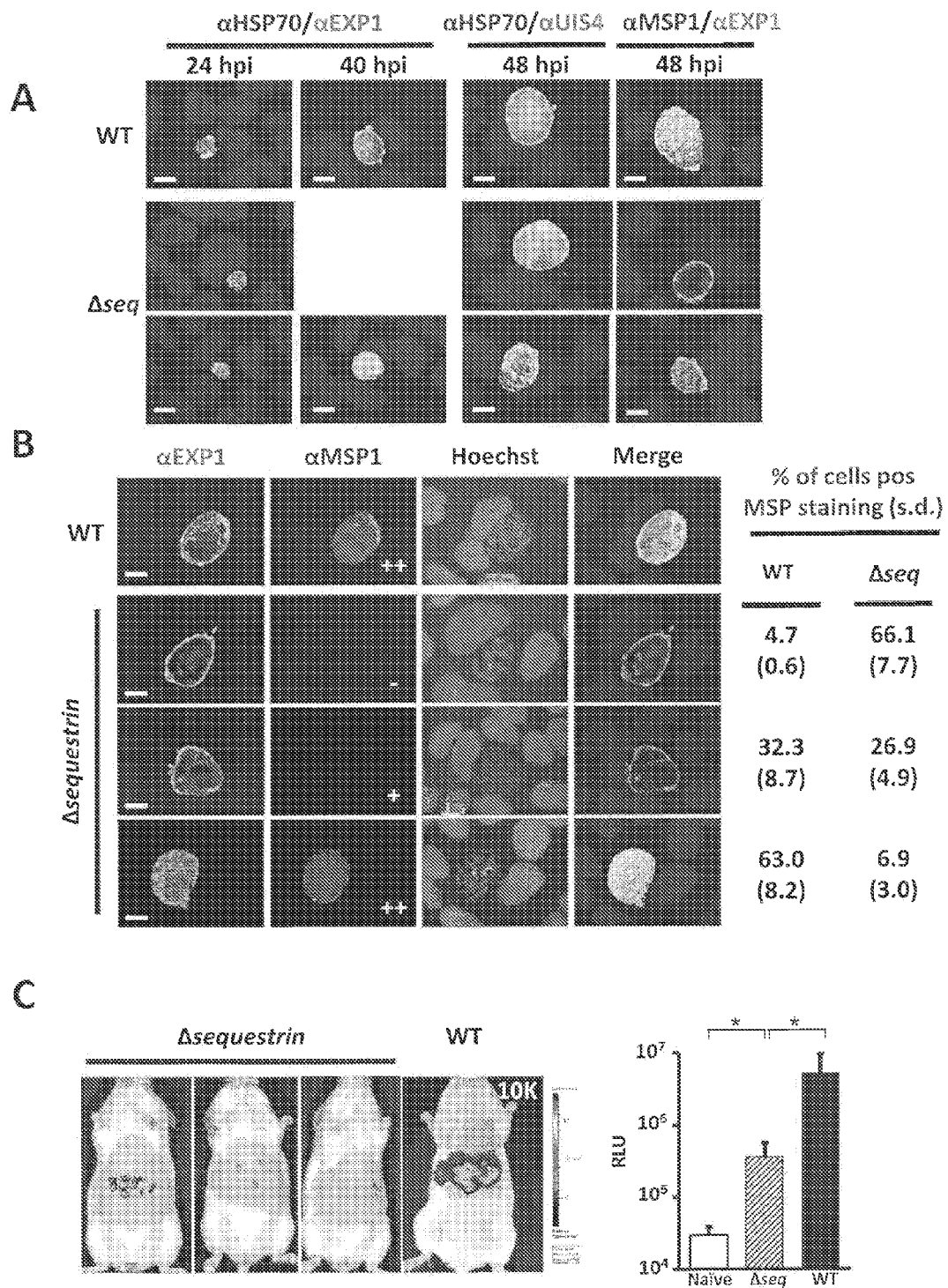

FIG. 15A-C: Liver stage development of PbΔsequestrin. (A) Development of liver stages in cultured hepatocytes as visualized by staining with antibodies recognizing the PVM (anti-EXP1 and anti-UIS4; green), the parasite cytoplasm (anti-HSP70; red) and merozoites (anti-PbMSP1; red). Nuclei are stained with Hoechst-33342; hpi: hours post infection. (B) Analysis of MSP1 expression at 54 hpi as a marker for merozoite formation. Parasites are stained with anti-MSP1 (red) and anti-EXP1 (green)-antibodies. MSP1 levels are determined from images acquired using different exposure times: MSP1++: MSP1 visible after 0.5 s exposure); MSP+: MSP1 only visible after 4 s exposure (4 s); MSP-: MSP1 absent after exposure >4 s. All images show the short exposure of 0.5 s. The percentage (mean and standard deviation, s.d.) of MSP1-staining positive parasites in the population is indicated. Nuclei are stained with Hoechst-33342 (blue). (C) Reduced PbΔsequestrin liver stage development, as shown by real time in vivo imaging of luciferase-expressing liver stages at 42 h after infection with $10^4$ sporozoites. Graph on the right shows the relative luminescence intensity (relative light unites, RLU) at 42 hpi of SWISS mice infected by intravenous inoculation of $10^4$ (10K) WT and PbΔsequestrin sporozoites. *p<0.05, student T-test.

FIG. 16A-F: Liver stage development of PbΔb9. (A) RT-PCR analysis showing the absence of b9 transcripts in Δb9 sporozoites (spz). using the primers shown in the left pane 1 in the presence (RT+) or absence (RT−) of reverse transcriptase-; cs: *P. berghei* circurnsporozoite protein gene and WT: wild type sporozoite RNA. (B) Intra-hepatic sporozoites (spz) in hepatocytes (3 hours post infection (hpi), n.s., not significant, student T-test. (C) Intracellular liver stages in hepatocytes at 24 hpi (identified as HSP70 positive cells; see D). WT parasites (mean 1338; range 1200-1500 infected hepatocytes/well); Δb9-a (mean 5; range 4-8 infected hepatocytes/well) and; Δb9-b (mean 7; range 5-11 infected hepatocytes/well) *p<0.001; n.s., not significant, student T-test. (D) Aborted development of Δb9 liver stages (nuclei stained with Hoechst-33324 (blue); e parasite cytoplasm stained with anti-HSP70 (red). Scale bar 10 μm. (F) Development of PbΔb9 and WT liver stages at 42 hpi in C57BL/6 mice as shown by real time in vivo imaging. All mice infected with WT spz developed blood infections (prepatent period of 5 days) whereas 8 out of 10 mice infected with PbΔb9 spz did not develop a blood infection. In 6 of 8 mice that did not develop a blood infection, no liver stages were present at 42 hpi, (F) Graph showing the relative luminescence intensity (relative light units; RLU) of C57BL/6 mice infected with WT or PbΔb9 sporozoites as shown in and depicted as relative light units (RLU). *p<0.001, student T-test.

FIG. 17A-G: Liver stage development of PyΔb9 and PfΔb9. (A) Liver stage development of PyΔb9 in BALB/c mice shown by real time in vivo imaging. All mice developed blood infections (prepatent period of 3-4 days). Weak luminescence signals were detected in the livers of mice infected with $2\times10^5$ PyΔb9 spz. (B) Relative luminescence intensity (relative light units; RLU) of BALB/c mice infected with $10^4$ (10K) WT, $5\times10^4$ (50K) and $2\times10^5$ (200K) PyΔb9 sporozoites at 40 hpi, ***P<0.001, student I-test. (C) Schematic representation of the wild-type (WT) *P. falciparum* b9 genomic locus (PF3D7_0317100) and Δb9 gene deletion mutants before (Δb9gfp) and after FLPe-mediated removal of the hdhfr::gfp resistance marker (Δb9*FLPe). The pHHT-FRT-GFP-B9 construct contains two FRT sequences (red triangles) that are recognized by FLPe, P1, P2: primer pairs for LR-PCR analysis; S (SpeI), R (RcaI), H (HindIII); restriction sites used for Southern blot analysis and sizes of restriction fragments are indicated; cam: calmodulin; hrp: histidine rich protein; hsp: heatshock protein; fcu: cytosine deaminase/uracil phosphoribosyl-transferase; hdhfr::gfp: human dihydrofolate reductase fusion with green fluorescent protein; pbdt: *P. berghei* dhfr terminator. (D) Long range PCR (LR-PCR) of genomic DNA confirming b9 disruption and subsequent removal of the hdhfr::gfp resistance marker. The PCR (primers P1 and P2) product is digested with XmaI (X) for confirmation (WT, 5.5 kb fragment, undigested; Δb9-a, 5.6 kb is digested into 4.4 kb and 1.2 kb fragments; Δb9-be, 2.6 kb is digested into 1.2 and 1.4 kb fragments). Southern analysis of restricted (RcaI) genomic DNA probed with the 5'b9 targeting region (P: 5' b9-T; see A) on the left and restricted (HindIII/SpeI) genomic DNA probed with the 3'b9 targeting region (P: 3' b9-T; see A) on the right. RT-PCR analysis showing absence of b9 transcripts in *P. falciparum* Δb9-b sporozoites (spz). PCR amplification using purified spz RNA was performed in the presence (RT+) or absence of reverse transcriptase (RT−); positive control 18S rRNA (primers 18Sf/18Sr). (E) Cell traversal (Top panel) of *P. falciparum* WT and PfΔb9-a (PfΔb9) sporozoites (spz). Dextran control (Dex): hepatocytes in the presence of Dextran without addition of spz. Intra-hepatic spz in primary human hepatocytes (Bottom panel) as determined in the double CS antibody staining assay. (F) Development of PfΔb9-a liver stages in primary human hepatocytes from day 2 to day 7(2 exp.). The number of parasites per well was determined by counting parasites stained with anti-HSP70 antibodies. *Total number of liver-stages observed in 3 wells; none detected (nd). (G) Immunofluorescence detection of Δb9 parasites in human primary hepatocytes. Parasites stained with anti-PfCSP antibodies (green; Alexa-488). Nuclei stained with DAPI (blue). Scale bar 10 μm.

Figure 18:
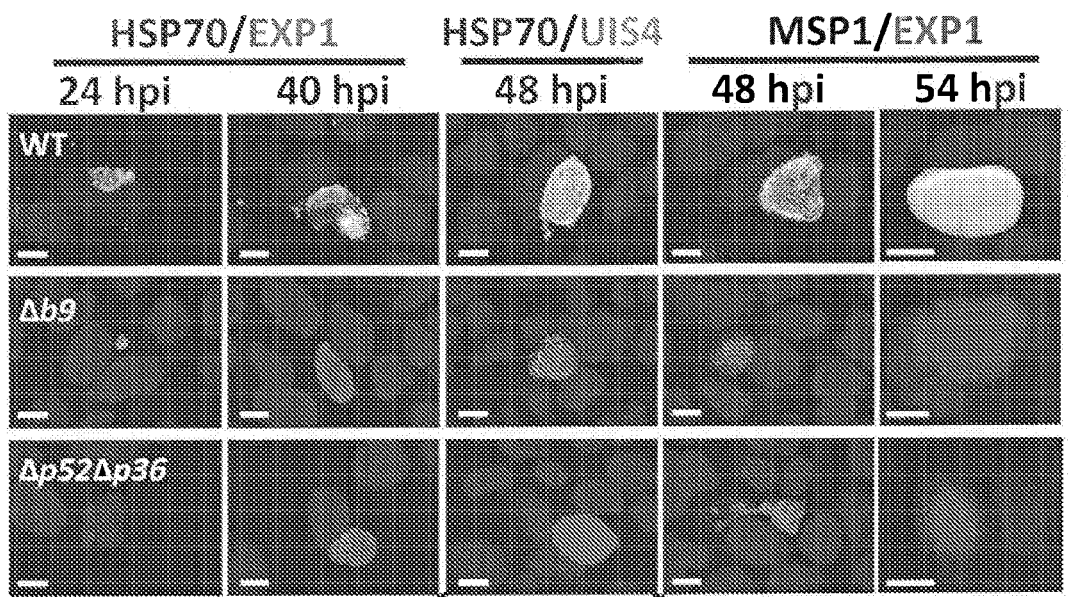
Figure 18:
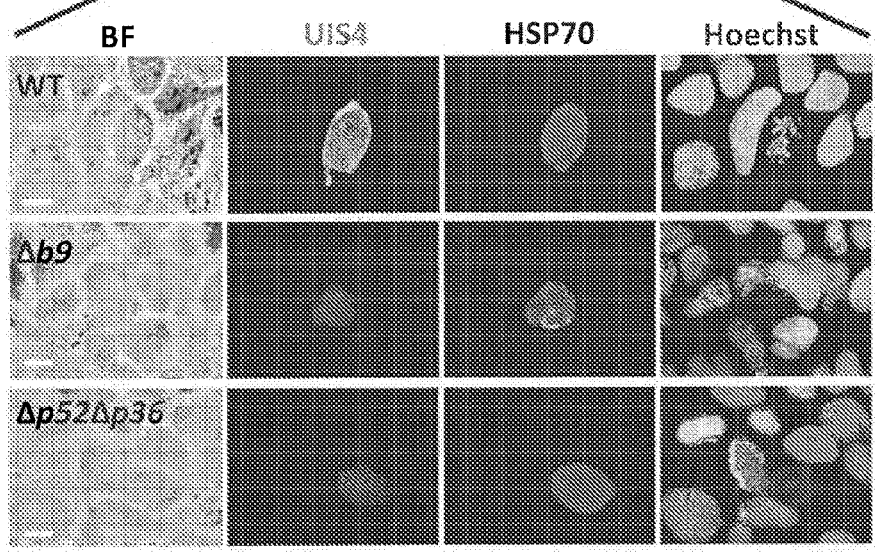

FIG. 18A-B: The few Δb9 parasites that develop into mature liver stages have a compromised parasitophorous vacuole membrane. (A) Maturation of PbΔb9 and PbΔp52Δp36 liver stages in cultured hepatocytes visualized by staining with antibodies recognizing the parasite cytoplasm (anti-HSP70; red), the PVM (anti-EXP1; anti-UIS4; green) and the formation of merozoites (anti-PbMSP1; red). HSP70 and MSP1 staining shows maturation of liver stages in the absence of the PVM-specific proteins EXP1 and UIS4. (B) The staining at 48 hpi with anti-UIS4, anti-HSP70 as well as the bright-field (BF) images are shown as separate images below the main image, demonstrating both a reduction and cytoplasmic location of UIS4. Nuclei are stained with Hoechst-33342 (blue). Scale bar 10 μm.

FIG. 19A-D: Expression of B9 in *P. falciparum* liver stages. (A) WT sporozoites (spz) after staining with anti-PfCSP and anti-B9 antibodies. Spz were treated (+) or not treated (−) with cytochalasin D (CyD), an inhibitor of sporozoite motility. Sporozoites (and gliding trails) are stained with anti-CS antibodies but not with anti-B9 antibodies. (B) WT parasites in primary human hepatocytes at 3 and 24 hours post infection (hpi) stained with anti-PfCSP antibodies (green; Alexa-488) and anti-B9 antibodies (red; Alexa-594). (C) Left hand side images: Development of WT parasites in primary human hepatocytes from day 2 to 7 as visualized by staining with anti-HSP70 antibodies (green; Alexa-488) and anti-B9 antibodies (red; Alexa-594). Right hand side images: Development of WT parasites in primary human hepatocytes from day 2 to 7 as visualized by staining with anti-B9 antibodies (green; Alexa-488) and anti-EXP1 antibodies (red; Alexa-594). Parasite and hepatocyte nuclei are stained with DAPI (blue). (D) WT parasites in primary human hepatocytes on day 4 and 5 stained with anti-B9 antibodies or anti-MSP1 (green; Alexa-488) and antibodies against the PVM-protein EXP1 (red; Alexa-594). Parasite and hepatocyte nuclei are stained with DAPI (blue). Scale bar 10 μm.

FIG. 20A-D: mCherry expression in sporozoites and liver stages of transgenic mCherry$_{b9}$ (A) Fluorescence microscopy of midguts (MG) and salivary gland (SG) of mosquitoes at day 20 after infection with mCherry$_{b9}$ and mCherry$_{hsp70}$ No mCherry fluorescence (red) could be detected in mosquitoes infected with mCherry$_{b9}$. (B) mCherry-fluorescence (red) in salivary gland sporozoites (SPZ) of mCherry$_{b9}$ (bottom row) and mCherry$_{hsp70}$ (top row) lines showing (near) absence of mCherry expression (see D) in mCherry$_{b9}$ sporozoites. Bright field (BF), DNA staining (Hoechst; Blue). (C) mCherry-fluorescence in mCherry$_{b9}$ liver stages in cultured hepatocytes at different hours post infection (hpi). See C for quantification of the fluorescence intensities of the different stages. (D) mCherry-fluorescence intensities of sporozoites and liver stages (exoerythrocytic forms, EEF). Pictures were taken of 30-40 parasites using a Leica fluorescence microscope (a DM-IRBE Flu) and fluorescent intensity was determined by gating on parasite area (i.e. mCherry positive area) and measuring maximum intensity of mCherry signal, using the ImageJ software. SG-SPZ: salivary gland sporozoites; 5 hr SPZ: 'slender-shaped' sporozoites at 5 hpi; 5 hr rounded SPZ: 'rounded up' (activated) sporozoites at 5 hpi.

FIG. 21 shows proteins (with a signal sequence) identified by searching the P. berghei genome with the new MEME based string search for 6- and 4-Cys motifs. Proteins highlighted in grey were upon manual inspection not included as 6-Cys domain containing proteins, pease see manuscript for details.

DETAILED DESCRIPTION OF THE INVENTION

Definitions

"Aseptic" as used herein means absent the introduction or presence of detectable microorganism contamination such as bacteria, fungi, pathologic viruses and the like. An aseptic method of sporozoite preparation results in a sterile preparation of sporozoites—free of any other type of microorganism or infectious agent. Aseptic preparation of a sterile composition is required for clinical and pharmaceutical use. Microbiological assays used to monitor an aseptic methodology assess the presence or absence of contamination. They include, but are not limited to, the Microbial Limits Test, current USP <61>, incorporated herein by reference. An aseptic preparation of purified, live, attenuated *Plasmodium* sporozoite-stage parasites is necessary for the preparation to be considered suitable for clinical or pharmaceutical use.

"Attendent material" as used herein refers to material in a crude preparation of sporozoites which is not the carrier or excipient and is not specific to the sporozoites per se. Attendent material includes material specific to the sources from which sporozoites were grown or produced, particularly biological debris, more particularly protein other than carrier or excipient, said attendant material initially isolated along with sporozoites in a crude preparation and removed from a purified preparation.

"Attenuation" as used herein means a gene alteration or mutation of an organism such as a *Plasmodium* parasite, such that it loses its ability to complete its normal life cycle, but rather it arrests at a particular stage of development. In the *Plasmodium* organisms of the instant invention, the functions of one or more genes of a GAP are disrupted such that the attenuated mutant retains the ability to infect a host and invade hepatocytes within the liver, but arrests development in liver-stage.

"Conferring protective immunity" as used herein refers to providing to a population or a host (i.e., an individual) the ability to generate an immune response to protect against a disease (e.g., malaria) caused by a pathogen (e.g., *Plasmodium falciparum*) such that the clinical manifestations, pathology, or symptoms of disease in a host are reduced as compared to a non-treated host, or such that the rate at which infection, or clinical manifestations, pathology, or symptoms of disease appear within a population are reduced, as compared to a non-treated population.

"Challenge" as used herein refers to exposure of an immunized subject to a normally pathogenic malaria-causing vector.

"Developmental Arrest" as used herein means the inability of an organism to move beyond a particular stage of development, usually as a result of attenuation. In the *Plasmodium* organisms of the instant invention, GAPs are attenuated to developmentally arrest in liver-stage.

"Developmental Stages" as used herein refer to the life cycle stages of the *Plasmodium*-species organism. The developmental stages relevant to this invention include: the sporozoite stage, liver stage and blood stage. Infection of a mammalian host is initiated when sporozoite stage parasites are injected into the host along with the saliva of a feeding mosquito. Sporozoites migrate in the circulatory system to the liver and invade hepatocytes. The intracellular parasite thus enters the liver stage of development and undergoes asexual replication known as exoerythrocytic schizogony. Parasites in the late stages of development in the liver are referred to as merozoites. Merozoites are released into the bloodstream and thus begin the blood stage of development.

"Dose" as used herein means the amount of a vaccine administered to a subject at a given time. "Dosage" as used herein means the number of doses in a regimen or the total amount of vaccine provided to a subject in said regimen.

"Hepatocyte Invasion" as used herein refers to the ability of the sporozoite-stage of the *Plasmodium* parasite to seek out and enter particular target cells, in this case, host hepatocytes, after initial introduction into the circulatory system of a host. Non-attenuated parasites would then undergo further stage-specific development.

"Immune response" as used herein means a response in the recipient to an immunogen. More specifically as described herein it is the immunologic response in an individual to the introduction of attenuated sporozoites generally characterized by, but not limited to, production of antibodies and/or T cells. Generally, an immune response to *Plasmodium* sporozoites may be a cellular response such as induction or activation of CD4+ T cells or CD8+ T cells specific for *Plasmodium* species epitopes, a humoral response of increased production of *Plasmodium*-specific antibodies, or both cellular and humoral responses. With regard to a malaria vaccine, the immune response established by a vaccine comprising sporozoites includes but is not limited to responses to proteins expressed by extracellular sporozoites or other stages of the parasite after the parasites have entered host cells, especially hepatocytes and mononuclear cells such as dendritic cells and/or to components of said parasites. In the instant invention, upon subsequent challenge by infectious organisms, the immune response prevents development of pathogenic parasites to the asexual erythrocytic stage that causes disease.

"Immunogen" as used herein refers to the immunogenic component of a vaccine that elicits the intended and particular immune response.

"Metabolically active" as used herein means alive, and capable of performing sustentative functions and some life-cycle processes. With regard to attenuated sporozoites this includes but is not limited to sporozoites capable of invading hepatocytes in culture and in vivo, potentially having a limited capacity to divide and progress through some developmental stages within the liver, and de novo expression of stage-specific proteins.

"Prevent" as defined herein and used in the context of preventing malaria means to keep a majority, up to all, of the pathology and clinical manifestations of malaria from manifesting.

"Protection" as used herein refers to either: a) for an individual, the prevention of the signs, symptoms and pathology of malaria; or, b) with regard to a population of individuals, reduction in the number of infected individuals displaying the signs, symptoms, and pathology of malaria, subsequent to vaccination and upon challenge by a pathogenic vector that would normal cause the disease.

"Purified" with regard to a preparation of sporozoites means reduction in the amount of attendant material to less than 85 ng/25,000 sporozoites or at least a 18 fold reduction in attendant contamination. Purified *Plasmodium* sporozoites has been described in Sim et al (U.S. Pat. No. 8,043,625) incorporated herein by reference.

"Regimen" as used herein refers to the mode, dose, frequency and number of vaccine dosages administered in a coordinated methodology.

"Vaccine" as used herein refers to a pharmaceutical composition appropriate for clinical use and designed for administration to a subject, where upon it elicits an intended and particular immune response. Vaccines disclosed herein comprise aseptic, purified, genetically attenuated, metabolically active *Plasmodium* sporozoites functioning as immunogen, and a pharmaceutically acceptable diluent potentially in combination with excipient, adjuvant and/or additive or protectant. When the vaccine is administered to a subject, the immunogen stimulates an immune response that will, upon subsequent challenge with infectious agent, protect the subject from illness or mitigate the pathology, symptoms or clinical mat infestations caused by that agent. A therapeutic (treatment) vaccine is given after infection and is intended to reduce or arrest disease progression. A preventive (prophylactic) vaccine is intended to prevent initial infection or reduce the rate or burden of the infection.

"Suitable for human pharmaceutical use" as used herein refers to having a sufficient quantity, sterility (asepticity), and purity for approved clinical use in humans.

"Wild type" as used herein refers to the non-genetically engineered *Plasmodium*-species organism from which a mutant (e.g., knock-out or double knock-out) *Plasmodium*-species organism is derived.

"Mutant" as used herein refers to a genetically altered gene or organism. The genetic alteration can include, e.g., deletions, insertions, or translocations. In an embodiment, the mutant is a knock-out with at least one disrupted gene function or a double knock-out with at least two disrupted gene functions.

Genetically Attenuated Parasite (GAP) Candidates

Based on the low levels of breakthrough GAP parasites, a set of safety criteria were devised to be met in *P. berghei* by a GAP candidate for use as a vaccine immunogen prior to clinical development of GAP in *P. falciparum* [14]. Adequacy of GAP attenuation can be assessed, e.g., by testing for breakthrough blood stage infections in different mice strains inoculated with a high number of GAP sporozoites. Moreover, in vivo imaging of parasites can be used to further attest the absence of GAP developing in the liver.

In order to find a GAP that completely arrests in the liver stage and for which immunization confers long-lasting protection, certain embodiments include, e.g., i) combining mutations of known GAP candidates into one multiple attenuated GAP or ii) pursuing new mutations that would be useful as GAP candidates. This application relates to unique combinations of known mutations to create unique GAP candidates as well as the generation and characterization of a new mutation that by itself or in combination with other mutations results in unique GAP candidates. In an embodiment a first mutation is transcribed but translationally repressed in sporozoite stage of development and translationally expressed in the liver stage of development, such that the parasite arrests development during liver stage and does not enter the blood stage of development. These criteria are typified by Δb9, a unique gene mutation, which is disclosed in detail herein. Also disclosed herein is the combination of new gene mutations with other known gene mutations of non-overlapping function to create novel multiple knockout GAP candidates. Disclosed herein is a GAP candidate comprising the single Δb9 knockout as well as GAPs attenuated by multiple knockouts. In an embodiment, a double deletion of the b9 and the slarp genes is disclosed. In certain embodiments, the GAP candidate of the application completely arrests in the liver.

P. berghei Δslarp and its orthologue in P. yoelii, Δsap1, mutant parasites completely arrest in the liver. An orthologue of the Δslarp gene is present in P. falciparum [15, 16] and disclosed herein is the generation and analysis of a novel P. falciparum genetically attenuated parasite (GAP) PfΔb9Δslarp, which can invade cells of the liver (hepatocytes) but is unable to replicate, and arrests during liver-stage development. As disclosed herein these mutant parasites are able to progress through blood and mosquito stages like wild type (wt) parasites. The results disclosed herein establish that the GAP candidates disclosed herein would be both useful and practical to manufacture. In an embodiment, the b9 gene is deleted from the genome. In an embodiment, the b9 gene is mutated and functionally inactivated. In an embodiment, the slarp gene, lisp1 gene, lisp2 gene, lsa1 gene, lsa3 gene, or any combination of genes thereof is deleted from the genome. In an embodiment, the slarp gene, lisp1 gene, lisp2 gene, lsa1 gene, lsa3 gene, or any combination of genes thereof is mutated and functionally inactivated. In one embodiment, the PfΔb9Δslarp GAP disclosed herein has two genes (involved in independent biological functions) removed (or deleted) from the genome, specifically b9 and slarp.

In an embodiment, the PfΔb9Δslarp GAP (lacking both b9 and slarp) produces wild type numbers of salivary gland sporozoites. As disclosed herein, PfΔb9Δslarp GAP can infect primary human hepatocytes at wild type levels, but PfΔb9Δslarp are unable to replicate and they arrest during liver stage of development, 24 hours after invasion, and do not enter the blood stage of development. These parasites are also unable to fully develop in livers of chimeric mice engrafted with human liver tissue. The results disclosed herein using the rodent PbΔb9Δslarp and the human PfΔb9Δslarp parasite demonstrates that the Δb9Δslarp is able to multiply and is completely attenuated during liver stage development, does not enter the blood stage of development, and is ready/safe for clinical testing and development.

The b9 Gene

Malaria is caused by the Apicomplexan protozoan parasitic organism Plasmodium, which propagates by alternating its development between a mosquito vector and a vertebrate host. Infected mosquitoes transmit a developmental form of the Plasmodium parasitic organism called sporozoites, which rapidly migrate to the host liver, invade hepatocytes, and differentiate into replicative liver stages (LS). After intensive multiplication, a developmental form called merozoites are released from the liver into the blood. This begins the blood stage of development during which the parasites invade erythrocytes, after which the signs, symptoms and pathology of malaria appear.

The Plasmodium organism undergoes several morphological changes during its life cycle from forms that mediate invasion into host cells, those that multiply within the cell, as well as those that initiate and complete sexual reproduction inside the mosquito. These changes involve specialized, often Plasmodium specific, proteins that have a stage-specific pattern of expression in the mosquito and vertebrate hosts, and include a wide range of molecules involved in interactions between the parasite and specific host cells. Among these are proteins of the Plasmodium specific 6-Cys family of proteins that contain a cysteine-rich domain—the 6-cysteine or s48/45 domain [51, 52]. In Plasmodium particular 6-Cys proteins are expressed in a discrete stage-specific manner at different life cycle stages such as gametes, sporozoites or merozoites.

Identification of New Members of the 6-Cys Protein Family

Ten 6-Cys proteins had been identified based on the presence of at least two 6-cysteine or s48/45 domains [51, 52] and all proteins contain a signal sequence. In FIG. 14A the conserved arrangement of one of the domains from the P48/45 protein of six Plasmodium species is shown. Using all annotated 6-cysteine domains from the P. berghei and P. falciparum 6-Cys proteins (56 domains in total) an iterative BLAST search was performed against the P. berghei and P. falciparum genomes. This analysis identified two additional proteins, LISP2 (Liver stage specific protein 2), which is also referred to as sequestrin, (PF3D7_0405300 (P. falciparum ortholog); PBANKA_100300 (rodent parasite)) and the P. falciparum specific protein Pf92 (PF3D7_1364100). Sequestrin contains a single 6-cysteine domain and Pf92 does not contain a canonical 6-cysteine domain but retains only the last four cysteines of the domain (FIG. 14B). Several canonical 6-Cys proteins also contain one or more of such '4-cysteine domains', P. falciparum P48/45 has three s48/45 domains where the 2nd domain contains four cysteines (FIG. 14B, [51, 53, 54]). In P. berghei, both the 1st and 2nd domain of P48/45 and the 1st domain of both P38 and P12p contain only four cysteines (FIG. 14B). Based on these observations we performed a MEME analysis of all 6-cysteine and 4-cysteine domains of the P. falciparum and P. berghei 6-Cys proteins (including sequestrin and Pf92), resulting in the identification of three conserved motifs (FIG. 14A): motif 1 (15 amino acids) which contains Cys3 (e-value $8.6e^{-107}$); motif 2 (14 amino acids) which contains Cys4 (e-value $4.3e^{-119}$) and motif 3 encompassing both Cys5 and Cys6 (e-value $4.1e^{-026}$). Based on the MEME analysis the P. berghei genome was searched using the following search string: ØxØxCx$_n$C[F,S,T]x$_n$[F,I,L]xCxC where Ø is any hydrophobic amino acid (Phe, Trp, Met, Pro, Ala, Val, Leu, Ile, Gly), x is any single amino acid residue, x$_n$ is any number of amino acids, C is cysteine, F is phenylanine, S is serine and T is threonine. This search retrieved a total of 136 proteins of which only 16 also were predicted to encode a signal sequence and this included the 10 known 6-Cys proteins members and sequestrin (FIG. 21). Of the remaining 5 proteins, 3 contained atypical 4-cysteine domains by manual inspection and were excluded from further analysis. Two of these excluded proteins (PBANKA_121810 and PBANKA_081940) have long intervening regions between the three MEME motifs, resulting in domains that are considerably greater in length than the 350aa of the 6-Cys domains [54] and did not retain the structure of the 6-Cys domain [51, 53]. The third protein (PBANKA_120070) is very rich in cysteine residues both within and outside the predicted domain and, consequently, the disulphide bridging could not be accurately predicted. The remaining two proteins contained a 4-cysteine domain with a structure that is highly similar to the structure of 4-cysteine domains in the known 6-Cys proteins. These 2 proteins are the previously described protein PSOP12 (PF3D7_0513700; PBANKA_111340; [55]) and an uncharacterized protein (PF3D7_0317100; PBANKA_080810), which we term B9. B9 is predicted to be glycosylphosphatidylinositol (GPI) anchored. Six of the ten previously identified 6-Cys proteins as well as Pf92 also contain a GPI anchor motif (FIG. 14B). Modeling of the 4-cysteine domain of *P. falciparum* B9 on the recently described NMR and crystal structure of the s48/45 D2 of *P. falciparum* P12 [53, 62] indicates a high degree of structural similarity between these domains, specifically the parallel and antiparallel β-strands that constitute the characteristic 'β-sandwich' of the 6-cysteine domains (FIG. 14C). This β-sandwich fold has two of the three disulphide bonds from Pf12 6-Cys domain in the PfB9 4-Cys domain (i.e. Cys720-Cys804 and Cys731-Cys802 which correspond to Cys52-Cys113 and Cys63-Cys111 from Pf12 D2 domain (FIG. 14C). The overall domain architecture of the 6- and 4-cysteine domains and their location in the respective proteins are shown in FIG. 14B. Based on the structural analyses of the 4-cysteine domain and the presence of this domain in several previously identified 6-Cys proteins, we propose that the presence of the four positionally conserved cysteine residues, i.e. Cys3 to 6, are diagnostic for this domain and that P192, sequestrin, PSOP12 and B9 belong to the 6-Cys family-related proteins.

Sequestrin and B9 Play Critical Roles During *P. berghei* Liver-Stage Development PSOP12 has been detected in a proteome of *P. berghei* ookinetes but is absent from proteomes of blood-stages, oocysts and sporozoites, and mutants lacking this protein are able to complete development in the mouse and mosquito [55]. For sequestrin of *P. berghei* expression has been demonstrated in maturing liver stages [63, 64]. To determine the timing of expression of B9, we first analyzed b9 promoter activity using a transgenic *P. berghei* mutant expressing mCherry under the control of b9 regulatory sequences (mCherry$_{b9}$; FIG. 20A-D). No fluorescence signals were detected in blood-stages, oocysts and sporozoites, despite the presence of b9 transcripts in sporozoites. Strong fluorescence signals were detected in hepatocyte-culture 5 hours after the addition of mCherry$_{b9}$ sporozoites (FIG. 20A-D). The non-fluorescent sporozoites indicate that b9 transcripts are translationally repressed and that the B9 protein is generated after a developmental switch to intrahepatic development. Indeed, mCherry expression was observed both in intra-hepatic stages and in extracellular sporozoites that had been activated and started to 'round up'. Five hours post infection (hpi) fluorescence signals decreased; at 15 hpi weak signals were detected in all parasites and no fluorescence was detected at 24 hpi and 32 hpi (FIG. 20A-D).

To examine the function of sequestrin and B9 during liver-stage development we generated the *P. berghei* gene-deletion mutants PbΔsequestrin and PbΔb9. For both sequestrin and b9 two independent mutants were generated. PbΔsequestrin (LISP(-)) mutants (RMgm-799, http://pberghei.eu/index.php?rmgm=799&h1=LISP2) were generated using the *P. berghei* ANKA 2.34 line (PubMed: PMID: 15137943). PbΔb9 mutants are described above. Blood-stage development of PbΔb9 and PbΔsequestrin was comparable to wild type (WT) parasites as mice also develop 0.5-2% parasitemia after 8 days from an infection initiated by a single parasite, and they produced normal numbers of oocysts and sporozoites (Table 11). Sporozoites of both mutants showed normal gliding motility and WT-levels of hepatocyte invasion (Table 11). Mice infected with either 1 or 5×10$^4$ PbΔsequestrin sporozoites, intravenously, had a 2-3 day delay in blood-stage patency when compared to WT sporozoites infections (Table 10) and 4 out of 11 mice did not develop a blood-stage infection after inoculation with 1×10$^4$ sporozoites. These observations, both the absence of a blood stage infection in 4 out of 11 mice (injected with 1×10$^4$ sporozoites) and a prolonged prepatent period (2-3 days longer) of mice that did develop a blood stage infection, indicates that the absence of sequestrin strongly affects liver stage development. Specifically, a 2-3 day prolonged prepatent period represents a >99% reduction of liver stage development [44]. PbΔsequestrin liver stages have normal morphology, with respect to cell division, size and PVM formation at 24 hpi (FIG. 15A). However at 48 hpi, as determined by staining with anti-MSP1 antibodies, all liver-stage parasites were MSP1 negative (FIG. 15A). To investigate the maturation of these parasites, we examined 54 hpi parasites using anti-MSP1 and anti-EXP1 antibodies. Over 60% WT parasites at this time point were strongly MSP1 positive, whereas the majority of PbΔsequestrin parasites were MSP1 negative, with only around 7% of parasites exhibiting similar MSP1 staining (FIG. 15B). By using PbΔsequestrin parasites that expressed luciferase we were able to examine parasite development in the liver of mice using real-time in vivo. Imaging of mice infected with 1×10$^4$ PbΔsequestrin sporozoites, showed a strong reduction in luminescence signals (>10-fold reduction) compared to signals found in mice infected with the same number of WT-luciferase expressing sporozoites (FIG. 15C). Combined these observations show that sequestrin plays a role in late liver stage development which is in agreement with observations made by Orito et al. who show a role for sequestrin during late liver stage development and show that mutants lacking sequestrin have a 30-100 fold reduction in liver stage development [64].

Figure 16:
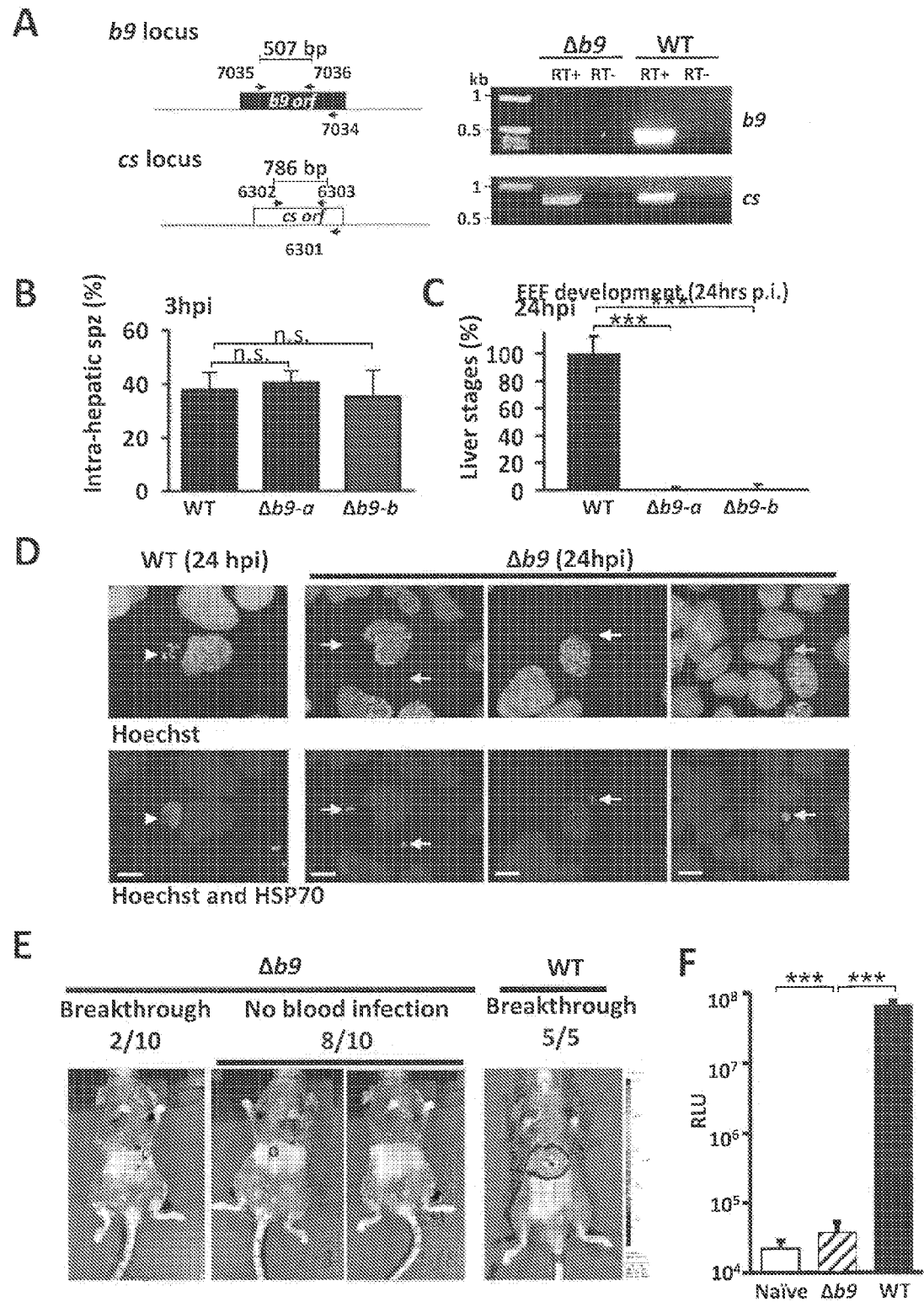

In WT parasites b9 transcripts are readily detected in salivary gland sporozoites by RT-PCR and are absent in PbΔb9 sporozoites (FIG. 16A). When Swiss or BALB/c mice were infected by intravenous inoculation of either 1 or 5×10$^4$ PbΔb9 sporozoites none of the mice developed blood-stage infections (Table 10). When C57BL6 mice were infected with a high dose of 5×10$^4$ PbΔb9 sporozoites, 10-20% developed a blood-stage infection with a 3-4 days prolonged prepatent period (Table 10). Immunofluorescence analyses show that PbΔb9 parasites arrest early after invasion of hepatocytes. PbΔb9 Sporozoites exhibit normal hepatocyte invasion, but at 24 hpi most intra-cellular parasites had disappeared and only a few small parasites could be observed with a size that was similar to 5-10 hpi liver stages (FIG. 16B-D). Analysis of PbΔb9 parasites in the liver, using real-time in vivo imaging, confirmed the early growth-arrest observed in cultured hepatocytes. In 6 out of 10 C57BL/6 mice infected with 5×10$^4$ PbΔb9 sporozoites we could not observe liver-stage development, as demonstrated by the absence of luminescence signals in the liver at 42 hpi and absence of blood infections (FIG. 16E). In the remaining 4 mice only weak luminescent signals were detected, confined to only a few small spots (FIG. 16E,F) and only two of these mice developed a breakthrough blood infection with a long prepatent period of 8 to 9 days (Table 10). Combined, our analyses demonstrate that PbΔb9 has a critical role during early liver stage development, although a few liver stages can complete liver-stage development in the absence of B9.

*P. yoelii* and *P. falciparum* Mutants Lacking B9 Arrest During Liver-Stage Development To determine if B9 has a conserved role in *Plasmodium* we generated *P. yoelii* and *P. falciparum* mutants lacking b9.

Figure 17:
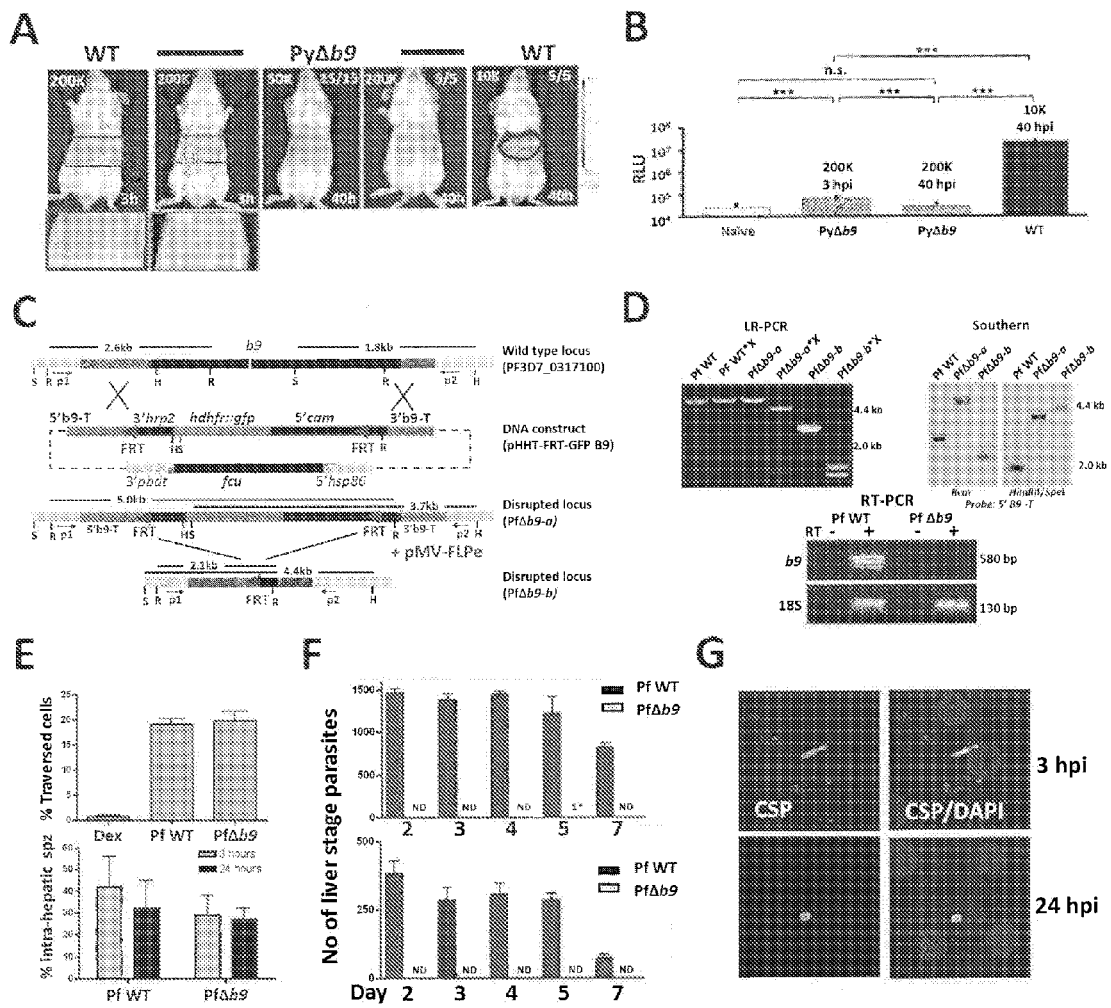

The *P. yoelii* mutant, PyΔb9, was generated in a reference line of *P. yoelii*, which constitutively expresses luciferase [65]. Development of PyΔb9 was like WT parasites in the blood (as they develop a 0.5-2% parasitemia after 8 days from an infection initiated by a single parasite) and in mosquito-stage development (Table 11). We analyzed liver-stage development in BALB/c mice after inoculation of $10^4$ or $2 \times 10^5$ sporozoites by in vivo imaging and analysis of subsequent blood-stage infections (FIG. 17A). In vivo imaging of mice infected with $2 \times 10^5$ PyΔb9 sporozoites showed faint luminescent signals in the liver at 3hpi that were significantly higher than background values of uninfected mice (FIG. 17A,B). At 40 hpi none of the infected mice showed luminescence signals above background. A blood-stage infection was only detected in 1 out of 8 mice infected with $2 \times 10^5$ sporozoites (Table 10) with a long prepatent period of 10 days. These results indicate that PyΔb9 parasites, like *P. berghei* Δb9, are severely compromised in liver stage development.

For *P. falciparum* two independent mutants lacking b9 were generated by double cross-over recombination and gene-deletion (FIG. 17C,D). Blood-stage development and gametocyte production of the PfΔb9 mutants was comparable to WT and they produced normal numbers of oocysts and sporozoites (Table 11). PfΔb9 sporozoites showed normal traversal and invasion of cultured primary human hepatocytes (FIG. 17E). In cultured primary human hepatocytes intracellular PfΔb9 parasites were observed until 24 hpi which were morphologically similar to WT parasites at the same point of development as determined by fluorescence-microscopy after staining with anti-CSP antibodies (FIG. 17F,G). However, at 48 hpi no PfΔb9 liver stages could be detected (FIG. 17F). These analyses show that *P. falciparum* parasites lacking B9 also abort liver-stage development soon after invasion of hepatocytes, comparable to the early growth arrest of *P. berghei* Δb9 parasites. Extensive analyses by fluorescence-microscopy of all hepatocyte cultures at day 2 to 7 revealed the presence of a single replicating parasite at day 5, which was comparable in size to 5-day old WT liver-stages. The presence of such replicating forms is in agreement with the phenotype observed in *P. berghei* and *P. yoelii* where at very low frequency parasites lacking B9 can develop in mature liver stages.

B9 is Critical for Integrity of the Parasitophorous Vacuole Membrane

Formation of the parasitophorous vacuole membrane (PVM) in PbΔb9 liver stages was analyzed by immunofluorescence-microscopy using antibodies against two PVM-associated proteins, EXP1 and UIS4. The very few arrested liver-stages present did not express EXP1 or UIS4 on the PVM (FIG. 18A-B). Similarly the few replicating liver stages of the PbΔp52Δp36 mutant also did not express EXP1 and UIS4 on the PVM (FIG. 18A-B, [44]). Indeed, there was only weak UIS4 staining in both PbΔb9 and PbΔp52Δp36 mutants, and this was confined to the cytoplasm of the parasite (FIG. 18A-B). The reduced and incorrect expression of these PVM-proteins indicates that both mutants have a compromised PVM and suggests that different 6-Cys proteins play a role in the generation and/or maintenance of a PVM.

Figure 19:
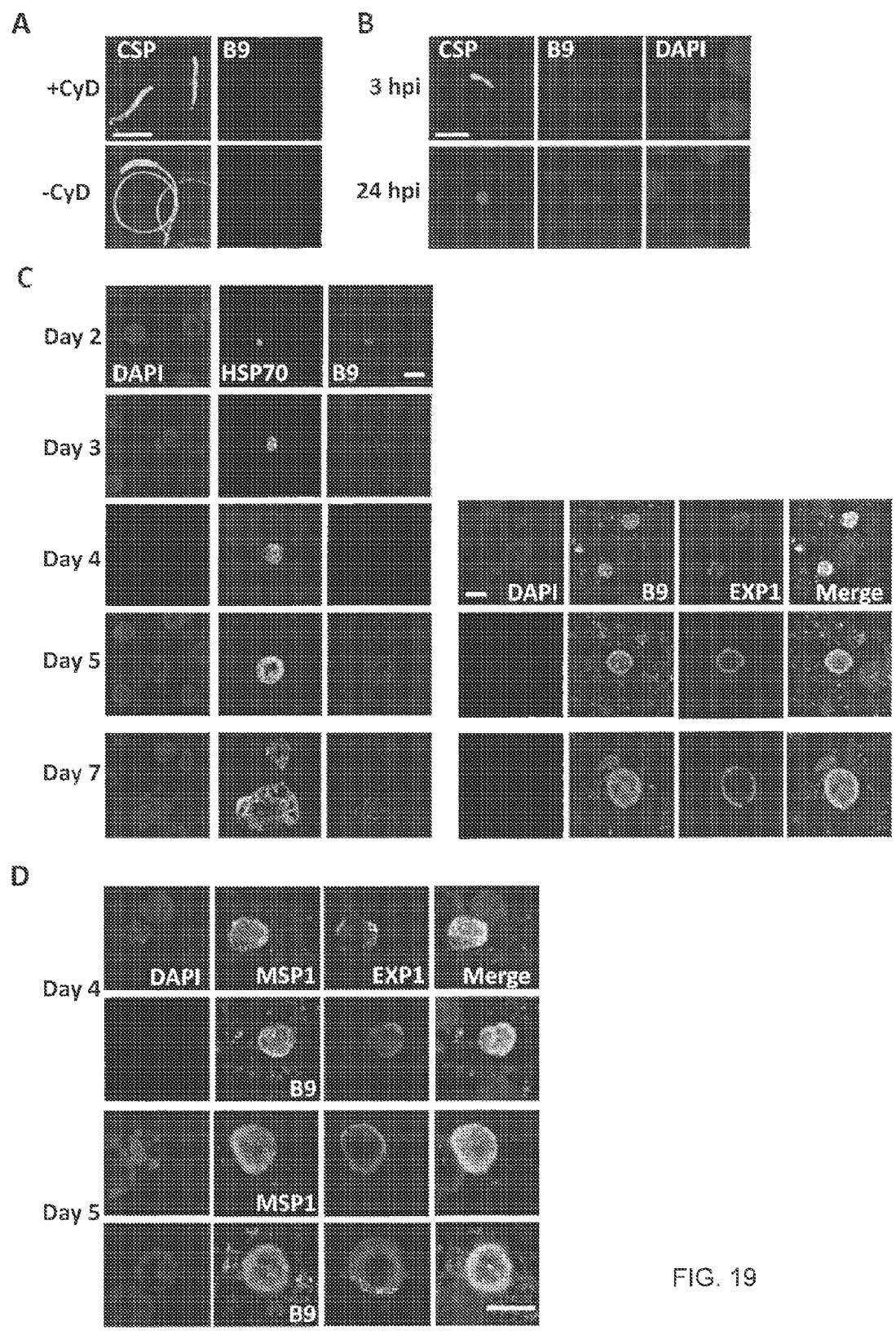
Figure 20:
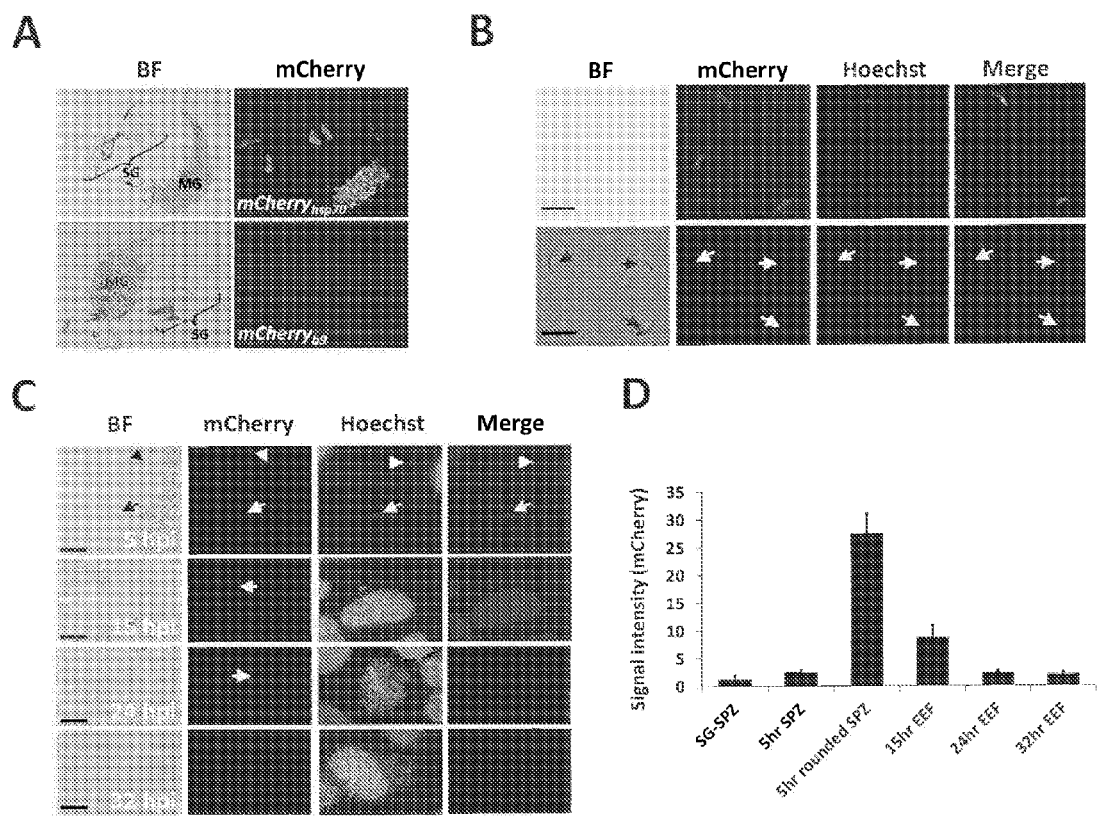

Antibodies against *P. falciparum* B9 were generated and analyzed *P. falciparum* B9 localization in sporozoites and liver stages (FIG. 19A-D). Though we were able to detect Pfb9 transcripts in sporozoites (FIG. 17D) we were unable to detect B9 protein in sporozoites or in young liver stages (3 hpi; FIG. 19A,B). Indeed expression of B9 as protein appears only to start at 24 hpi (anti-Pf B9 antibody staining is only very weakly positive at this time point; FIG. 19B), however, it is clearly present in the infected hepatocyte from day 2 onwards (FIG. 19C). B9 has a discrete localization within the cytoplasm of the parasite and is distributed along the plasma membrane of the parasite. Staining these stages with the PVM-resident protein EXP1 shows that B9 does not co-localize with EXP1 and is therefore not on the PVM; B9 can be detected directly surrounding the replicating liver stage parasites, indicating a location at the plasmalemma membrane-PV boundary (FIG. 19C). The B9 pattern of staining was compared to another GPI-anchored protein, MSP-1, which is known to localize to the parasite plasmalemma during schizogony. Both MSP1 and B9 have a very similar localization pattern; both are predominantly circumferentially distributed around the liver schizont, though both also are found in distributed patches within the liver-schizont (FIG. 19D).

The timing of expression of B9 after 24 hpi is in agreement with observations made with *P. falciparum* parasites lacking B9, where normal liver stages are detectable at 24 hpi and the loss of PfΔb9 liver-stages is between 24 hpi and 48 hpi (FIG. 17E,F).

Thus, the b9 gene (PF3D7_0317100), as disclosed herein, has been identified as a member of the *Plasmodium* 6-Cys protein family. The b9 gene encodes a B9 protein. The gene is transcribed, but translationally repressed in the sporozoite stage of development and translationally expressed in liver stages of *Plasmodium*-species development. In the genomes of both *P. yoelii* and *P. falciparum* an ortholog of the *P. berghei* b9 gene is present (PY00153 and PF3D7_0317100). These genes have a conserved syntenic location and share 79% and 37% amino acid sequence identity and 85% and 54% sequence similarity with *P. berghei* b9 (PBANKA_080810), respectively. As disclosed herein, B9-deficient mutants (Δb9), created in *Plasmodium*-species organisms, e.g., *P. berghei, P. yoelii* and *P. falciparum*, arrest in development soon after hepatocyte invasion.

A description of the identification of the b9 and sequestrin (lisp2) genes and B9 and sequestrin proteins of *Plasmodium* is disclosed in the manuscript of Annoura, T. et al (2014) *Plasmodium* 6-Cys Family-related Proteins Have Distinct and Critical Roles in Liver Stage Development. FASEB J., not published). The b9 gene, sequestrin (lisp2) gene, p52 gene, and p36 gene have all the characteristics of the genes described herein as a *Plasmodium*-species first gene, the disruption of which is an embodiment of the invention disclosed herein. The b9 gene was selected as an initial GAP first gene target. The presence of b9 transcripts in sporozoites (transcribed in sporozoites) and the absence of B9 protein expression in sporozoites (translationally repressed in sporozoites) contributed to the selection of the b9 gene. B9 was found to be a member of the 6-Cys family of *Plasmodium* proteins. This family includes P52 and P36, both of which are GAP candidates. The lack of B9 protein expression in salivary gland sporozoites suggests that the b9 transcripts are translationally repressed in sporozoite stage parasites, and only translated after sporozoites invade hepatocytes (translationally expressed in liver stage). It has been found that B9 is not expressed during the blood and mosquito stage parasites but is only present as protein during liver stage development. In an embodiment, the b9 gene is deleted from the genome. In an embodiment, the b9 gene is mutated and functionally inactivated. In an embodiment, a second mutated and functionally inactivated gene is slarp (the *P. yoelii* orthologue being sap1), lisp1

(PF3D7_1418100), lisp2 (PF3D7_0405300), lsa1 (PF3D7_1036400), lsa3 (e.g., PF3D7_0220000), or any combination thereof.

The Slarp Gene

Slarp is conserved in *Plasmodium* species, e.g., *P. falciparum* (PfSLARP/PF11_0480), *P. vivax* (PvSLARP/Pv092945), *P. knowlesi* (PkSLARP/PKH_094440), *P. yoelii* (PySLARP/PY03269, PY03923, Genbank accession no. EU579525) and *P. berghei* (PbSLARP/PB000542.00.0, PB000547.01.0, Genbank accession no. EU579524) [15]. Slarp is specifically expressed in sporozoites and liver stages.

Slarp has all the characteristics of the genes described herein as a *Plasmodium*-species second gene, the disruption of which is an embodiment of the invention disclosed herein. SLARP is required for processes critical for successful liver-stage development. Δslarp mutants show an excellent safety profile by full arrest in the liver in mice [45, 46]. The SLARP protein is involved in the regulation of transcription/transcripts in salivary gland sporozoites and expressed in early liver stages [17, 46]. Δslarp mutants seem to arrest at a later time point in liver stage development (at day two parasites are still observed), and as disclosed herein was tested to determine whether absence of the SLARP gene product would be fully non-complementary to the B9 gene product (without functional overlap) and would therefore act as a safety net in the combined double knockout. As disclosed herein, the Δslarp mutants did not show any breakthrough development in murine models and in primary human hepatocyptes no developing parasite were observed.

GAP Safety

In the *P. berghei* rodent model, genetic attenuation of the parasite by simultaneous deletion of the b9 and slarp genes, results in a fully arresting (i.e, no breakthrough infection) GAP that can induce strong long-lasting immune responses. Per se, deletion of the b9 gene leads to an arrest of the majority of *P. berghei* parasites early after invasion of hepatocytes by sporozoites. Immunization of mice with *P. berghei* Δb9, leads to long-lived sterile protection, but may not be fully safe in that some parasites can develop into blood stage parasites, however, initial safety evaluation in rodents demonstrated that PbΔb9 mutants have a stronger attenuation phenotype than mutants lacking the 6-Cys proteins P52 and P36 [13, 28, 36, 60]. This early growth-arrested phenotype is very similar to the phenotype described for mutants lacking expression of the P52 protein or lacking the proteins P52 and P36 [13, 14]. A lack of an apparent PVM in *P. berghei* Δp52Δp36 developing in the cytosol of a hepatocyte has also been observed [59]. Low numbers of *P. berghei* Δb9 parasites seem to avert an arrest in the hepatocyte in a similar fashion. These findings may indicate that B9, P52 and P36 play a similar or complementary role in the development of a PVM. Indeed, inoculation of C57B1/6 mice with high doses of triple gene deleted *P. berghei* Δb9Δp52Δp36 GAP sporozoites, showed that the multiple gene-deletion mutant Δb9Δp52Δp36 shows the same high level of growth arrest as the single gene-deletion mutant Δb9 (data not shown). On the other hand, the multiple attenuated Δb9Δslarp GAP disclosed in detail herein shows no evidence of breakthrough infection, and is absent of the safety concerns that exist for other mutant GAPs known in the art.

By adopting a robust and stringent screening approach for GAP safety [14], it is disclosed herein that the Δb9Δslarp GAP does not permit breakthrough infections. Using, e.g., in vivo imaging and multiple mice strains, the adequacy of GAP attenuation was determined. Both *P. berghei* Δslarp and Δb9Δslarp parasites met the screening criteria. Both mutant parasites did not replicate in hepatocytes after invasion. Moreover, both BALB/c and C57BL/6 mice remained negative for blood stage parasitemia after inoculation with high numbers of the mutant sporozoites disclosed herein. In an embodiment, the multiple attenuated Δb9Δslarp GAP has a safety advantage over the single gene deleted Δslarp GAP. In an embodiment, the full arrest of Δslarp/Δsap1 parasites results from a depletion of transcripts from one or more uis (up-regulated in sporozoites) genes [17]. In an embodiment, the combined effect of one or more of the down-regulated uis genes promotes full developmental arrest. In another embodiment, the uis genes are down-regulated, but not absent, and the simultaneous deletion of a first gene, e.g., b9, and one or more uis genes in one parasite promotes full developmental arrest.

Vaccine Compositions

Pharmaceutical compositions comprising aseptic, purified, live attenuated *Plasmodium* sporozoites, and methods of using these compositions as the immunogen in prophylactic vaccines to prevent malaria have been provided [47]. Various categories of attenuated sporozoites have been considered for use in vaccines, including sporozoites attenuated by various methods, i.e. heritable genetic alteration, gene mutation, radiation exposure, and chemical exposure. In addition to the organisms disclosed herein, various attenuated organisms created by direct genetic manipulation of the parasites have been described for *P. falciparum* [36] as well as murine-specific *Plasmodium* species [13, 28, 43]. The engineered organisms disclosed herein are grown aseptically by the methods disclosed in Hoffman and Luke (2007) U.S. Pat. No. 7,229,627, and purified by the methods disclosed in Sim et al., (2011) U.S. Pat. No. 8,043,625. Both patents are incorporated herein by reference.

In an embodiment, attenuated *Plasmodium* sporozoites may be genetically manipulated to contain exogenous genes of other *Plasmodium*-species or of other pathogenic organisms that may be expressed prior to, during or subsequent to infection.

In an embodiment, compositions and vaccines comprising aseptically prepared attenuated purified sporozoites are useful to generate immune responses and provide partial, enhanced, or full protection in human and other mammalian subjects not previously exposed to a malaria-causing pathogen, or exposed, but not fully protected. These compositions and vaccines are similarly useful to reduce the chance of developing a disease-producing infection from parasites that causes malaria, including species of *Plasmodium*, e.g. *P. falciparum* or *P. vivax*, and the like, and reduce the chance of becoming ill when one is infected, reduce the severity of the illness, such as fever, when one becomes infected, reduce the concentration of parasites in the infected person, or reduce mortality rates from malaria in populations exposed to malaria parasites. In many cases even partial protection or delay in the time it takes an immunized individual as compared to a non-immunized individual to become infected with the parasites or ill from infection is beneficial. Similarly, a vaccine treatment strategy that results in any of these benefits in about 30% of a population may have a significant impact on the health of a community and of the individuals residing in the community.

Provided are methods for generation of an immune response and prevention of malaria in a subject. The methods comprise administering to the subject a vaccine, which has been prepared aseptically and comprises substantially purified live attenuated *Plasmodium* sporozoites in an amount effective to generate an immune response or to prevent malaria.

The subject to which the vaccine is administered in accordance with these methods may be any human or other mammal, susceptible to infection with a malaria parasite. For such methods, administration can be via the alimentary tract, such as oral, or administration can be parenteral, including, but not limited to mucosal, intranasal, epidermal, cutaneous, intramuscular, subcutaneous, intradermal, submucosal, intravenous and the like. Moreover, the administration may be by continuous infusion or by single or multiple boluses as well as delivery mediated by microneedles.

The prevention and/or treatment of malaria may be readily ascertained by the skilled practitioner by means of evaluation of clinical or pathological manifestations associated with malarial infection, for example elevated temperature, headache, fatigue, coma, or percent of erythrocytes parasitized. Thus, according to the methods of the present invention, the subject shows improved or absent clinical signs, symptoms or pathological manifestations of malaria following administration of a vaccine comprising purified live attenuated *Plasmodium* sporozoites.

Effective and optimal doses and dosage ranges for vaccines and immunogens can be determined using methods known in the art. Guidance as to appropriate dosages to achieve an anti-malarial effect is provided from the exemplified assays disclosed herein. More specifically, results from the immunization pattern described herein and in cited references can be extrapolated by persons having skill in the requisite art to provide a test vaccination schedule. Volunteer subjects are inoculated with varying doses at scheduled intervals and test blood samples are evaluated for levels of protection against malaria upon subsequent challenge with infective parasites. Such results can be used to refine an optimized immunization dose and dosage regimen (schedule) for effective immunization of mammalian, specifically human, subjects. It is anticipated that optimized doses and dosage regimens will vary generally with the general body mass of the subject and infants and small children will require proportionally less immunogen than adults. Furthermore, optimized doses and dosage regimens vary depending on the mode of administration, with intra dermal, subcutaneous and intramuscular administration requiring more immunogen than intravenous administration. A total dosage effective in conferring a protective immunity and/or generating an immune response is from 10,000 to 2,000,000 or 10,000 to 6,250,000 purified attenuated sporozoites administered in a regimen of 1 to 6 doses, more particularly a dose of from 25,000 to 400,000 or 50,000 to 1,250,000 purified attenuated sporozoites in a dosage regimen of at least 3 doses, and most particularly a dose of from 250,000 to 1,000,000 or 50,000 to 200,000 purified attenuated sporozoites in a dosage regimen of 3 to 5 doses. In an embodiment, the dose is at least 10,000, at least 50,000, at least 100,000, at least 250,000, at least 500,000, at least 1,250,000 or at least 6,250,000 genetically engineered sporozoites or GAP. In an embodiment, the dosage is 10,000 to 6,250,000; 50,000 to 1,250,000; 50,000 to 2,000,000; 100,000 to 1,000, 000; 250,000 to 750,000; or 250,000 to 1,000,000 genetically engineered sporozoites or GAP.

An immune response in a subject can be measured by standard tests including, but not limited to the assessment of humoral and cellular immune responses, including, but not limited to: measurement of antigen specific or parasite stage specific antibody responses; direct measurement of peripheral blood lymphocytes by means known to the art; natural killer cell cytotoxicity assays [56], cell proliferation assays [58], immunoassays of immune cells and subsets [66, 67]; and skin tests for cell mediated immunity [68]. Various methods and analyses for measuring the strength of the immune system have been described, for example, Coligan et al. (Ed.) (2000) Current Protocols in Immunology, Vol. 1, Wiley & Sons.

The vaccines provided comprise aseptic, purified compositions of purified live attenuated *Plasmodium* sporozoite (GAP) substantially free of attendant material that are acceptable for pharmaceutical use, and compositions with a pharmaceutically acceptable diluent, excipient, or carrier. These vaccines are effective in generating an immune response to *Plasmodium* parasites that cause malaria, and are also effective in preventing or mitigating malaria upon subsequent challenge with infectious parasites. Methods of formulating pharmaceutical compositions and vaccines are well known to those of ordinary skill in the art (see, e.g., Remington, The Science and Practice of Pharmacy 21st Edition, Hendrickson, ed. (USIP: 2005)).

Comprehended by the invention are vaccine compositions, aseptically prepared or otherwise, comprising purified, live attenuated *Plasmodium* sporozoites along with appropriate diluent and buffer. Diluents, commonly Phosphate Buffered Saline (PBS), or Normal Saline (NS), are of various buffer content pH and ionic strength. Such compositions may also include an excipient such as serum albumin, particularly human serum albumin. Serum albumin may be purified from naturally occurring sources such as human blood, or be produced by recombinant DNA or synthesis technologies. Such compositions may also include additives such as anti-oxidants e.g., ascorbic acid, sodium metabisulfite, and/or preservatives or cryopreservatives. Incorporation of the material into particulate preparations of polymeric compounds such as polylactic acid, polyglycolic acid, etc. or into liposomes may also be used. (See, e.g., Remington's Pharmaceutical Sciences, 18th Ed. (1990), Mack Publishing Co., Easton, Pa. 18042) pages 1435-1712, which are herein incorporated by reference.

In order to determine the effective amount of the vaccines, the ordinary skilled practitioner, considering the therapeutic context, age, and general health of the recipient, will be able to ascertain proper dosing. The selected dosage depends upon the desired therapeutic effect, on the route of administration, and on the duration of the treatment desired. Experiments to determine levels for dosages can be ascertained by one of ordinary skill in the art by appropriate human clinical trials in which various dosage regimens are evaluated for their capacity to elicit protection against malaria.

Disclosed vaccines and disclosed methods of using these vaccines may be useful as one component in a vaccine regimen, each component in turn comprising a discrete vaccine to be administered separately to a subject. Regimens may include a series of two or more, usually 3 to 6 inoculations of the *Plasmodium* GAP vaccines disclosed herein, at particular intervals and with the same or varying doses of immunogen. Regimens may also include other types of *Plasmodium* vaccines, so-called, prime-boost strategies. This may include attenuated sporozoites as a prime, and *Plasmodium*-related recombinant protein or proteins in adjuvant as a boost or vice versa. This may also include *Plasmodium*-related DNA vaccines or a recombinant virus, such as adenovirus, that express *Plasmodium*-related proteins, as a prime and purified, attenuated sporozoites vaccine as a boost, or vice versa. It may also include sequential or mixed immunization with attenuated *Plasmodium* species sporozoites and some form of erythrocytic stage parasites, including, killed and live attenuated. A vaccine complex comprising separate components may be referred to as a vaccine regimen, a prime/boost regimen, component vaccine, a component vaccine kit or a component vaccine package, comprising separate vaccine components. For example, a vaccine complex may comprise as a component, a vaccine comprising purified, aseptic, live attenuated sporozoites. The complex may additionally comprise one or more recombinant or synthetic subunit vaccine components, including but not limited to recombinant protein, synthetic polypeptide, DNA encoding these elements per se or functionally incorporated in recombinant virus, recombinant bacteria, or recombinant parasite. A vaccine component may also include aseptic attenuated axenic sporozoites that are allowed to develop to the early liver stage extracellularly.

*P. falciparum* strains from different parts of the world—West Africa, East Africa, SE Asia, and the like, have been described. Volunteers immunized with one strain of attenuated sporozoite exhibit protection against others strains [7]. In an embodiment, multiple isolates and/or strains of a *Plasmodium* species may be genetically altered as disclosed herein and combined in a sporozoite composition or in a vaccine formulation.

Several *Plasmodium* species are known to cause malaria in humans, predominantly *P. falciparum* and *P. vivax*. Other *Plasmodium* species cause malaria as well, including *P. malariae*, and *P. ovale*. *P. knowlesi* is also known to cause human disease. In an embodiment, two or more *Plasmodium* species are genetically altered as disclosed herein and combined in a vaccine formulation. In still other embodiments, separate components of a vaccine regimen may be derived from different species, e.g., some doses from *P. falciparum* and others from *P. vivax*.

EXAMPLES

Example 1

Materials and Methods

Experimental Animals and Parasites

Female C57BL/6J and BALB/c (12 weeks old; Janvier France) and Swiss OF1 (8 weeks old Charles River) were used.

The following reference lines of the ANKA strain of *P. berghei* were used: line cl15cy1 [18] and line 676m1cl1 (PbGFP-Luc; see RMgm-29 in www.pberghei.eu). PbGFP-Luc con expresses fusion protein of GFP and Luciferase from the eef1a promoter [19, 20].

Immunizations of Mice with *P. berghei* Sporozoites

Prior to immunization, *P. berghei* sporozoites were collected at day 21-27 after mosquito infection by hand-dissection. Salivary glands were collected in DMEM (Dulbecco's Modified Eagle Medium from GIBCO) and homogenized in a homemade glass grinder. The number of sporozoites was determined by counting in triplicate in a Bürker-Türk counting chamber using phase-contrast microscopy. BALB/c and C57BL/6J mice were immunized by intravenous injection using different numbers of GAP and γ-irradiated sporozoites (infected mosquitoes were irradiated at 16,000 rad (Gammacel 1000 137Cs) prior to dissection). BALB/c mice received one immunization and C57BL/6 mice received three immunizations with 7 day intervals. Immunized mice were monitored for blood infections by analysis of Giemsa stained films of tail blood at day 4-16 after immunization. Immunized mice were challenged at different time points after immunization by intravenous injection of $1 \times 10^4$ sporozoites from the *P. berghei* ANKA reference line cl15cy1. In each experiment, age matched naive mice were included to verify infectivity of the sporozoites used for challenge. After challenge, mice were monitored for blood infections by analysis of Giemsa stained films of tail blood at day 4-21. Pre-patency (measured in days after sporozoite inoculation) is defined as the day when a parasitemia of 0.5-2% is observed in the blood.

Mononuclear Cell Isolation From Liver, Ex Vivo Stimulation and Phenotyping

Immunized C57BL/6 mice were euthanized by isoflurane inhalation after injection of 50 i.u. of heparin. Livers were collected after perfusion with 10 ml of PBS. Cell suspensions of livers were made by pressing the organs through a 70-μm nylon cell strainer (BD LabWare). Liver cells were resuspended in 35% Percoll (GE Healthcare) and centrifuged at 800 g for 20 min. After erythrocyte lysis (5 min on ice with ACK lying buffer), hepatic mononuclear cells (HMG) were washed and re-suspended in RPM medium (Gibco, 1640) for counting. Subsequently, hepatic mononuclear cells were co-cultured in complete RPMI 1640 medium [26] in the presence of cryopreserved sporozoites ($5 \times 10^4$) or salivary glands from uninfected mosquitoes. Cells were stimulated at 37° C./5% CO for 24 hours during which Brefeldin A (Sigma) was added for the last four hours (10 μg final concentration). As a positive control to the stimulation, PMA and Ionomycin (Sigma) were added simultaneously with Brefeldin A at a final concentration of 100 ng/ml and 1.25 μg/ml respectively. Cells were harvested after 24-hours in vitro stimulation and stained for 30 min at 4° C. in cold assay buffer (PBS supplemented with 0.5% bovine serum albumin—Sigma-Aldrich) containing labeled monoclonal antibodies against CD3, CD4 and CD8 (Pacific blue-conjugated anti. CD3 (17A2), Peridinin Chlorophyll Protein (PerCP)-conjugated anti CD4 (RM4.5), Alexa fluor 700-conjugated anti CD8a (53-6.7); Biolegend (San Diego, Calif.)). Cells were fixed for 30 min at 4° C. with Fix & Perm medium A (Invitrogen) and subsequently stained for 30 min at 4° C. Fix & Perm medium B (Invitrogen) containing APC-conjugated anti-IFNγ. Flow cytometry was performed on a 9-color Cyan ADP (Beckman Coulter) and data analysis using FlowJo software (version 9.1; Tree Star). Comparisons between groups were performed by a Mann-Whitney U test using PRISM software version 5.0 (Graphpad, San Diego, Calif.). $p<0.05$ are considered statistically significant.

Parasites and Culture

For transfections the *P. falciparum* NF54 wild type strain 'working cell bank' (wcb) generated by Sanaria Inc [30] (wt) was used. Blood stages of wt, PfΔslarp-a, PfΔslarp-b, PfΔslarpΔb947 and PfΔslarpΔb9-G9 were cultured in a semi-automated culture system using standard in vitro culture conditions for *P. falciparum* and induction of gametocyte production in these cultures was performed as previously described [31-33]. Fresh human red blood cells and serum were obtained from Dutch National blood bank (Sanquin Nijmegen, NL; permission granted from donors for the use of blood products for malaria research). Cloning of transgenic parasites was performed by the method of limiting dilution in 96-well plates as described [34]. Parasites of the positive wells were transferred to the semi-automated culture system and cultured for further phenotype and genotype analyses (see below).

Generation and Genotyping of *P. falciparum* PfΔslarp and PfΔslarp Δb9 GAPs

The Pfslarp (PF11_0480; PF3D7_1147000) gene on chromosome 11 of wild-type (NF54wcb) *P. falciparum* parasites was deleted using a modified construct based on plasmid pHHT-FRT-(GFP)-Pf52 [35]. Targeting regions were generated by PCR using primers BVS179 and BVS180 for the 5' target region and primers BVS182 and BVS184 for the 3' target region. The 5' and 3' target regions were cloned into pHHT-FRT-(GFP)-Pf52 digested with BsiWI, BssHII and NcoI, XmaI respectively resulting in the plasmid pHHT-FRT-GFP-slarp. The Pfb9 (PFC0750w; PF3D7_0317100) gene on chromosome 3 of PfΔslarp-b *P. falciparum* parasites was deleted using a modified construct based on plasmid pHHT-FRT-(GFP)-Pf52 [35]. Targeting regions were generated by PCR using primers BVS84 and BVS85 for the 5' target region and primers BVS88 and BVS89 for the 3' target region. The 5' and 3' target regions were cloned into pHHT-FRT-(GFP)-Pf52 digested with NcoI, XmaI and MluI, BssHII resulting in the plasmid pHHT-FRT-GFP-b9. All DNA fragments were amplified by PCR amplification (Phusion, Finnzymes) from genomic *P. falciparum* DNA (NF54 strain) and all PCR fragments were sequenced after TOPO TA (Invitrogen) sub-cloning. Transfection of wt (NF54wcb) parasites with the plasmid pHHT-FRT-GFP-slarp and selection of mutant parasites was performed as described [35] resulting in the selection of the parasite line PfΔslarp-a. The parasite line PfΔslarp, originating from an independent transfection, was subsequently transfected to remove the drug-resistance selectable marker cassette using FLPe as described [35] and cloned resulting in the parasite clone PfΔslarp-b. Subsequent transfection of PfΔslarp-b parasites with the plasmid pHHT-FRT-GFP-b9 and selection were performed as described above resulting the parasites line PfΔslarpΔb9. The parasite line PfΔslarpΔb9 was subsequently transfected to remove the drug-resistance selectable marker cassette using FLPe and cloned as described above resulting in the cloned parasite lines PfΔslarpΔb9-F7 and PfΔslarpΔb9-G9 that are thereby free of drug-resistance markers.

Genotype analysis of PfΔslarp and PfΔslarp Δb9 parasites was performed by Expand Long range dNTPack (Roche) diagnostic PCR (LR-PCR) and Southern blot analysis. Genomic DNA of blood stages of wild-type (wt) or mutant parasites was isolated and analyzed by LR-PCR using primer pair p1, p2 (slarp) and p3,p4 (b9) (see Table 4 for primer sequences) for correct integration of the constructs in the respective Pfslarp and Pfb9 loci by double cross over integration. The LR-PCR program has an annealing step of 48° C. for 30 seconds and an elongation step of 62° C. for 10 minutes. All other PCR settings were according to manufacturer's instructions. For Southern blot analysis, genomic DNA was digested with TaqI or ReaI restriction enzymes for analysis of integration in the slarp and b9 loci respectively. Southern blot was generated by capillary transfer as described (Sambrook et al (2001) Molecular cloning: a laboratory manual. CSH Press, Cold Spring Harbor, N.Y.) and DNA was hybridized to radioactive probes specific for the targeting regions used for the generation of the mutants and generated by PCR (see above).

The presence or absence of slarp and b9 transcripts in *P. falciparum* wt and mutant sporozoites was analyzed by reverse transcriptase-PCR. Total RNA was isolated using the RNeasy mini Kit (Qiagen) from $10^6$ salivary gland sporozoites collected by dissection of mosquitoes 16 days post feeding with wt, PfΔslarp-a, PfΔslarp-b, PfΔslarpΔb9-F7 and PfΔslarpΔb9-G9 parasites. Remaining DNA was degraded using DNAseI (Invitrogen). cDNA was synthesized using the First Strand cDNA synthesis Kit for RT-PCR AMV (Roche). As a negative control for the presence of genomic DNA, reactions were performed without reverse transcriptase (RT-). PCR amplification was performed for regions of slarp using primers BVS290, BVS292 and for regions of b9 using primers BVS286 and BVS288. Positive control was performed by PCR of 18S rRNA using primers 18Sf and 18Sr.

Gametocyte, Ooocyst and Sporozoite Production of PfΔslarp and PfΔslarp Δb9 GAPs

*P. falciparum* blood stage development and gametocyte production was analyzed as described [35]. Feeding of *A. stephensi* mosquitoes with *P. falciparum*, determination of oocyst production, sporozoite production and sporozoite were performed as described [36].

Sporozoite Infectivity of PfΔslarp and PfΔslarp Δb9 GAPs

Gliding motility of sporozoites was determined as described [36-37]. Cell traversal and invasion of hepatocytes was determined in primary human hepatocytes as described [36]. Primary human hepatocytes were isolated from healthy parts of human liver fragments, which were collected during unrelated surgery in agreement with French national ethical regulations as [38].

Development of Liver Stages of PfΔslarp and PfΔslarp Δb9 GAPs in Primary Human Hepatocytes Infection of primary human hepatocytes with sporozoites was performed as described [36]. For analysis of parasite development by immunofluorescence, parasites were stained with the following primary antibodies: anti-HSP70 (PF3D7_0930300 [39]; anti-CSP (PF3D7_0304600; 3SP2). Anti-mouse secondary antibodies, conjugated to Alexa-488 or Alexa-594 (Invitrogen) were used for visualization.

Development of Liver Stages of PfΔslarp Δb9 GAP in Chimeric Mice Engrafted With Human Liver Tissue Human liver-uPA-SCID mice (chimeric mice) were produced as previously described [40]. Briefly, within two weeks after birth homozygous uPA$^{+/+}$-SCID mice [41] were transplanted with approximately $10^6$ cryopreserved primary human hepatocytes obtained from a single donor (BD Biosciences, Erembodegem, Belgium). To evaluate successful engraftment, human albumin was quantified in mouse plasma with an in-house ELISA (Bethyl Laboratories Inc., Montgomery, Tex.). The study protocol was approved by the animal ethics committee of the Faculty of Medicine and Health Sciences of the Ghent University. Homozygous uPA-HuHep (n=10) and non-human hepatocyte transplanted uPA (control, n=2)) mice were intravenously injected with $10^6$ fresh isolated PfΔslarp Δb9-G9 or as a control wt sporozoites. At days 1 and 5 livers were removed and each liver was divided in 12 parts. From each part DNA was extracted to assess the parasite load by Pf18S rRNA qPCR [42] and to assess the number of human and mouse hepatocytes by Multiplex qPCR PTGER2 analysis.

Example 2

Generation and Characterization of *P. berghei* Δb9 and Δb9Δslarp Parasites

Generation of *P. berghei* Mutants

Figure 8:
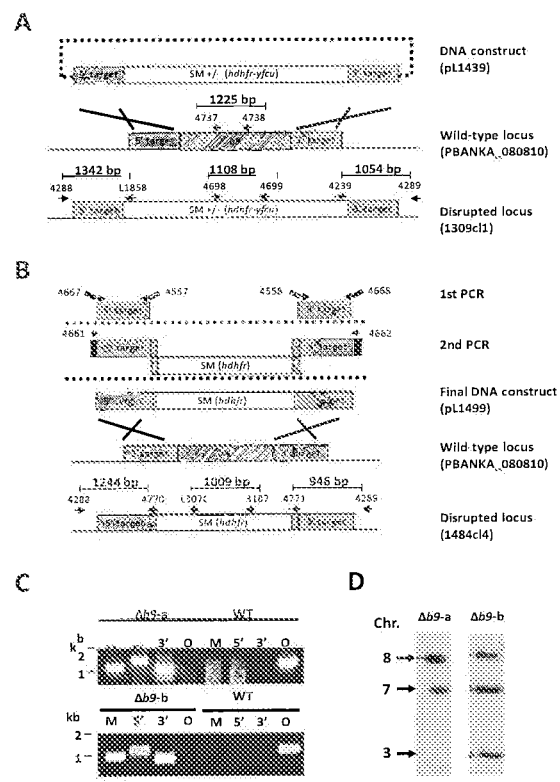

To disrupt the *P. berghei* b9 gene (PBANKA_980810) two different gene deletion constructs were constructed. The first construct used the standard targeting DNA construct, pL0037 (MR4; www.MR4.org), which contains the positive/negative selectable marker cassette hdhfr/yfcu. Target sequences for integration of the construct by double cross-over homologous recombination were PCR amplified from *P. berghei* genomic DNA (cl15cy1) using primers (Table 4) which are specific for the 5' and 3' end of b9, respectively. The PCR-amplified target sequences were cloned either upstream or downstream of the SM of plasmid pL0037 resulting in plasmid pL1439 (FIG. 8). Prior to transfection the DNA-construct pL1439 was linearized with Asp 718 and Xma I. Using this construct the mutant Δb9-a (1309cl1) was generated in the cl15cy1 reference line using standard methods of transfection and positive selection with pyrimethamine [18] (See FIG. 8A-D).

The second construct for disruption of the b9 gene, pL1499, was generated using the adapted 'Anchor-tagging' PCR-based method as described [14] (See FIG. 8A-D). The two targeting fragments (0.8 kb) of b9 were amplified using genomic DNA (parasite cl15cy1) as template with the primer pairs 4667/4557 (5'target sequence) and 4558/4668 (3'target sequence). See Table 4 for the sequence of the primers. Using this PCR-based targeting construct the mutant Δb9-b (1481cl4) was generated in PbGFP-Luc con reference line using standard methods of transfection and positive selection with pyrimethamine (See FIG. 8A-D).

To disrupt the *P. berghei* slarp gene (PBANKA_090210) a construct was generated using the adapted 'Anchor-tagging' PCR-based method as described [14] (See FIG. 10A-13). The two targeting fragments (1195 bp and 823 bp) of slarp were amplified using genomic DNA (parasite line cl15cy1) as template with the primer pairs 5960/5961 (5'target sequence) and 5962/5963 (3'target sequence). See Table 4 for the sequence of the primers. Using this PCR-based targeting construct (pL1740) the mutant Δslarp-a (1839cl3) was generated in the PbGFP-on reference line using standard methods of transfection and positive selection with pyrimethamine (See FIG. 10A-B).

To generate a selectable marker-free mutant PbΔb9Δsm the drug-selectable marker cassette was removed from mutant PbΔb9-a using the standard procedure of negative selection [14] (See FIG. 11A-B). The resulting cloned mutant (Δb9Δsm; 1309cl1m0cl2), which contains a disrupted b9 gene and is drug-selectable marker free, was used for deleting the slarp (PBANKA_090210) gene. To delete the slarp gene the gene deletion construct pL1740 was used as described above. Using this construct the mutant PbΔb9Δslarp (line 1844cl1) was generated in the Δb9Δsm line using standard methods of transfection and positive selection with pyrimethamine (See FIG. 12A-B). Correct integration of the constructs into the genome of mutant parasites was analyzed by diagnostic PCR-analysis and Southern analysis of PFG-separated chromosomes as shown in FIGS. 8C-D. PFG-separated chromosomes were hybridized with a probe recognizing hdhfr or the 3'-UTR dhfr/ts of *P. berghei* [18]. Absence of transcripts of the targeted genes in sporozoites was analyzed by reverse transcriptase-PCR. Total RNA was purified from salivary gland sporozoites using TRIzol reagent (Invitrogen) and prepared according to manufactures specifications. Purified RNA was then treated with RQ1 DNase (Promega). Reverse transcription was performed using the Super Script III RT (Invitrogen) as previously described [13]. cDNA was used as template for PCR amplification with control and gene specific primers that are listed in Table 4.

Analysis of blood and mosquito stage development of *P. berghei* mutant parasites: The *P. berghei* mutants were maintained in Swiss mice. The multiplication rate of blood stages and gametocyte production were determined during the cloning procedure [18] and were not different from parasites of the reference ANKA lines. Feeding of *A. ste-phensi* mosquitoes and determination of oocyst production was performed as described [21]. *P. berghei* sporozoite production was determined by collection of salivary glands at day 21 after infection by hand-dissection. Salivary glands were collected in DMEM (Dulbecco's Modified Eagle Medium from GIBCO) and homogenized in a homemade glass grinder. The number of sporozoites was determined by counting the numbers of sporozoites of 10 salivary glands in triplicate in a Bürker-Türk counting chamber using phase-contrast microscopy.

Analysis of *P. berghei* sporozoite motility, hepatocyte traversal, invasion and development: Gliding motility of *P. berghei* sporozoites was determined in assays that were performed on anti-*P. berghei* circumsporozoite antibody (3D11, monoclonal mouse antibody 10 μg/ml) pre-coated Labtek slides (Nurc, NL) to which $2 \times 10^4$ sporozoites were added [13]. After 30 minutes of incubation at 37° C. sporozoites were fixed with 4% PFA and after washing with PBS, the sporozoites and the trails ('gliding circles') were stained with anti-CSP-antibody (3D11 [22]) conjugated to Alexa 488 (Dylight 488 antibody labeling kit; Thermo Scientific, NL). Slides were mounted with Fluoromount-G (SouthernBiotech, NL) and 'gliding circles' were analyzed using a Leica DMR fluorescence microscope at 1000× magnification.

*P. berghei* sporozoite hepatocyte traversal was determined in assays as described previously [23]. Briefly, human liver hepatoma cells (Huh-7) were suspended in 1 ml of 'complete' DMEM (DMEM from Gibco, supplemented with 10% FCS, 1% penicillin/streptomycin and 1% Glutamax) and were plated in 24 well plates ($10^5$ cells/ml). After the Huh7 monolayers were >80% confluent, $10^5$ sporozoites were added with the addition of FITC- or Alexa-647-labeled dextran (Invitrogen, NL). No sporozoites were added to the negative control wells. FACS analysis of dextran-positive cells was performed on a total $25 \times 10^3$ cells per well (each experiment was performed in triplicate wells) using a FACScalibur flow cytometer (Becton Dickinson, NL).

Invasion of hepatocytes in vitro by *P. berghei* sporozoites was determined by addition of $5 \times 10^4$ sporozoites to a monolayer of Huh7 cells. After the addition of sporozoites, cultures were centrifuged for 10 minutes at 1800G (Eppendorf centrifuge 5810 R) and then returned to the 37° C. incubator. After 2-3 hours wells were washed 3 times with PBS to remove non-invaded sporozoites. Cells were fixed with 4% paraformaldehyde (PFA) for 10 min and extracellular (non-invaded) parasites were stained with anti-CS-antibody (3D11) and conjugated with Alexa 594 antibody (Dylight 594 antibody labeling kit; Thermo Scientific, NL). After permeabilization with 0.1% Triton-X-100 for 10 minutes and blocking with 10% FCS it PBS for 20 minutes, intracellular sporozoites were stained with anti-CS-antibody (3D11) conjugated with Alexa 488 antibody (Dylight 488 antibody labeling kit; Thermo Scientific, NL). Nuclei were stained with DAPI. Analysis and counting of stained intracellular and extracellular parasites were performed using a Leica DMR fluorescence microscope at 1000× magnification. All quantitative phenotypical assays with *P. berghei* parasite lines were performed in triplicate.

*P. berghei* sporozoites development was determined in cultures of Huh-7 cells. Sporozoites ($5 \times 10^4$) were added to a monolayer of Huh7 cells on coverslips in 24 well plates (with a confluency of 80-90%) in 'complete' DMEM. At different time points after infection, cells were fixed with paraformaldehyde 4%, permeabilized with Triton-X-100, 0.1%, blocked with 10% FCS in PBS, and subsequently stained with a primary (anti-PbEXP1 [24]; anti-PbHSP70

[13]; anti-PbUIS-4 and anti-MSP-1 (MRA-78 from MR4; www.MR4.org)) and secondary antibody, for 2 h and 1 h respectively. Anti-mouse, -chicken and -rabbit secondary antibodies, conjugated to Alexa-488 and Alexa-594, were used for visualization (Invitrogen). Nuclei were stained with DAPI. Cells were mounted in Fluoromount-G and examined using a Leica DMR fluorescence microscope at 1000× magnification.

Analysis of P. berghei sporozoite infectivity and in vivo imaging of liver stage development in mice C57BL/6 mice were inoculated with sporozoites by intravenous injection of different sporozoite numbers, ranging from $1 \times 10^4$-$5 \times 10^5$, Blood stage infections were monitored by analysis of Giemsa-stained thin smears of tail blood collected on day 4-18 after inoculation of sporozoites. Pre-patency (measured in days after sporozoite inoculation) is defined as the day when a parasitemia of 0.5-2% is observed in the blood.

Liver stage development in live mice was monitored by real-time in vivo imaging of liver stages as described previously [25] with minor adaptations. Briefly, animals were anesthetized using the isoflurane-anesthesia system, their abdomens were shaved and D-luciferin dissolved in PBS (150 mg/kg; Caliper Life Science, Belgium) was injected SC (in the neck). Animals were kept anesthetized during the measurements, which were performed 4 minutes after the injection of D-luciferin. Bioluminescence imaging was acquired with a 10 cm field of view, medium binning factor and an exposure time of 180 seconds. The color scale limits were set automatically and the quantitative analysis of bioluminescence was performed by measuring the luminescence signal intensity using the region of interest (ROI) settings of the Living Image 3.2 software. The ROI was set to measure the abdominal area at the location of the liver. ROI measurements are expressed in total flux of photons.

Results From Characterization of P. berghei Δb9 Parasites

P. berghei Δb9 mutants were generated, using standard methods of targeted gene-deletion by integrating constructs through double cross-over homologous recombination (FIG. 8A-B). Two independent b9 mutants were generated in the P. berghei ANKA reference lines cl15cy1 and PbGFP-Luc$_{con}$. The latter line is a reporter line which expresses the fusion protein GFP-Luciferase from the consititutive eef1a promoter, thereby allowing analysis of liver stage development in live mice by in vivo imaging [25]. Correct deletion of the genes in cloned mutants was confirmed by Southern analysis of FIGE-separated chromosomes and diagnostic PCR (FIG. 8C-D).

Figure 1:
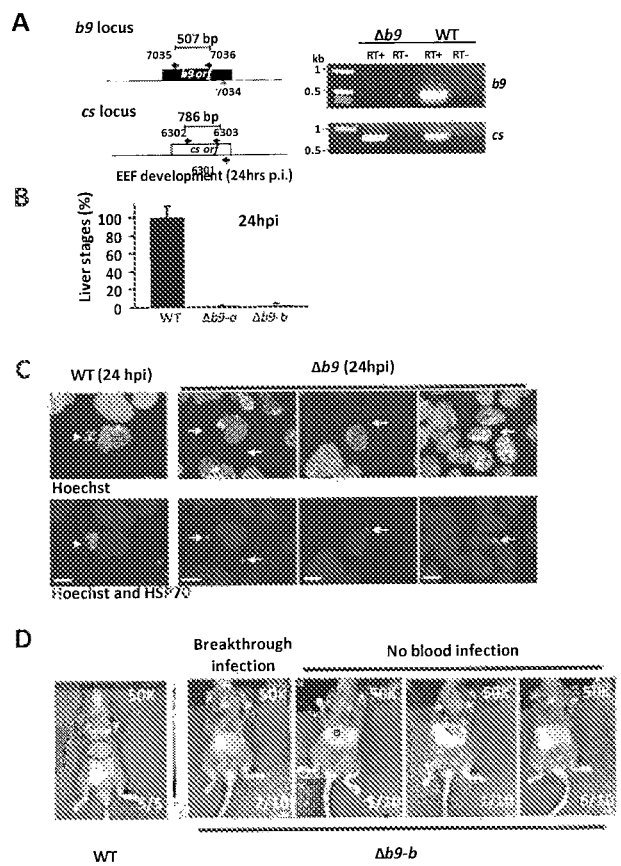
FIG. 1A-D: Characterization of P. berghei Δb9 liver stage development. (A) qRT-PCR analysis showing absence of b9 transcripts in sporozoites of Δb9 mutants and wild-type. PCR amplification using purified sporozoite RNA was performed either in the presence or absence of reverse transcriptase (RT+ or RT−, respectively) using the primers as shown in the left panel (see Table 4 for the sequence of the primers). The P. berghei circumsporozoite protein gene (cs) was used as a positive control. (B) Number of Δb9-a and Δb9-b mutant parasites in a Huh-7 infected culture at 24 hours post infection as compared to wild-type. (C) IFA of wild type and Δb9 infected huh-7 cells stained with Hoechst-33342 (upper panel) and anti-HSP70 (red: lower panel) at 24 hours post infection. (D) Real time in vivo imaging of luciferase-expressing liver-stage parasites in C57BL/6 mice at 42 hpi. C57BL/6 mice were IV injected with either $5 \times 10^4$ Pb-GFPLuc$_{con}$ sporozoites (n=5) resulting in a full liver infection (left figure: representative image of WT infected mice), or with $5 \times 10^4$ Pb Δb9-b sporozoites (n=10) (right panel). All mice infected with WT parasites became patent with a blood stage parasitemia. Out of the 10 C57BL/6 mice that were infected with 50K Δb9-b sporozoites 6 remained negative for any luminescent signal and did not get infected by a blood stage parasitemia. Out of the other 4 mice which showed individual spots overlaying the liver (possibly individual infected hepatocytes) 2 became patent with a delayed blood stage infection.

The Δb9 mutants had normal blood-stage development, and the production of oocysts and sporozoites was comparable to those of wild type parasites (Table 5). In addition, salivary gland sporozoites exhibited normal levels of gliding motility, hepatocyte traversal and wild-type levels of hepatocyte invasion (Table 5). In WT parasites b9 transcripts were clearly present in salivary gland sporozoites by RT-PCR analysis whereas b9 transcripts were, as expected, absent in PbΔb9 mutants (FIG. 1A). When Swiss or BALB/c mice were infected by intravenous inoculation of $1 \times 10^4$ or $5 \times 10^4$ Δb9 sporozoites none of these mice developed a blood stage infection (Table 6), indicating an important role of b9 in the liver. Next, it was determined whether the PbΔb9 GAP was capable of eliciting long lasting and sterile protection against homologous challenge by immunizing mice with different dosages. Immunization of BALB/c and C57BL/6 mice with PbΔb9 parasites induced sterile protection against challenge with wild type parasites (Table 1). A single dose of as few as 1000 sporozoites was sufficient to induce immunity in BALB/c mice. Immunization of C57BL/6 mice by a prime and boost regimen (50K/20K/20K) resulted in sterile protection in approximately 50% of the mice for up to 1 year post immunization. A 1 year re-challenge of mice that were already challenged at 6 months increased the level of protection to 100%. The PbΔb9 thereby elicits at least the same level of protection as observed for mutants lacking either p52 or p52&p36 [13, 27, 28].

Despite this good protective efficacy, when C57BL/6 mice were infected with a sporozoite dose of $5 \times 10^4$ PbΔb9 sporozoites, 10-20% of the mice developed breakthrough blood infections (Table 6). In these mice, the pre-patent period was delayed with 2-3 days, indicating that blood infections arose from a few infected hepatocytes. Genotyping of parasites derived from the breakthrough blood infections confirmed the PbΔb9 genotype of these parasites (data not shown).

Figure 9:
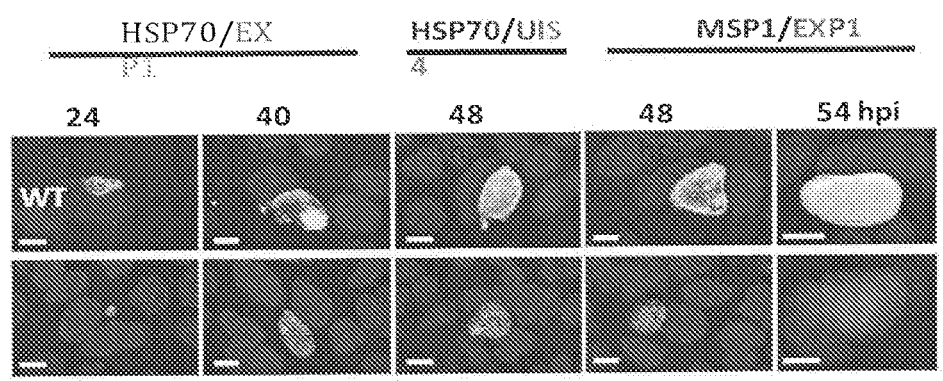

The development of PbΔb9 parasites was analyzed in more detail both in cultured hepatocytes and in the liver of infected C57BL/6 mice. Quantitative analyses of PbΔb9-infected hepatocytes by fluorescence microscopy demonstrated that Δb9 parasites arrest early after invasion of hepatocytes. At 24hpi most parasites had disappeared from the cultures and a few small forms were observed with a size similar to that of liver stages 1-5 hpi of hepatocytes (FIG. 1B,C). Analysis of PbΔb9 parasites in the liver, using real time in vivo imaging of luciferase expressing parasites, confirmed the growth-arrest phenotype observed in cultured hepatocytes. In six out of ten C57BL/6 mice infected $5 \times 10^4$ PbΔb9 sporozoites, development of liver stages was not observed, as demonstrated by the complete absence of luminescence signals in the liver at 42 hpi. At this time point all livers from all control mice infected with luciferase-expressing WT parasites were strongly luminescent (FIG. 1D). None of the luminescent-negative mice developed a blood stage infection. In four PbΔb9-infected mice a weak luminescent signal was detected which was confined to only a few (1-2) small spots (FIG. 1D) but only two of these mice developed a blood infection with a pre-patent period of 8 to 9 days (Table 6). Combined, these analyses demonstrate that PbΔb9 has an important role during early liver stage development. However, in the absence of the 139 protein, liver stage development can occur, as shown by the occurrence of breakthrough blood infections in 10-20% of the mice (albeit only after high intravenous PbΔb9 sporozoite inoculation). On close examination of in vitro hepatocyte culture, it was determined that P. berghei Δb9 parasites were capable of developing into infectious merozoites in the absence of an apparent PVM, as indicated by the lack of a peripheral EXP-1 and UIS-4 staining (FIG. 9).

Results From Characterization of P. berghei Δb9Δslarp Parasites

Figure 2:
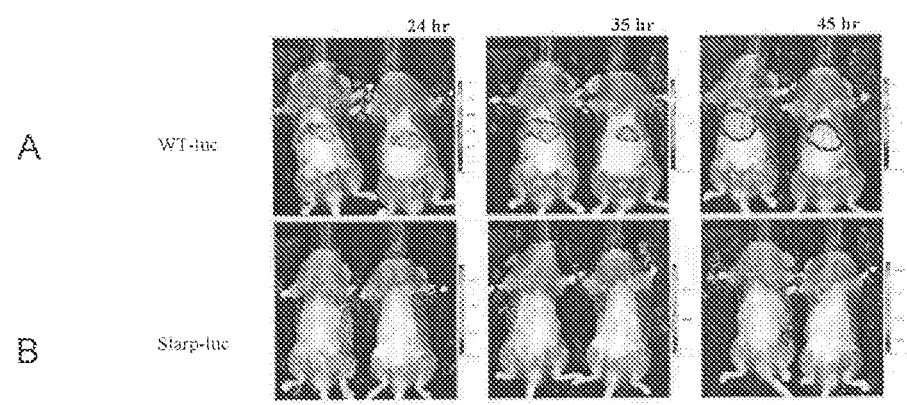
FIG. 2A-B: Real-time in vivo imaging of Δslarp-luc parasite liver development. Real-time in vivo imaging of luciferase-expressing liver-stage parasites in C57BL/6 mice at 30, 35 and 44 hours post infection. C7BL/6 mice were injected IV with either $5 \times 10^4$ Pb-GFPLuc$_{con}$ sporozoites (n=5) RESULTING IN FULL LIVER INFECTION (Upper panel (A): representative image of WT infected mice), or with $5 \times 10^4$ Pb Δslarp-a (n=5) (Lower panel (B): representative image of Δslarp-a infected mice).

In our pursuit of a fully arresting GAP, without breakthrough, a P. berghei multiple attenuated Δb9Δslarp GAP was generated using standard methods of gene targeting by double cross-over integration (FIG. 12A-B; Table 4). Moreover a Δslarp mutant was generated in the P. berghei reference reporter line, PbGFP-Luc$_{con}$ (FIG. 10A-B; Table 4). PbΔslarp and PbΔb9Δslarp mutants showed normal blood-stage development (data not shown) and produced oocyst and sporozoite numbers comparable to those of WT parasites (Table 7). Salivary gland sporozoites demonstrated normal gliding motility and hepatocyte traversal, and sporozoites of all mutants were able to invade hepatocytes at WT levels (Table 7). PbΔb9Δslarp parasites had an early growth arrest in hepatocytes as determined by immunofluorescent microscopy of infected single Δb9Δslarp parasite developed and underwent multiple nuclear replications in the hepatocytes (data not shown). Infection of BALB/c and C57BL/6 mice with Huh-7 cells, was similar to the previously reported PbΔslarp [15] and that of PbΔb9 GAP (data not shown). In contrast to *P. berghei* Δp52p36 [14] and Δb9 parasites, high numbers ($5 \times 10^4$ and $5 \times 10^5$ respectively) of PbΔslarp and Δb9Δslarp sporozoites did not result in a breakthrough blood infection (Table 8). Moreover, infection of C57BL/6 mice with $5 \times 10^5$ Δslarp sporozoites did not result in any detectable liver stage development as determined by in vivo real-time imaging (FIG. 2A-B). Thus, both PbΔslarp and PbΔb9Δslarp completely arrested in early liver stage development, but retained the capacity for full development of the asexual and sexual erythrocytic and mosquito stages of the life cycle.

Example 3

Immunization of Mice with *P. berghei* Δb9Δslarp Induces Sterile and Long-Lasting Protection Having verified that the PbΔb9Δslarp GAP did not develop in mature liver stage parasites, its protective efficacy following immunization was tested. Similar to immunization with PbΔb9 parasites, PbΔb9Δslarp induced sterile protection against challenge with wild type parasites at low doses in BALB/c mice (Table 2). Moreover, low dose PbΔb9Δslarp immunization of C57BL/6 mice (a more stringent murine model—Annoura, T et al (2012) Assessing the Adequacy of Attenuation of Genetically Modified Malaria Parasite Vaccine Candidates: Vaccine 30:2662-2670) resulted in a conferred level of protection, similar to that of γ-irradiated sporozoite immunization (Table 2). These data were affirmed by the cellular immune response in C57BL/6 mice immunized with Δb9Δslarp or γ-irradiated sporozoites, at as late as 70 days post challenge (FIG. 13). Stimulation of hepatic mononuclear cells from mice immunized with a dose regimen of 10K/10K/10K and 1K/1K/1K resulted in significantly higher IFNγ responses of CD8+ T cells, ($p < 0.02$). Within each dose regimen, no significant difference could be observed between mice receiving a Δb9Δslarp or γ-irradiated sporozoite immunization.

The majority of mice receiving a low immunization dose (10K/10K/10K spz) were protected upon re-challenge after 180 days. More importantly, mice immunized with Δb9Δslarp or with γ-irradiated sporozoites showed high levels of protection after a first time challenge at 180 days post immunization (Table 2). In summary, the multiple attenuated *P. berghei* GAP Δb9Δslarp does not develop into mature liver stage parasites and induces long-lasting sterile protection against a wild-type challenge. Immunization of BALB/c and C57BL/6 mice with the single gene deleted PbΔslarp parasite resulted in sterile and long-lasting protection, not significantly different from immunization with PbΔb9Δslarp (Table 9).

Example 4

Generation and Genotyping of *P. falciparum* PfΔslarp and PfΔslarp Δb9 GAPs

Figure 3:
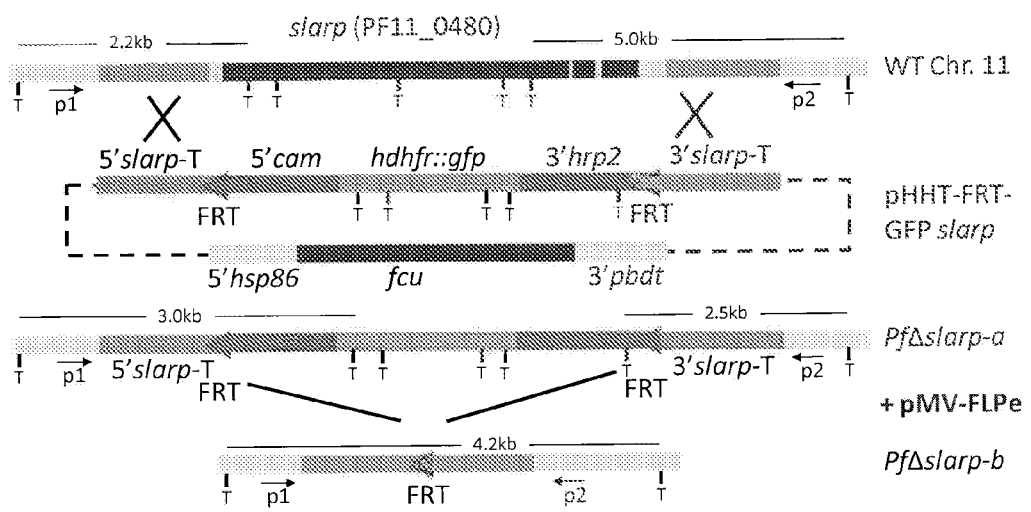
FIG. 3A-B: Consecutive gene deletion of slarp and b9 in P. falciparum. Schematic representation of the genomic loci of (A) slarp (PF11_0480) on chromosome 11 (Chr. 11) and (B) b9 (PFC_0750w) on chromosome 3 (Chr. 3) of wild-type (wt; NF54wcb), PfΔslarp and PfΔslarpΔb9 gene deletion mutants before (PfΔslarp a and PfΔslarpΔb9) and after the FLPe mediated removal (REF) of the hdhfr::gfp resistance marker (PfΔslarp-b and PfΔslarpΔb9 clones F7/G9) respectively. The constructs for the targeted deletion of slarp (pHHT-FRT-GFP slarp) and b9 (pHHT-FRT-GFP-B9) contain two FRT sequences (red triangles) that are recognized by FLPe. P1, P2 and P3, P4 primer pairs for LR-PCR analysis of slarp and b9 loci respectively; T (TaqI) and R (RcaI): restriction sites used for Southern blot analysis and sizes of restriction fragments are indicated; cam: calmodulin; hrp: histidine rich protein; hsp: heatshock protein; fcu: cytosine deaminase/uracil phosphoribosyl-transferase; hdhfr::gfp: human dihydrofolate reductase fusion with green fluorescent protein; pbdt: P. berghei dhfr terminator.
Figure 3:
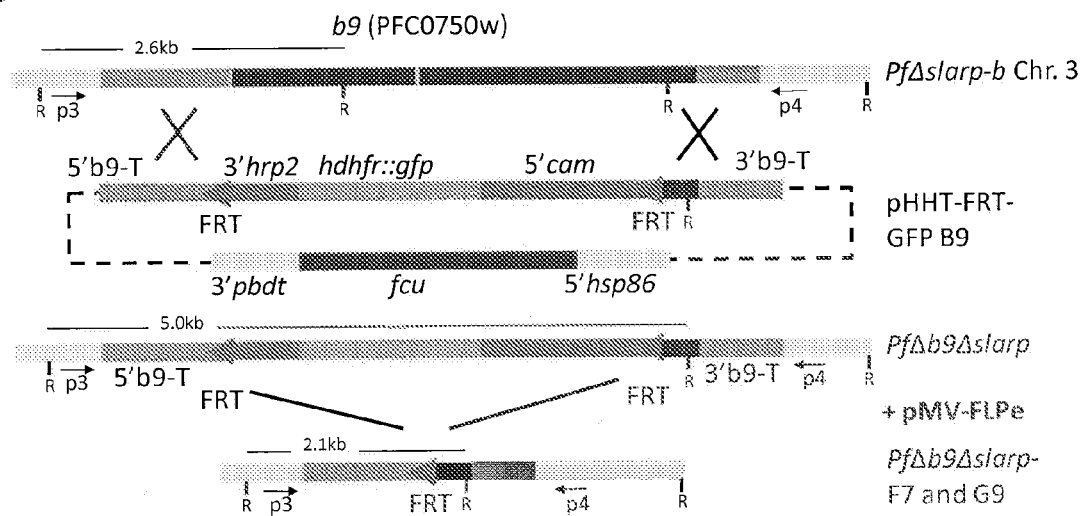
Figure 4:
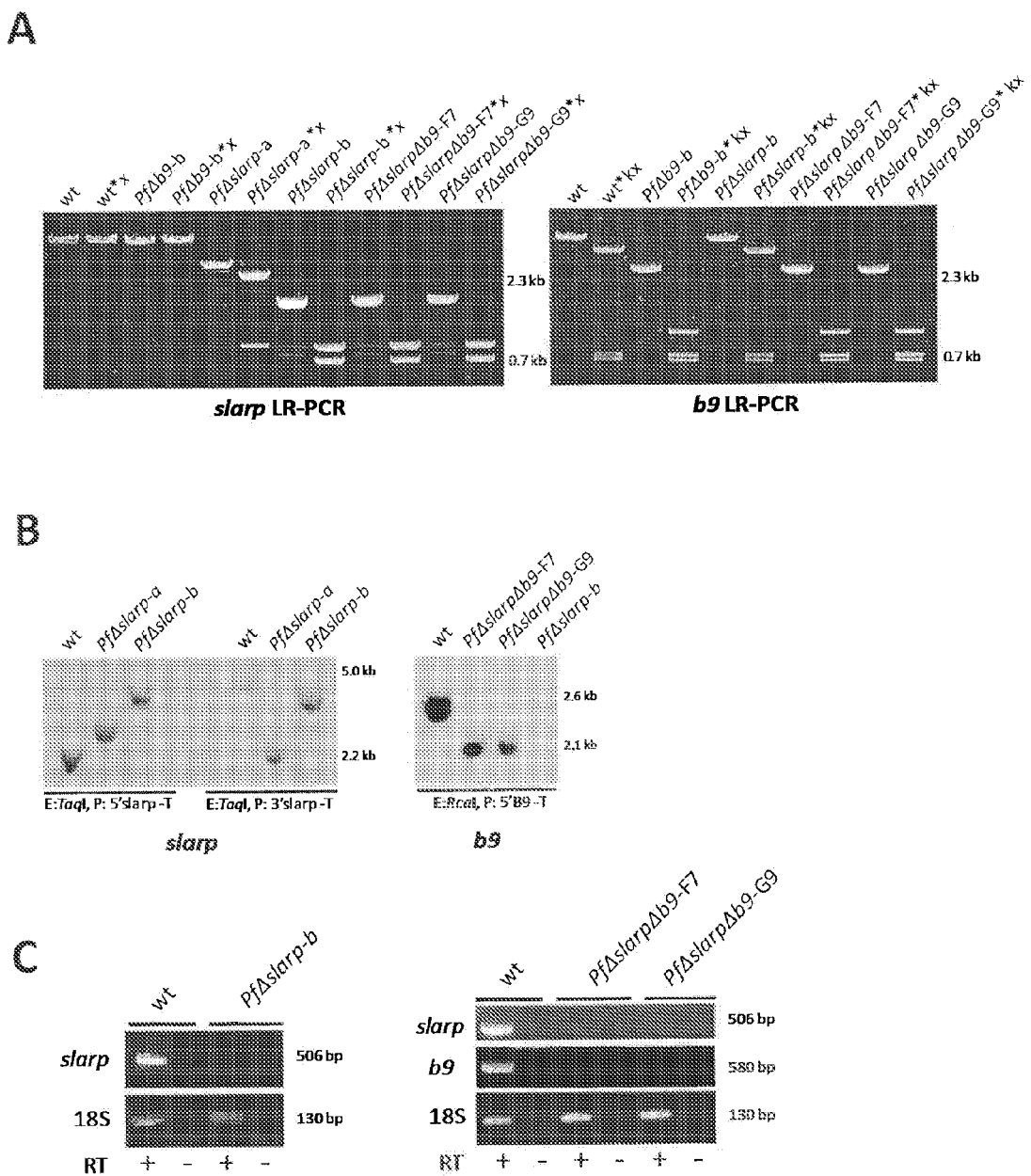
FIG. 4A-C: Genotype analysis of the generated PfΔslarp and PfΔslarpΔb9 parasites. (A) Long range PCR analysis of genomic DNA from WT, PfΔslarp and PfΔslarpΔb9 asexual parasites confirms the slarp gene deletion and consecutive gene deletions of both slarp and b9 respectively and subsequent removal of the hdhfr::gfp resistance marker. The PCR products are generated using primers P1, P2 for slarp and P3, P4 for b9 (see A and B respectively; for primer sequences see primer Table 4) and PCR products are also digested with restriction enzymes x (XmaI) and kx (KpnI/XcmI) respectively for confirmation (i.e. slarp LR-PCR product sizes: WT, 12 kb, is undigested; Δslarp-a, 5.4 kb is digested into 1.3 kb and 4.0 kb fragments, Δslarp-b, 2.4 kb is digested into 1.3 kb and 1.1 kb fragments. b9 LR-PCR product sizes: WT, 5.5 kb, is digested into 756 bp, 793 bp and 4.0 kb fragments; Δb9-b, 2.6 kb is digested into 756 bp, 793 bp and 1.1 kb fragments). (B) Southern analysis of restricted genomic DNA from WT, PfΔslarp-a, PfΔslarp-b, PfΔslarpΔb9-F7 and PfΔslarpΔb9-G9 asexual parasites. DNA was digested with restriction enzyme (E: TaqI) and probed with the 5' slarp targeting region (P: 5' slarp-T; see A) on the left side of the slarp Southern or probed with the 3' slarp targeting region (P: 3' slarp-T; see A) on the right side of the slarp panel. For analysis of the b9 integration DNA was digested with restriction enzymes (E: RcaI) and probed with the 5'b9 targeting region (P: 5' b9-T; see A) on the right panel. The expected fragment sizes are indicated in panel A. (C) RT-PCR analysis showing absence of b9 and slarp transcripts in P. falciparum PfΔslarp-a, PfΔslarp-b, PfΔslarpΔb9-F7 and PfΔslarpΔb9-G9 mutant sporozoites. PCR amplification using purified sporozoite RNA was performed either in the presence or absence of reverse transcriptase (RT+ or RT−, respectively) and generated the expected 506 bp and 580 bp fragments for slarp and b9 respectively, the positive control was performed by PCR of 18S rRNA using primers 18Sf/18Sr (for primer sequences see primer Table 4) and generated the expected 130 bp fragment.

Two independent GAP's lacking slarp gene (Pf Δslarp-a and Pf Δslarp-b; both lacking expression of SLARP [PF3D7_1147000]) and two independent GAPs lacking both b9 and slarp (Pf ΔslarpΔb9-F7 and Pf ΔslarpΔb9-G9; both lacking expression of B9 [PF3D7_0317100] and SLARP [PF3D7_1147000]) were generated using genetic modification technologies that have been previously described [35, 44]. These gene deletion mutants were created in the 'working cell bank' (wcb) of the wild type *P. falciparum* NF54 strain (Ponnudurai et al., 1981), generated by Sanaria Inc. Pf Δslarp-b and Pf ΔslarpΔb9-G9 are free of a drug resistance marker which has been removed using the FLp-recombinase system described in Van Schaijk et. al. [35]. In FIG. 3A-B, the schematic representation of the constructs, the gene loci, and genomic loci of the 4 different GAPs are shown. Diagnostic PCR and Southern analysis of genomic DNA confirmed the correct integration of the constructs in the 4 different GAP (FIG. 4A,B). RT-PCR analysis using RNA derived from purified sporozoites shows the absence of slarp and b9 transcripts in the Pf ΔslarpΔb9-F7 and Pf ΔslarpΔb9-G9 GAP, confirming correct deletion of the slarp and b9 genes (FIG. 4C).

Example 5

Gametocyte, Oocyst and Sporozoite Production of PfΔslarp and PfΔslarpΔb9 GAPs

Asexual blood stage development of all 4 GAPs in vitro was comparable to wild type NF54wcb (wt) parasites (data not shown) and gametocyte production in vitro was also comparable to those of wt parasites (Table 3). In addition, *A. stephensi* mosquitoes infected with the different GAPs produced oocysts and salivary gland sporozoites in comparable numbers to *A. stephensi* mosquitoes infected with wt parasites (Table 3).

Example 6

Sporozoite Infectivity of PfΔslarp and PfΔslarpΔb9 GAPs

Figure 5:
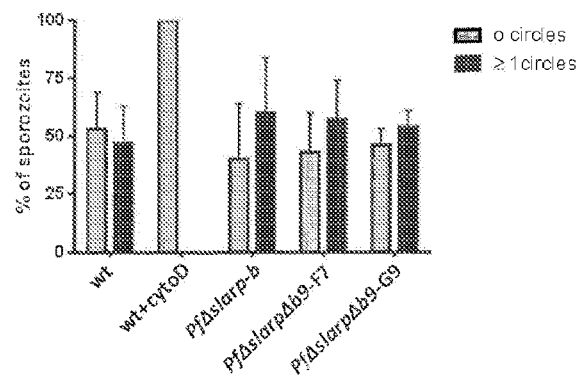
FIG. 5A-C: Gliding motility, cell traversal, and in vitro invasion of GAP P. falciparum. (A) Gliding motility of P.
Figure 5:
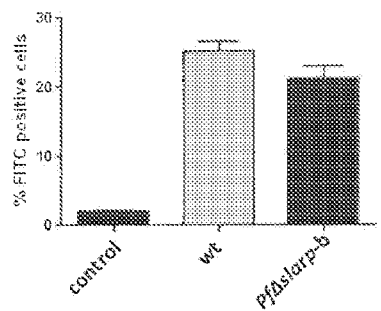
Figure 5:
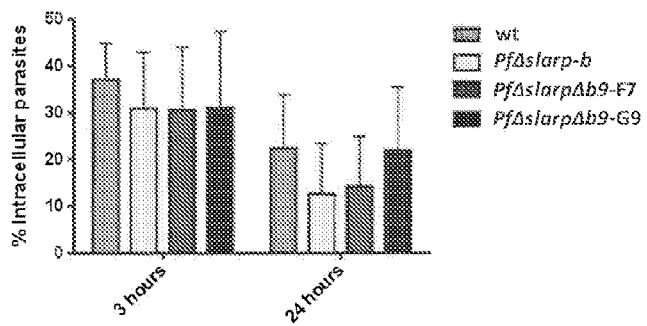

Salivary gland sporozoites of PfΔslarp and PfΔslarpΔb9 GAPs exhibited wild type gliding motility (FIG. 5A). The ability of sporozoites to traverse through cultured human hepatocytes was analyzed for PfΔslarp-b and PfΔslarpΔb9 and was the same as wt sporozoite traversal (FIG. 5B). In addition to normal gliding motility and cell traversal, sporozoites invasion of primary human hepatocytes by PfΔslarp and PfΔslarpΔb9 GAPs was also comparable to wt sporozoites invasion (FIG. 5C).

Example 7

Development of Liver Stages of PfΔslarp and PfΔslarpΔb9 in Primary Human Hepatocytes The development of PfΔslarp parasites in primary human hepatocytes was observed at 3, 24 and 48 hours post infection (hpi), as shown by fluorescence microscopy of intracellular parasites after staining with anti-CS antibodies (FIGS. 5A-C and 6A-B). At 3 and 24 hpi the number of intracellular PfΔslarp-b parasites was not significantly different from wild type parasites (FIG. 5C) whereas at 48 hpi the number of PfΔslarp-b parasites was more then 10-fold reduced when compared to wt infection (FIG. 6A-B). No intracellular PfΔslarp parasites were detected, by fluorescence microscopy after staining with anti-HSP70 antibodies, from day 3 to day 7 post sporozoite infection (FIG. 6A-B). At 3 and 24 hpi PfΔslarp-b parasites were morphologically identical (by light/fluorescence-microscopy) to wt parasites at the same point of development (data not shown).

In primary human hepatocytes, intracellular PfΔb9Δslarp parasites at 3 and 24 hpi were observed, as shown by fluorescence microscopy of intracellular parasites after staining with anti-CS antibodies (FIGS. 5A-C and 6A-B), which had the same morphology as wt parasites at the same point of development (data not shown). After 24 hpi, intracellular PfΔb9Δslarp parasites were not detected, up to day 7 post sporozoite infection of the hepatocytes (FIG. 6A-B), These analyses demonstrate that *P. falciparum* parasites that lack expression of either only SLARP or both B9 and SLARP abort liver-stage development relatively soon after invasion of hepatocytes, a phenotype that is comparable to the early growth arrest observed in *P. berghei* Δb9 and *P. falciparum* Δb9 GAPs and the *P. berghei* Δslarp and *P. yoelii* Δsap1 GAPs [45, 46]. Extensive analyses by fluorescence microscopy of all hepatocyte cultures at day 3 to 7 after PfΔslarp or PfΔslarp Δb9 sporozoites, did not reveal the presence of any replicating parasites (as observed in Pb Δb9 and Pf Δb9 GAP (data not shown).

The absence of such replicating forms is in agreement with complete attenuation of the GAPs Pb Δslarp and Py Δsap1 where no developing liver stages could be observed and therefore resulted in no breakthrough blood infections even after the inoculation of high doses of sporozoites intravenously GAPs [45, 46].

Example 8

Development of Liver Stages PfΔslarp Δb9 GAP in Chimeric Mice Engrafted with Human Liver Tissue Using the methods of Lootens, et al. [69], -uPA(+/+)-SCID mice were transplanted with primary human hepatocytes (chimeric mice), as described previously [41]. Chimeric mice (n=6) and nonchimeric mice (n=4) without transplanted human hepatocytes were used. The nonchimeric mice served as a control group. Chimeric uPA mice engrafted with human hepatocyte tissue (uPA HuHEP) were infected with $10^6$ wt or PfΔslarpΔb9-G9 sporozoites by intravenous inoculation. As controls, 2 uPA mice (not engrafted with human hepatocytes) were infected with sporozoites as described for the uPA HuHEP mice. Either at 24 hours or at 5 days after sporozoite infection, livers were collected from the mice and the presence of parasites determined by qRT-PCR of the parasite-specific 18S ribosomal RNA. At 24 hours 2/2 wt infected mice and 1/2 PfΔslarpΔb9-G9 infected mice showed significantly more parasite 18S rRNA in their liver sections as compared to the livers of the uPA control mice, demonstrating successful sporozoite infection in human hepatocytes (FIG. 7A-B). The lower signal of PfΔslarpΔb9-G9 parasites at day 1 after infection compared to wt parasites may be a reflection of decreased transcription as a result of the early attenuation phenotype of PfΔslarpΔb9-G9 parasites. At day 5 after infection, wt-infected mice (3 out of 3) exhibit a strong increase in parasite 18S rRNA demonstrating *P. falciparum* liver stage development. In contrast, mice infected with PfΔslarpΔb9 sporozoites had no detectable parasite 18S rRNA (FIG. 7A-B). These observations show that PfΔslarpΔb9 can invade, but do not develop in livers of chimeric mice engrafted with human liver tissue.

Example 9

Preparation of PfΔslarp Δb9 GAP Sporozoites Suitable for Pharmaceutical Compositions PfΔslarp Δb9 GAP sporozoites (SPZ) were grown aseptically in *A. stephensi* mosquitoes as described (Hoffman and Luke (2007) U.S. Pat. No. 7,229,627, incorporated herein by reference). Three hundred seventy eight infected mosquitoes, comprising an average of 91,931 SPZ/mosquito were vialed, purified (Sim et al (2011) U.S. Pat. No. 8,043,625), and cryopreserved. A Sporozoite Membrane Integrity Assay (SMIA) was performed on the cyropreserved product. The SMIA is a live/dead assay that fluorescently labels PfSPZ based on the intactness of their membranes. These PfΔslarpΔb9 GAP SPZ had an SMIA score of 90.7%, which is higher than the average of scores for all the clinical lots of cryopreserved radiation attenuated SPZ used by Sanaria Inc. in pharmaceutical compositions for the preparation of Sanaria® PfSPZ Vaccine and Sanaria® PfSPZ Challenge, and is higher than the values reported during stability studies of the vaccine lot used in the Sanaria® PfSPZ Vaccine clinical trial at NIH Vaccine Research Center [49].

Example 10

Safety of PfΔslarp Δb9 GAP Sporozoites Suitable for Pharmaceutical Compositions

A 6-Day Hepatocyte Potency Assay (See Sim et al (2011)) was performed on freshly dissected PfΔslarpΔb9 GAP SPZ rather than cryopreserved SPZ in order to maximize the chance of detecting any indication of breakthrough infections. In this assay, PfSPZ are allowed to invade and develop in vitro in human hepatocyte culture, and the number of parasites that develop into mature liver stage schizonts expressing the major merozoite surface protein-1 (PfMSP-1) are counted following a six-day incubation. Freshly dissected aseptic, purified, wild-type PfSPZ (NF54) were produced in parallel as a control and gave 26.0 parasites expressing PfMSP-1 per well (triplicate cultures) while freshly dissected Pf Δslarp Δb9 GAP SPZ showed 0.0 parasites per well (triplicate cultures) expressing PfMSP-1, thus demonstrating complete attenuation of the knock out PfΔslarpΔb9 GAP mutant parasites.

TABLES

TABLE 1

Protection in BALB/c and C57BL/6 mice following immunization with *P berghei* Ab9.

| Mice | Immunization dose Spz × $10^3$ | Challenge after immunization[a] (re-challenge) | No. protected/no. challenged prepatency[b] Δb9 | Control |
|---|---|---|---|---|
| Balb/c | 50 | d10 (d90 & d180 & d210 & d365) | 20/20 (15/15 & 10/10 & 5/5 & 5/5) | |
| | 25 | d10 (d90 & d180) | 10/10 (5/5 & 5/5) | |
| | 10 | d10 (d90 & d180) | 10/10 (5/5 & 5/5) | |

TABLE 1-continued

Protection in BALB/c and C57BL/6 mice following immunization with *P berghei* Ab9.

| Mice | Immunization dose Spz × 10³ | Challenge after immunization[a] (re-challenge) | No. protected/no. challenged prepatency[b] Äb9 | Control |
|---|---|---|---|---|
| | 5 | d10 (d90 & d180) | 8/10 7.5 (3/3 & 3/3) | |
| | 1 | d10 (d90 & d180) | 8/10 7 (3/3 & 3/3) | |
| | None | d10 & d90 & d180 & d210 & d365 | | 0/5[d] 4.5 |
| C57BL/6 | 50/20/20 | d10 (d90 & d180) | 4/4 (4/4 & 4/4) | |
| | 50/20/20[c] | d90 | 5/5 | |
| | 50/20/20[c] | d180 (d365) | 9/9 (4/4) | |
| | 50/20/20[c] | d365 | 5/11 7 | |
| | None | d10 & d90 & d180 & d365 | | 0/4[d] 4 |

[a]Challenge was performed by a 10⁴ wild type sporozoite IV injection.
[b]Mean of pre-patent period in days post challenge.
[c]Immunizations were performed with two 7 day intervals.
[d]Representative for challenge of naïve mice at any time point post last immunization

TABLE 2

Protection in BALB/c and C57BL/6 mice following immunization with *P.berghei* Δb9Δslarp and irradiated sporozoites.

| Mice | Immunization dose Spz × 10³ | Challenge after immunization[a] (re-challenge) | No. protected/no. challenged prepatency[b] Δb9 Δslarp | γ-irradiated | Control |
|---|---|---|---|---|---|
| Balb/c | 50 | d10 | | | |
| | 25 | d10 | 10/10 | | |
| | 10 | d10 | 20/20 | | |
| | 5 | d10 | 10/10 | | |
| | 1 | d10 | 20/20 | | |
| | None | d10 | | | 0/15 4.5 |
| C57BL/6 | 10/10/10[c] | d10 (d180) | 10/10 (5) | 10/10 (4/5) 8 | |
| | 1/1/1[c] | d10 | 6/10 | 7/10 | |
| | None | d10 | 7 | 7.3 | 0/6 4.5 |
| | 50/20/20[c] | d180 | 6/6 | 10/10 | |
| | 50/10/20[c] | d180 | 3/3 | | |
| | 50/20[d] | d180 | 1/1 | | |
| | None | d180 | | | 0/4 4 |

[a]Challenge was performed by a 104 wild-type sporozoite IV injection.
[b]Mean of pre-patent period in days post challenge.
[c]Immunizations were performed with two 7 day intervals.
[d]Immunizations were performed with a 14 day interval.

TABLE 3

Characterization of *P. falciparum* PfΔslarp and PfΔslarpΔb9 parasites. Gametocyte induction and gamete formation of Δslarp and ΔslarpΔb GAP parasites is not affected.

| Parasite | Gametocyte stage II no. Per 1000 RBC (range) | Gametocyte stage IV-V no. Per 1000 RBC (range) | Exfl.[a] | Oocyst production[b] (IQR) | % Infected mosquitoes (Infected/dissected) | Mean no. of sporozoites per mosquito × 1000 (std) |
|---|---|---|---|---|---|---|
| WT | 6.6 (1-13) | 51 (29-61) | ++ | 27 (12-42) | 95% (104/110) | 48 (23-95) |
| PfΔslarp-a | 8.8 (3-15) | 58 (41-65) | ++ | 23 (8-59) | 93% (37/40) | 50 (22-97) |
| PfΔslarp-b | 9.1 (2-27) | 49 (27-70) | ++ | 36 (17-59) | 96% (106/110) | 77 (22-174) |
| PfΔslarpΔb9-F7 | 8.2 (1-14) | 39 (22-47) | ++ | 34 (20-54) | 96% (77/80) | 81 (33-106) |
| PfΔslarpΔb9-G9 | 8.6 (4-12) | 49 (27-65) | ++ | 33 (13-64) | 94% (75/80) | 62 (22-105) |

Gametocyte induction, gamete formation, infectivity of mosquitoes and sporozoite production of PfΔslarp-a, PfΔslarp-b, PfΔslarpΔb9-F7 and PfΔslarpΔb9-G9 parasites are not affected. Gametocyte numbers were determined by counting stage II and IV-V gametocytes compared to red blood cells (RBC) in a thin blood smear respectively at day 8 and day 14 after the start of gametocyte cultures. [a]Exflagellation (Exfl) of male gametocytes was determined in stimulated samples from day 14 gametocyte cultures in wet mounted preparations at 400× magnification using a light microscope; ++ score=>10 exflagellation centers per microscope field. Oocyst and sporozoite production and infectivity was determined by feeding *A. stephensi* mosquitoes and dissection of mosquito midguts. [b]Oocyst production is the median of the oocysts counted at day 7 after mosquito feeding and IQR is the inter quartile range.

TABLE 4

List of primers used herein.

| | Name | Sequence | Restriction site | Description | Gene models |
|---|---|---|---|---|---|
| | Primers for generation of the ΔB9 target regions (for pL1439) (restriction sites are shown in red and underlined) | | | | |
| Δb9 | 4096 | GGGGTACCTAAATAACA TGATGAAACGTCAC (SEQ ID NO: 1) | Asp718 | Δb9 5'target F | PBANKA_080810 |
| Δb9 | 4097 | CCCAAGCTTTCTATGCAT TACTTCTACCCTC (SEQ ID NO: 2) | HindIII | Δb9 5'target R | PBANKA_080810 |
| Δb9 | 4098 | GGAATTCGATATGCTTGA AATTCCTAGAC (SEQ ID NO: 3) | EcoRI | Δb9 3'target F | PBANKA_080810 |
| Δb9 | 4099 | TCCCCCCGGGCGCTTGTG GTTGCATACATC (SEQ ID NO: 4) | XmaI | Δb9 3'target R | PBANKA_080810 |
| | Primers for confirmation PCR of the integration event in ΔB9 | | | | |
| Δb9 | 4288 | CAAATCCACAGACACTT ACTC (SEQ ID NO: 5) | | Δb9 5'integration F | PBANKA_080810 |
| Δb9 | L1858 | ATGCACAAAAAAAATA TGCACAC (SEQ ID NO: 6) | | Δb9 5'integration R from KO construct pL1439 | PBANKA_080810 |
| Δb9 | 4239 | GATTTTTAAAATGTTTAT AATATGATTAGC (SEQ ID NO: 7) | | Δb9 3'integration F from KO construct pL1439 | PBANKA_080810 |
| Δb9 | 4289 | CAACCTTTTGCCTTGCAT G (SEQ ID NO: 8) | | Δb9 3'integration R | PBANKA_080810 |
| Δb9 | 4437 | CGCATTATTCGAGGTAG ACC (SEQ ID NO: 9) | | Δb9 orf F | PBANKA_080810 |
| Δb9 | 4438 | ACGGGTTTCACTTACATA CTC (SEQ ID. NO: 10) | | Δb9 orf R | PBANKA_080810 |
| Δb9 | 4698 | GTTCGCTAAACTGCATCG TC (SEQ ID NO: 11) | | hdhfr F | |
| Δb9 | 4699 | GTTTGAGGTAGCAAGTA GACG (SEQ ID NO: 12) | | yfcu R | |
| Δb9 | 5441 | ATGAGCATAAATGTCTAG CATGG (SEQ ID NO: 13) | | Δb9 negative selection 5' target F | PBANKA_080810 |
| Δb9 | 5442 | CTTGAACCTAGATTGGGT GTAG (SEQ ID NO: 14) | | Δb9 negative selection 3' target R | PBANKA_080810 |
| | Primers for the Anchor-tagging PCR-based method: Generation of ΔB9 target regions (for pL1499) (restriction sites are shown in red and underlined; Anchor tags are shown in blue and bolded) | | | | |
| Δb9 | 4667 | GAACTCGTACTCCTTGG TGACGGGTACCTAAATA ACATGATGAAACGTCAC (SEQ ID NO: 15) | Asp718 | Δb9 5'target F | PBANKA_080810 |
| Δb9 | 4557 | CATCTACAAGCATCGTC GACCTCTCTATGCATTA CTTCTACCCTC (SEQ ID NO: 16) | | Δb9 5'target R | PBANKA_080810 |

TABLE 4-continued

List of primers used herein.

| | Name | Sequence | Restriction site | Description | Gene models |
|---|---|---|---|---|---|
| Δb9 | 4558 | CCTTCAATTTCGGATCC ACTAGGATATGCTTGAA ATTCCTAGAC (SEQ ID NO: 17) | | Δb9 3'target F | PBANKA_080810 |
| Δb9 | 4668 | AGGTTGGTCATTGACA CTCAGC<u>AGTACT</u>CGCTT GTGGTTGCATACATC (SEQ ID NO: 18) | ScaI | Δb9 3'target R | PBANKA_080810 |
| Δb9 | 4661 | GAACTCGTACTCCTTGG TGACG (SEQ ID NO: 19) | | for 2nd PCR | anchor tag |
| Δb9 | 4662 | AGGTTGGTCATTGACA CTCAGC (SEQ ID NO: 20) | | for 2nd PCR | anchor tag |

Primers for confirmation PCR of the integration event in ΔB9 (Anchor tags are shown in blue and bolded)

| Δb9 | 4288 | CAAATCCACAGACACTT ACTC (SEQ ID NO: 21) | | Δb9 5'integration F | |
| --- | --- | --- | --- | --- | --- |
| Δb9 | 4770 | CATCTACAAGCATCGTC GACCTC (SEQ ID NO: 22) | | Δb9 5'integration R from anchor tag KO construct pL1499 | |
| Δb9 | 4771 | CCTTCAATTTCGGATCC ACTAG (SEQ ID NO: 23) | | Δb9 3'integration F from anchor tag KO construct pL1499 | |
| Δb9 | 4289 | CAACCTTTTGCCTTGCAT G (SEQ ID No: 24) | | Δb9 3'integration R | |
| Δb9 | 4437 | CGCATTATTCGAGGTAG ACC (SEQ ID NO: 25) | | Δb9 orf F | PBANKA_080810 |
| Δb9 | 4438 | ACGGGTTTCACTTACATA CTC (SEQ ID NO: 26) | | Δb9 orf R | PBANKA_080810 |
| Δb9 | L307 | CGCTTAATTCTTTTCGAGC TC (SEQ ID NO: 27) | | hdhfr F | |
| Δb9 | 3187 | GTGTCACTTTCAAAGTCT TGC (SEQ ID NO: 28) | | hdhfr R | |
| Primers for RT-PCR | | | | | |
| RT-PCR | 6301 | ATACCAGAACCACATGT TACG (SEQ ID NO: 29) | | CS for RT primer | PBANKA_040320 |
| RT-PCR | 6302 | CTCTACTTCCAGGATATG GAC (SEQ ID NO: 30) | | CS F for RT-PCR | PBANKA_040320 |
| RT-PCR | 6303 | CATTGAGACCATTCCTCT GTG (SEQ ID NO: 31) | | CS R for RT-PCR | PBANKA_040320 |
| RT-PCR | 7034 | CCATTCTGGGTAGAACA AATGC (SEQ ID NO: 32) | | b9 for RT primer | PBANKA_080810 |
| RT-PCR | 7035 | TATCCCATCACTCATACC TAG (SEQ ID NO: 33) | | b9 F for RT-PCR | PBANKA_080810 |
| RT-PCR | 7036 | ACGGGTTTCACTTACATA CTC (SEQ ID NO: 34) | | b9 R for RT-PCR | PBANKA_080810 |

TABLE 4-continued

List of primers used herein.

| Name | | Sequence | Restriction site | Description | Gene models |
|---|---|---|---|---|---|

Primers for the Anchor tagging PCR-based method: Generation of Δslarp target regions (for pL1740) (restriction sites are shown in red and underlined; Anchor tags are shown in blue and bolded)

| Δslarp | 5960 | GAACTCGTACTCCTTGG TGACGGGTACCGGGAGT CAAAAACGGTATGC (SEQ ID NO: 35) | Asp718 | Δslarp 5'target F | PBANKA_090210 |
| Δslarp | 5961 | CATCTACAAGCATCGTC GACCTCTCCTATAGTAC ATGCCCACG (SEQ ID NO: 36) | | Δslarp 5'target R | PBANKA_090210 |
| Δslarp | 5962 | CCTTCAATTTCGGATCC ACTAGCATGTTAGGAGC ACGAAACC (SEQ ID NO: 37) | | Δslarp 3'target F | PBANKA_090210 |
| Δslarp | 5963 | AGGTTGGTCATTGACA CTCAGCAGTACTCTAAA ATTGTGGGAATCCACTTG (SEQ ID NO: 38) | SeaI | Δslarp 3'target R | PBANKA_090210 |
| | 4661 | GAACTCGTACTCCTTGG TGACG (SEQ ID NO: 39) | | for 2nd PCR | |
| | 4662 | AGGTTGGTCATTGACA CTCAGC (SEQ ID NO: 40) | | for 2nd PCR | |

Primers for confirmation PCR of the integration event in Δslarp (Anchor tags are shown in blue)

| Δslarp | 6125 | CATGTCTCTTTGCATGTG GC (SEQ ID NO: 41) | | Δslarp 5'integration F | PBANKA_090210 |
| Δslarp | 6349 | CTCATCTACAAGCATCG TCG (SEQ ID NO: 42) | | Δslarp 5'integration R from KO construct | |
| Δslarp | 4771 | CCTTCAATTTCGGATCC ACTAG (SEQ ID NO: 43) | | Δslarp 3'integration F from KO construct | |
| Δslarp | 6126 | GTCGTCCTATAGTAAGTT GAGC (SEQ ID NO: 44) | | Δslarp 3'integration R | PBANKA_090210 |
| Δslarp | 6127 | CCCAAATGATCAAGCAC CAG (SEQ ID NO: 45) | | slarp orf F | PBANKA_090210 |
| Δslarp | 6128 | CAATTTGAATCGGCACA AGGC (SEQ ID NO: 46) | | slarp orf R | PBANKA_090210 |
| | 6346 | TGGACATTGCCTATGAGG AG (SEQ ID NO: 47) | | hdhfr-yfcu F | |
| | 6347 | AACACAGTAGTATCTGTC ACC (SEQ ID NO: 48) | | hdhfr-yfcu R | |
| Δb9 | 4437 | CGCATTATTCGAGGTAG ACC (SEQ ID NO: 49) | | b9 orf F | PBANKA_080810 |
| Δb9 | 4438 | ACGGGTTTCACTTACATA CTC (SEQ ID NO:50) | | b9 orf R | PBANKA_080810 |

TABLE 5

Phenotypic analysis of P. berghei Δb9 mosquito and liver stages.

| Parasite | Oocyst No. Mean ± sd | Spz No. (×10³) Mean ± sd | Sporozoite Motility[a] | Cell Traversal[b] | Hepatocyte invasion[c] |
|---|---|---|---|---|---|
| WT | 85 ± 25 | 102 ± 28 | 1.00 ± 0.03 | 1.00 ± 0.14 | 1.00 ± 0.12 |
| WT (PbGFP-Luc_con) | 63 ± 15 | 86 ± 24 | Nd | 1.0 ± 0.1 | 0.92 ± 0.16 |
| Δb9-a | 89 ± 14 | 89 ± 28 | 1.01 ± 0.02 | 1.11 ± 0.03 | 1.08 ± 0.28 |
| Δb9-b | 55 ± 18 | 85 ± 25 | Nd | 0.9 ± 0.08 | 1.03 ± 0.07 |

[a]Determined by counting CS protein sporozoite trails.
[b]Sporozoite Traversal through Huh-7 cells.
[c]Sporozoite invasion of Huh-7 cells. Number of intracellular parasites determined at 3 h after infection.

TABLE 6

Breakthrough blood infection in Swiss, BALB/c and C57BL/6 after inoculation with P. berghei Δb9 mutants.

| Mouse strain | Parasites | Dose[a] | breakthrough/infected animals | pre-patency (days) |
|---|---|---|---|---|
| Swiss | WT | 1 × 10⁴ | 5/5 | 5 |
|  | PbΔb9-a | 1 × 10⁴ | 0/3 | n/a |
|  | PbΔb9-b | 1 × 10⁴ | 0/3 | n/a |
|  | PbΔb9-b | 5 × 10⁴ | 0/3 | n/a |
| BALB/c | WT | 1 × 10⁴ | 5/5 | 5 |
|  | PbΔb9-a | 5 × 10⁴ | 0/20 | n/a |
|  | PbΔb9-b | 5 × 10⁴ | 0/10 | n/a |
| C57BL/6 | WT | 1 × 10⁴ | 5/5 | 5 |
|  | PbΔb9-a | 5 × 10⁴ | 2/10 | 8-9 |
|  | PbΔb9-b | 5 × 10⁴ | 1/10 | 9 |
|  | PbΔb9-b | 2 × 10⁵ | 2/10 | 8-9 |

[a]Inoculation dose of sporozoites administered IV

TABLE 7

Phenotypic analysis of P. berghei Δslarp and Δb9Δslarp mosquito and liver stages.

| Parasite | Oocyst No. Mean ± sd | Spz No. (×10³) Mean ± sd | Sporozoite Mobility[a] | Cell Traversal[b] | Hepatocyte invasion[c] |
|---|---|---|---|---|---|
| WT | 119 ± 40 | 108 ± 23 | 1.0 ± 0.1 | 1.00 ± 0.08 | 1.00 ± 0.06 |
| Δslarp-a | 154 ± 17 | 88 ± 41 | 1.01 ± 0.13 | 1.09 ± 0.06 | 0.97 ± 0.11 |
| Δb9Δslarp | 172 ± 5 | 43 ± 23 | 1.05 ± 0.03 | 1.21 ± 0.12 | 1.02 ± 0.03 |

[a]Determined by counting CS protein sporozoite trails.
[b]Sporozoite Traversal through Huh-7 cells.
[c]Sporozoite invasion of Huh-7 cells. Number of intracellular parasites determined at 3 h after infection.

TABLE 8

No breakthrough blood infection in BALB/c and C57BL/6 after inoculation with P. berghei Δslarp and Δb9Δslarp sporozoites.

| Mouse strain | Parasites | Dose[a] | breakthrough/infected animals | pre-patency (days) |
|---|---|---|---|---|
| BALB/c | WT | 1 × 10⁴ | 5/5 | 4-5 |
|  | Δslarp-a | 5 × 10⁴ | 0/5 | n/a |
|  | Δslarp-a | 25 × 10³ | 0/10 | n/a |
|  | Δb9Δslarp | 25 × 10³ | 0/10 | n/a |
| C57BL/6 | WT | 1 × 10⁴ | 5/5 | 4-5 |
|  | Δslarp-a | 5 × 10⁵ | 0/5 | n/a |
|  | Δslarp-a | 4 × 10⁵ | 0/5 | n/a |
|  | Δslarp-a | 2 × 10⁵ | 0/10 | n/a |
|  | Δb9Δslarp | 2 × 10⁵ | 0/10 | n/a |
|  | Δb9Δslarp | 15 × 10⁴ | 0/5 | n/a |

[a]Inoculation dose of sporozoites administered IV

TABLE 9

Protection in BALB/c and C57BL/6 mice following immunization with P. berghei Δslarp sporozoites.

| Mice | Immunization dose Spz × 10³ | Challenge after immunization[a] (re-challenge) | Δslarp (1839 cl3) | Δslarp (SL22cl3)[e] | Control[f] |
|---|---|---|---|---|---|
| Balb/c | 50 | d10 |  | 14/14 |  |
|  | 25 | d10 | 10/10 | 14/14 |  |
|  | 10 | d10 | 19/20 5 | 10/10 |  |
|  | 5 | d10 | 10/10 | 10/10 |  |
|  | 1 | d10 | 20/10 | 8/10 8 |  |
|  | None | d10 |  |  | 0/15 4.5 |
| C57BL/6 | 10/10/10[c] | d10 (d180) | 10/10 (10/10) | 10/10 (9/10) 8 |  |
|  | 1/1/1c | d10 (d180) | 5/10 7.2 (4/5) 6 | 5/10 7.8 (5/5) |  |
|  | None | d10 |  |  | 0/6 4.5 |
|  | 50/20/20[c] | d180 | 8/9 9 |  |  |
|  | 50/20/20[c] | d180 |  | 6/7 7 |  |
|  | 50/20[d] | d180 |  | 3/3 |  |
|  | None | d180 |  |  | 0/4 4 |

[a]Challenge was performed by a 10⁴ wild-type sporozoite IV injection.
[b]Mean of pre-patent period in days post challenge.
[c]Immunizations were performed with two 7 day intervals.
[d]Immunizations were performed with a 14 day interval.
eThis Δslarp GAP was previously generated and published [15].
[f]For each mouse strain, immunizations and challenges were conducted in one experiment. Immunizations of mice presented in Table 2 were performed simultaneous with the immunization experiments presented in Table 9; hence only one group of control mice were used per challenge time point.

TABLE 10

Liver stage development of rodent Plasmodium 6-Cys mutants, in vivo

| Mouse strain | Parasite | Dose | Positive mice infected mice (%) | Pre-patency (days) 5 |
|---|---|---|---|---|
| SWISS | WT (P. berghei) | 1 × 10⁴ | 5/5 (100%) | 5 |
|  | PbΔb9-a | 1 × 10⁴ | 0/3 (0%) | n/a |
|  | PbΔb9-b | 1 × 10⁴ | 0/3 (0%) | n/a |
|  | PbΔb9-b | 5 × 10⁴ | 0/3 (0%) | n/a |
|  | Pbb9::cmyc | 1 × 10⁴ | 0/3 (0%) | n/a |
|  | Pbb9::cmyc | 5 × 10⁴ | 0/3 (0%) | n/a |
|  | PbΔsequestrin-a | 1 × 10⁴ | 3/7 (43%) | 8 |
|  | PbΔsequestrin-a | 5 × 10⁴ | 3/3 (100%) | 7-8 |
|  | PbΔsequestrin-b | 1 × 10⁴ | 4/4 (100%) | 7 |
| BALB/c | WT (P. berghei) | 1 × 10⁴ | 5/5 (100%) | 5 |
|  | WT (P. yoelii) | 1 × 10⁴ | 5/5 (100%) | 3-4 |

TABLE 10-continued

Liver stage development of rodent Plasmodium 6-Cys mutants, in vivo

| Mouse strain | Parasite | Dose | Positive mice infected mice (%) | Pre-patency (days) |
|---|---|---|---|---|
| | PbΔb9-a | $5 \times 10^4$ | 0/20 (0%) | n/a |
| | PbΔb9-b | $5 \times 10^4$ | 0/10 (0%) | n/a |
| | PyΔb9 | $5 \times 10^4$ | 0/15 (0%) | n/a |
| | PyΔb9 | $2 \times 10^4$ | 1/8 (12.5%) | 10 |
| C57BL6 | WT (P. berghei) | $1 \times 10^4$ | 5/5 (100%) | 5 |
| | PbΔb9-a | $5 \times 10^4$ | 2/10 (20%) | 8-9 |
| | PbΔb9-b | $5 \times 10^4$ | 1/10 (10%) | 9 |
| | PbΔPbb9-b | $2 \times 10^5$ | 2/10 (20%) | 8-9 |
| | PbΔp52Δp36 | $2 \times 10^5$ | 10/10 (100%) | 6-7 |
| | PbΔb9Δp52Δp36 | $5 \times 10^4$ | 1/10 (10%) | 9 |
| | PbΔb9Δp52Δp36 | $2 \times 10^5$ | 2/10 (20%) | 8-9 |

TABLE 11

Sexual-and mosquito-stage development of the different *Plasmodium* mutants
*P. berghei* and *P. yoelii* mutant oocyst and sporozoite production and
sporozoite characteristics (motility, traversal, hepatocyte invasion)

| Parasite | Oocyst no.[a] Mean ± sd | Sporozoite no.[b] Mean ± sd | Gliding motility[c] Mean ± sd | Cell traversal[d] Mean ± sd | Hepatocyte invasion[e] Mean ± sd |
|---|---|---|---|---|---|
| PbWT (cll5cyl) | 85 ± 25 | 102K ± 28K | 89 ± 3 | 20.7 ± 3.0 | |
| PbWT (PbGFP-Luc$_{con}$) | 63 ± 15 | 86K ± 24K | nd | 18.9 ± 2.1 | |
| PbΔb9-a | 89 ± 14 | 89K ± 28K | 90 ± 2 | 22.9 ± 0.6 | |
| PbΔb9-b | 55 ± 18 | 85 ± 25K | nd | 18.7 ± 1.7 | |
| PbWT (GFP-Luc$_{con}$) | 256 ± 77 | 115K ± 45K | 73 ± 5 | nd | 37.9 ± 6.4 |
| PbΔb9-a | 241 ± 61 | 89K ± 32K | 68 ± 8 | nd | 40.6 ± 4.3 |
| PbΔb9-b | 236 ± 70 | 106K ± 22K | 72 ± 4 | nd | 35.2 ± 9.8 |
| Δsequestrin | 291 ± 94 | 96K ± 15K | 78 ± 6 | nd | 41.2 ± 7.4 |
| Δb9Δp52Δp36 | 301 ± 64 | 85K ± 24K | 75 ± 4 | nd | 38.6 ± 5.4 |
| PyWT (GFP-Luc$_{con}$) | 43 ± 22 | 42K ± 18K | nd | nd | nd |
| PyΔb9 | 64 ± 38 | 23K ± 32K | nd | nd | nd |

[a] Mean number of oocysts per mosquito;
[b] Mean number of sporozoites per salivary gland;
[c] percentage of sporozoites that show gliding motility;
[d] Percentage of dextran positive hepatocytes;
[e] Percentage of intracellular sporozoites at 3 hours post infection of hepatocytes

*P. falciparum* Δb9 gametocyte, oocyst and sporozoite production

| Parasite | Gametocyte stage II no./1000 RBC (range) | Gametocyte stage IV-V no./ 1000 RBC (range) | Exfl.[a] | Oocyst production[b] (IQR) | Infected/ dissected Mosquitoes | % Infected Mosquitoes | Mean no. of sporozoites per mosquito × 1000 (sd) |
|---|---|---|---|---|---|---|---|
| WT (NF54) | 8 (1-24) | 47 (21-61) | ++ | 19 (11-35) | 18/20 | 90 | 86 (31) |
| PfΔb9-a | 13 (10-16) | 54 (45-68) | ++ | 20 (7-50) | 19/20 | 95 | 102 |
| PfΔb9-b | 8 (3-14) | 47 (37-59) | ++ | 19 (6-51) | 18/20 | 90 | 156 (27) |

[a] Exflagellation (Exfl) of male gametocytes was determined in stimulated samples from day 14 gametocyte cultures in wet mounted preparations at 400× magnification using a light microscope; ++ score => 10 exflagellation centers per microscope field;
[b] Oocyst production is the median of the oocysts counted at day 7 after feeding of the mosquitoes.
IQR is the inter quartile range.

TABLE 12

Primer sequences used to generate b9 knock-out lines for *P. berghei*, *P. yoelii* and *P. falciparum*.

Primers for generation of the mcherry@b9 promoter (for pL1695) (restriction sites are underlined)

| | | | | | Gene Models |
|---|---|---|---|---|---|
| mcherry@ b9 promoter | 5497 | GCGCCTTAAGTTTCCACATATGTGCAGGTG (SEQ ID NO: 66) | AfIII | b9 promoter F | PBANKA_080810 |

TABLE 12-continued

Primer sequences used to generate b9 knock-out lines for *P. berghei*, *P. yoelii* and *P. falciparum*.

| | | | | | Gene Models |
|---|---|---|---|---|---|
| mcherry@ b9 promoter | 5498 | CG<u>GGATCC</u>TTATATATTTAACACTATTAATTTA TCTTA (SEQ ID NO: 67) | BamHI | b9 promoter R | PBANKA_080810 |
| mcherry@ b9 promoter | 4694 | AAGGAAAAAA<u>GCGGCCGC</u>AAATTGTAATAAT ATAAAAGAATGAGAAATTCG (SEQ ID NO: 68) | NotI | b9 3' utr F | PBANKA_080810 |
| mcherry@ b9 promoter | 5135 | gc<u>GGTACC</u>CTTCTTCGTACATATATGTAGC (SEQ ID NO: 69) | Asp718 | b9 3' utr R | PBANKA_080810 |

Primers for generation of the Δb9 target regions (for pL1439)
(restriction sites are underlined)

| | | | | | |
|---|---|---|---|---|---|
| Δb9 | 4096 | GGG<u>GTACC</u>TAAATAACATGATGAAACGTCAC (SEQ ID NO: 1) | Asp718 | Δb9 5' target F | PBANKA_080810 |
| Δb9 | 4097 | CCC<u>AAGCTT</u>TCTATGCATTACTTCTACCCTC (SEQ ID NO: 2) | HIndIII | Δb9 5'target R | PBANKA_080810 |
| Δb9 | 4098 | G<u>GAATTC</u>GATATGCTTGAAATTCCTAGAC (SEQ ID NO: 3) | EcoRI | Δb9 3' target F | PBANKA_080810 |
| Δb9 | 4099 | TCC<u>CCCGGG</u>CGCTTGTGGTTGCATACATC (SEQ ID NO: 4) | XmaI | Δb9 3' target R | PBANKA_080810 |

Primers for confirmation PCR of the integration event in Δb9

| | | | | | |
|---|---|---|---|---|---|
| Δb9 | 4288 | CAAATCCACAGACACTTACTC (SEQ ID NO: 5) | | Δb9 5' integration F | PBANKA_080810 |
| Δb9 | L1858 | ATGCACAAAAAAAAATATGCACAC (SEQ ID NO:6) | | Δb9 5' integration R from KO construct pL1439 | PBANKA_080810 |
| Δb9 | 4239 | GATTTTTAAAATGTTTATAATATGATTAGC (SEQ ID NO: 7) | | Δb9 3' integration F from KO construct pL1439 | PBANKA_080810 |
| Δb9 | 4289 | CAACCTTTTGCCTTGCATG (SEQ ID NO: 8) | | Δb9 3' integration R | PBANKA_080810 |
| Δb9 | 4437 | CGCATTATTCGAGGTAGACC (SEQ ID NO: 9) | | Δb9 orf F | PBANKA_080810 |
| Δb9 | 4438 | ACGGGTTTCACTTACATACTC (SEQ ID NO: 10) | | Δb9 orf R | PBANKA_080810 |
| Δb9 | 4698 | GTTCGCTAAACTGCATCGTC (SEQ ID NO: 11) | | hdhfr F | |
| Δb9 | 4699 | GTTTGAGGTAGCAAGTAGACG (SEQ ID NO: 12) | | yfcu R | |
| Δb9 | 5441 | ATGAGCATAAATGTGAGCATGG (SEQ ID NO: 13) | | Δb9 negative selection 5' target F | PBANKA_080810 |
| Δb9 | 5442 | CTTGAACCTAGATTGGGTGTAG (SEQ ID NO: 14) | | Δb9 negative selection 3' target R | PBANKA_080810 |

TABLE 12-continued

Primer sequences used to generate b9 knock-out lines for *P. berghei*, *P. yoelii* and *P. falciparum*.

|  |  |  |  |  | Gene Models |
|---|---|---|---|---|---|

Primers for the Anchor-tagging PCR-based method: Generation of ΔB9 target regions (for pL1499) (restriction sites are underlined; Anchor tags are double underlined)

| Δb9 | 4667 | <u>GAACTCGTACTCCTTGGTGACGGGTACC</u>TAAATAACATGATGAAACGTCAC (SEQ ID NO: 15) | Asp718 | Δb9 5' target F | PBANKA_080810 |
|---|---|---|---|---|---|
| Δb9 | 4557 | <u>CATCTACAAGCATCGTCGACCTC</u>TCTATGCATTACTTCTACCCTC (SEQ ID NO: 16) |  | Δb9 5'target R | PBANKA_080810 |
| Δb9 | 4558 | <u>CCTTCAATTTCGGATCCACTAG</u>GATATGCTTGAAATTCCTAGAC (SEQ ID NO: 17) |  | Δb9 3' target F | PBANKA_080810 |
| Δb9 | 4668 | <u>AGGTTGGTCATTGACACTCAGC</u>AGTACTCGCTTGTGGTTGCATACATC (SEQ ID NO: 18) | ScaI | Δb9 3' target R | PBANKA_080810 |
| Δb9 | 4661 | <u>GAACTCGTACTCCTTGGTGACG</u> (SEQ ID NO: 19) |  | for 2nd PCR | anchor tag |
| Δb9 | 4662 | <u>AGGTTGGTCATTGACACTCAGC</u> (SEQ ID NO: 20) |  | for 2nd PCR | anchor tag |

Primers for confirmation PCR of the integration event in ΔB9 (Anchor tags are double underlined)

| Δb9 | 4288 | CAAATCCACAGACACTTACTC (SEQ ID NO: 21) |  | Δb9 5' integration F |  |
|---|---|---|---|---|---|
| Δb9 | 4770 | <u>CATCTACAAGCATCGTCGACCTC</u> (SEQ ID NO: 22) |  | Δb9 5' integration R from KO construct pL1499 | anchor tag |
| Δb9 | 4771 | <u>CCTTCAATTTCGGATCCACTAG</u> (SEQ ID NO: 23) |  | Δb9 3' integration F from KO construct pL1499 | anchor tag |
| Δb9 | 4289 | CAACCTTTTGCCTTGCATG (SEQ ID NO: 24) |  | Δb9 3' integration R |  |
| Δb9 | 4437 | CGCATTATTCGAGGTAGACC (SEQ ID NO: 25) |  | Δb9 orf F | PBANKA_080810 |
| Δb9 | 4438 | ACGGGTTTCACTTACATACTC (SEQ ID NO: 26) |  | Δb9 orf R | PBANKA_080810 |
| Δb9 | L307C | GCTTAATTCTTTTCGAGCTC (SEQ ID NO: 27) |  | hdhfr F |  |
| Δb9 | 3187 | GTGTCACTTTCAAAGTCTTGC (SEQ ID NO: 28) |  | hdhfr R |  |

Primers for generation of the ΔPBANKA_100300 target regions (for pL1462) (restriction sites are underlined)

| Δsequestrin | 4261 | GGG<u>GTACC</u>CAACAGCAATATATCGTCACC (SEQ ID NO: 70) | Asp718 | ΔPBANKA_100300 5' target F | PBANKA_100300 |
|---|---|---|---|---|---|
| Δsequestrin | 4262 | CCC<u>AAGCTT</u>CGTGTTTCCTTTCTTTTTCTCG (SEQ ID NO: 71) | HIndIII | ΔPBANKA_100300 5'target R | PBANKA_100300 |
| Δsequestrin | 4263 | GG<u>AATTC</u>GAAGAAAACAATAAAGAGCTACC (SEQ ID NO: 72) | EcoRI | ΔPBANKA_100300 3' target F | PBANKA_100300 |
| Δsequestrin | 4264 | CG<u>GGATCC</u>CGATATCGACGTAGCTTACCG (SEQ ID NO: 73) | BamHI | ΔPBANKA_100300 3' target R | PBANKA_100300 |

TABLE 12-continued

Primer sequences used to generate b9 knock-out lines for *P. berghei*, *P. yoelii* and *P. falciparum*.

Primers for confirmation PCR of the integration event in ΔPBANKA_100300

| | | | | | Gene Models |
|---|---|---|---|---|---|
| Δsequestrin | 4459 | GTATGCTTTCGGAAAACTCTAC (SEQ ID NO: 74) | | ΔPBANKA_100300 5' integration F | PBANKA_100300 |
| Δsequestrin | 4703 | ATTGTTGACCTGCAGGCATG (SEQ ID NO: 75) | | ΔPBANKA_100300 5' integration R from KO construct pL1462 | PBANKA_100300 |
| +66sequestrin | 4704 | GATTCATAAATAGTTGGACTTG (SEQ ID NO: 76) | | ΔPBANKA_100300 3' integration F from KO construct pL1462 | PBANKA_100300 |
| Δsequestrin | 4460 | GAAGAAGTATGACCATACGC (SEQ ID NO: 77) | | ΔPBANKA_1003003' integration R | PBANKA_100300 |
| Δsequestrin | 4472 | ATGGAATGGGAAAGAGAAAGAG (SEQ ID NO: 78) | | ΔPBANKA_100300 orf F | PBANKA_100300 |
| Δsequestrin | 4473 | GAAGGTCTTTTAATGTTGCCCTC (SEQ ID NO: 79) | | ΔPBANKA_100300 orf R | PBANKA_100300 |
| Δsequestrin | 4501 | GGACAGATTGAACATCGTCG (SEQ ID NO: 80) | | tgdhfr/ts-F | |
| Δsequestrin | 4502 | GATCACATTCTTCAGCTGGTC (SEQ ID NO: 81) | | tgdhfr/ts-R | |

Primers for the Anchor-tagging PCR-based method: Generation of ΔPyb9 target regions (for pL1938) (restriction sites are underlined)

| PyΔb9 | 7209 | CATGGGCCCTTTCCACATGTATGTGCAGGTG (SEQ ID NO: 82) | ApaI | ΔPyb9 5' target F | PY00153 |
| PyΔb9 | 7210 | GCGCCTTAAGAACAAGTCATAACCACGTTCTG (SEQ ID NO: 83) | AflII | ΔPyb9 5'target R | PY00153 |
| PyΔb9 | 7211 | ATAGTTTAGCGGCCGCGGACCAAGTAATGAAACCCG (SEQ ID NO: 84) | NotI | ΔPyb9 3' target F | PY00153 |
| PyΔb9 | 7212 | GGAATTCTGCAAATAATGTCGATTTAAGAG (SEQ ID NO: 85) | EcoRI | ΔPyb9 3' target R | PY00153 |

Primers for confirmation PCR of the integration event in ΔPyb9 (Anchor tags are shown in blue)

| PyΔb9 | 7259 | AAAGCCCGAGGCAAACAAAC (SEQ ID NO: 86) | | ΔPyb9 5' integration F | PY00153 |
| PyΔb9 | L1858 | ATGCACAAAAAAAAATATGCACAC (SEQ ID NO: 87) | | ΔPyb9 5' integration R from KO construct | anchor tag |
| PyΔb9 | 4239 | GATTTTAAAATGTTTATAATATGATTAGC (SEQ ID NO: 88) | | ΔPyb9 3' integration F from KO construct | PY00153 |
| PyΔb9 | 7260 | GCTTGTGATTGCATACATCGTG (SEQ ID NO: 89) | | ΔPyb9 3' integration R | anchor tag |
| PyΔb9 | 7261 | CCGTTAAGTGTCTAGTATGGTTG (SEQ ID NO: 90) | | ΔPyb9 orf F | PY00153 |

TABLE 12-continued

Primer sequences used to generate b9 knock-out lines for *P. berghei*, *P. yoelii* and *P. falciparum*.

| | | | | | Gene Models |
|---|---|---|---|---|---|
| PyΔb9 | 7262 | CCTCGAACAATGCGTAGTAC (SEQ ID NO: 91) | | ΔPyb9 orf R | PY00153 |
| PyΔb9 | 4698 | GTTCGCTAAACTGCATCGTC (SEQ ID NO: 92) | | hdhfr F | |
| PyΔb9 | 4699 | GTTTGAGGTAGCAAGTAGACG (SEQ ID NO: 93) | | yfcu R | |

Primers for generation of the PfΔb9 target regions (restriction sites are shown in red)

| PfΔb9 | BVS84 | Ctaccatggtatgggagcttgggcataatgtcatg (SEQ ID NO: 94) | NcoI, | PfΔb9 5' target F | PF3D7_0317100 |
| PfΔb9 | BVS85 | gtacccgggcgtgtcttatcatattcacaaaggc (SEQ ID NO: 95) | XmaI | PfΔb9 5'target R | PF3D7_0317100 |
| PfΔb9 | BVS88 | catacgcgtcctatatgatcaatcaccacctag (SEQ ID NO: 96) | MluI | PfΔb9 3' target F | PF3D7_0317100 |
| PfΔb9 | BVS89 | atagcgcgctgtctatcatacaaactggcatcc (SEQ ID NO: 97) | BssHII | PfΔb9 3' target R | PF3D7_0317100 |

Primers for confirmation PCR of the integration event in PfΔb9

| PfΔb9 | BVS123 | tcatgggtttttaaatagcctc (SEQ ID NO: 98) | | LR-PCR | PF3D7_0317100 |
| PfΔb9 | BVS125 | gatgtacacctacatttgaatgaag (SEQ ID NO: 99) | | LR-PCR | PF3D7_0317100 |
| PfΔb9 | BVS286 | tccacatggatgatatggtatgg (SEQ ID NO: 100) | | RT-PCR | PF3D7_0317100 |
| PfΔb9 | BVS288 | tgttgtgctcactagacgg (SEQ ID NO: 101) | | RT-PCR | PF3D7_0317100 |
| 18S rRNA | 18Sf | gtaattggaatgataggaatttacaaggt (SEQ ID NO: 102) | | RT-PCR | |
| 18S rRNA | 18Sr | tcaactacgaacgttttaactgcaac (SEQ ID NO: 103) | | RT-PCR | |

REFERENCES

1. WHO (2011) World Malaria Report. http://www.who.int/malaria/world_malaria_report_2011/9789241564403_eng.pdf.
2. Agnandji S T, Lell B, Soulanoudjingar S S, Fernandes J F, Abossolo B P, et al. (2011) First results of phase 3 trial of RTS,S/AS01 malaria vaccine in African children. N Engl J Med 365: 1863-1875.
3. Nussenzweig R S, Vanderberg J, Most H, Orton C (1967) Protective immunity produced by the injection of x-irradiated sporozoites of *Plasmodium berghei*. Nature 216: 160-162.
4. Gwadz R W, Cochrane A H, Nussenzweig V, Nussenzweig R S (1979) Preliminary studies on vaccination of rhesus monkeys with irradiated sporozoites of *Plasmodium knowlesi* and characterization of surface antigens of these parasites. Bull World Health Organ 57 Suppl 1: 165-173.
5. Clyde D F, Most H, McCarthy V C, Vanderberg J P (1973) Immunization of man against sporozite-induced *falciparum* malaria. Am J Med Sci 266: 169-177.
6. Rieckmann K H, Carson P E, Beaudoin R L, Cassells J S, Sell K W (1974) Letter: Sporozoite induced immunity in man against an Ethiopian strain of *Plasmodium falciparum*. Trans R Soc Trop Med Hyg 68: 258-259.
7. Hoffman S L, Goh L M, Luke T C, Schneider I, Le T P, et al. (2002) Protection of humans against malaria by immunization with radiation-attenuated *Plasmodium falciparum* sporozoites. J Infect Dis 185: 1155-1164.
8. Belnoue E, Costa F T, Frankenberg T, Vigario A M, Voza T, et al. (2004) Protective T cell immunity against malaria liver stage after vaccination with live sporozoites under chloroquine treatment. J Immunol 172: 2487-2495.
9. Belnoue E, Voza T, Costa F T, Gruner A C, Mauduit M, et al. (2008) Vaccination with live *Plasmodium yoelii* blood stage parasites under chloroquine cover induces cross-stage immunity against malaria liver stage. J Immunol 181: 8552-8558.
10. Ploemen I, Behet M, Nganou-Makamdop K, van Gemert G J, Bijker E, et al. (2011) Evaluation of immunity against malaria using luciferase-expressing *Plasmodium berghei* parasites. Malar J 10: 350.

11. Roestenberg M, McCall M, Hopman J, Wiersma J, Luty A J, et al. (2009) Protection against a malaria challenge by sporozoite inoculation. N Engl J Med. 361: 468-477.
12. Roestenberg M, Teirlinck A C, McCall M B, Teelen K, Makamdop K N, et al. (2011) Long-term protection against malaria after experimental sporozoite inoculation: an open-label follow-up study. Lancet 377:1770-1776.
13. van Dijk M R, Douradinha B, Franke-Fayard B, Heussler V, van Dooren M W, et al. (2005) Genetically attenuated, P36p-deficient malarial sporozoites induce protective immunity and apoptosis of infected liver cells. Proc Natl Acad Sci USA 102: 12194-12199.
14. Annoura T, Ploemen I H, van Schaijk B C, Sajid M, Vos M W, et al. (2012) Assessing the adequacy of attenuation of genetically modified malaria parasite vaccine candidates. Vaccine 30: 2662-2670.
15. Silvie O, Goetz K, Matuschewski K (2008) A sporozoite asparagine-rich protein controls initiation of *Plasmodium* liver stage development. PLoS Pathog 4: e1000086.
16. Aly A S, Mikolajczak S A, Rivera H S, Carnargo N, Jacobs-Lorena V, et al. (2008) Targeted deletion of SAP1 abolishes the expression of infectivity factors necessary for successful malaria parasite liver infection. Mol Microbiol 69: 152-163.
17. Aly A S, Lindner S E, MacKellar D C, Peng X, Kappe S H (2011) SAP1 is a critical post-transcriptional regulator of infectivity in malaria parasite sporozoite stages. Mol Microbiol 79: 929-939.
18. Janse C J, Ramesar J, Waters A P (2006) High-efficiency transfection and drug selection of genetically transformed blood stages of the rodent malaria parasite *Plasmodium berghei*. Nat Protoc 1: 346-356.
19. Franke-Fayard B, Trueman H, Ramesar J, Mendoza J, van der Keur M, et al. (2004) A *Plasmodium berghei* reference line that constitutively expresses GFP at a high level throughout the complete life cycle. Mol Biochem Parasitol 137: 23-33.
20. Janse C J, Franke-Fayard B, Mair G R, Ramesar J, Thiel C, et al. (2006) High efficiency transfection of *Plasmodium berghei* facilitates novel selection procedures. Mol Biochem Parasitol 145: 60-70.
21. Sinden R E (1997) Infection of mosquitoes with rodent malaria. 67-91.
22. Yoshida N, Nussenzweig R S, Potoenjak P, Nussenzweig V, Aikawa M (1980) Hybridoma produces protective antibodies directed against the sporozoite stage of malaria parasite. Science 207: 71-73.
23. Mota M M, Pradel G, Vanderberg J P, Hafalla J C, Frevert U, et al. (2001) Migration of *Plasmodium* sporozoites through cells before infection. Science 291: 141-144.
24. Sturm A, Amino R, van de Sand C, Regen T, Retzlaff S, et al. (2006) Manipulation of host hepatocytes by the malaria parasite for delivery into liver sinusoids. Science 313: 1287-1290.
25. Ploemen I H, Prudencio M, Douradinha B G, Ramesar J, Fonager J, et al. (2009) Visualisation and quantitative analysis of the rodent malaria liver stage by real time imaging. PLoS One 4: e7881.
26. Watarai H, Nakagawa R, Omori-Miyake M, Dashtsoodol N, Taniguchi M (2008) Methods for detection, isolation and culture of mouse and human invariant NKT cells. Nat Protoc 3: 70-78.
27. Douradinha B, van Dijk M R, Ataide R, van Gemert G J, Thompson J, et al. (2007) Genetically attenuated P36p-deficient *Plasmodium berghei* sporozoites confer long-lasting and partial cross-species protection. Int J Parasitol 37: 1511-1519.
28. Labaied M, Harupa A, Dumpit R F, Coppens I, Mikolajczak S A, et al. (2007) *Plasmodium yoelii* sporozoites with simultaneous deletion of P52 and P36 are completely attenuated and confer sterile immunity against infection. Infect Immun 75: 3758-3768.
29. Gomes-Santos C S, Braks J, Prudencio M, Carret C, Gomes A R, et al. (2011) Transition of *Plasmodium* sporozoites into liver stage-like forms is regulated by the RNA binding protein Pumilio. PLoS Pathog 7: e1002046.
30. Ponnudurai, T., Leeuwenberg A. D., and Meuwissen, J. H. (1981). Chloroquine sensitivity of isolates of *Plasmodium falciparum* adapted to in vitro culture. Tropical and geographical medicine 33, 50-54.
31. Ifediba, T., and Vanderberg, J. P. (1981). Complete in vitro maturation of *Plasmodium falciparum* gametocytes. Nature 294, 364-366.
32. Ponnudurai, T., Lensen, A. H., Leeuwenberg, A. D., and Meuwissen, J. H. (1982). Cultivation of fertile *Plasmodium falciparum* gametocytes in semi-automated systems. 1. Static cultures. Trans R Soc Trop Med Hyg 76, 812-818.
33. Ponnudurai, T., Lensen, A. H., Van Gemert, G. J., Bensink, M. P., Bolmer, M., and Meuwissen, J. H. (1989). Infectivity of cultured *Plasmodium falciparum* gametocytes to mosquitoes. Parasitology 98 Pt 2, 165-173.
34. Thaithong, S. (1985). Cloning of Malaria Parasites. In Application of genetic engineering to research on tropical disease pathogens with special reference to Plasmodia, S. Panyim, P. Wilairat, and Y. Yuthavong, eds. (Bangkok), pp. 379-387.
35. van Schaijk, B. C., Vos, M. W., Janse, C. J., Sauerwein, R. W., and Khan, S. M. (2010). Removal of Heterologous Sequences from *Plasmodium falciparum* Mutants Using FLPe-Recombinase. PloS one 5, e15121.
36. van Schaijk, B. C., Janse, C. J., van Gemert, G. J., van Dijk, Gego, A., Franetich, J. F., van de Vegte-Bolmer, M., Yalaoui, S., Silvie, O., Hoffman, S. L., et al. (2008). Gene disruption of *Plasmodium falciparum* p52 results in attenuation of malaria liver stage development in cultured primary human hepatocytes. PloS one 3, e3549, Doi: 10.1371/journal.pone.0003549
37. Stewart, M. J., and Vanderberg, J. P. (1988). Malaria sporozoites leave behind trails of circumsporozoite protein during gliding motility. J Protozool 35, 389-393.
38. Guguen-Guillouzo, C., Campion, Brissot, Glaise, D., Launois. B., Bourel, M., and Guillouzo, A. (1982). High yield preparation of isolated human adult hepatocytes by enzymatic perfusion of the liver. Cell Biol. Int Rep 6, 625-628.
39. Renia, L., Mattei, D., Goma, J., Pied, S., Dubois, P., Miltgen, F., Nussler, A., Matile, H., Menegaux, F., Gentilini, M., et al. (1990). A malaria heat-shock-like determinant expressed on the infected hepatocyte surface is the target of antibody-dependent cell-mediated cytotoxic mechanisms by nonparenchymal liver cells. Eur J Immunol 20, 1445-1449.
40. Meuleman, P., Libbrecht, L., De Vos, R., de Hemptinne, B., Gevaert, K., Vandekerckhove, J., Roskams, T., and Leroux-Roels, G. (2005). Morphological and biochemical characterization of a human liver in a uPA-SCID mouse chimera. Hepatology 41, 847-856.
41. Meuleman, P., Vanlandschoot, P., and Leroux-Roels, G. (2003). A simple and rapid method to determine the zygosity of uPA-transgenic SCID mice. Biochem Biophys Res Commun 308, 375-378.
42. Hermsen, C. C., Telgt, D. S., Linders, E. H., van de Locht, L. A., Eling, W. M., Mensink, E. J., and Sauerwein, R. W. (2001). Detection of *Plasmodium falciparum* malaria parasites in vivo by real-time quantitative PCR. Molecular and biochemical parasitology 118, 247-251.
43. Kappe et al. U.S. Pat. No. 7,122,179
44. Annoura, T., Ploemen, I. H., van Schaijk, B. C., Sajid, M., Vos, M. W., van Gemert, G. J., Chevalley-Maurel, S., Franke-Fayard, B. M., Hermsen, C. C., Gego, A., et al. (2012). Assessing the adequacy of attenuation of genetically modified malaria parasite vaccine candidates. Vaccine.
45. Aly, A. S., Mikolajczak, S. A., Rivera, H. S., Camargo, N., Jacobs-Lorena, V., Labaied, M., Coppens, I., and Kappe, S. H. (2008). Targeted deletion of SAP1 abolishes the expression of infectivity factors necessary for successful malaria parasite liver infection. Mol Microbiol 69, 152-163.
46. Silvie, O., Goetz, K., and Matuschewski, K. (2008). A sporozoite asparagine-rich protein controls initiation of *Plasmodium* liver stage development. PLoS pathogens 4, e1000086.
47. Epstein, J E, et al. (2011). Live Attenuated Malaria Vaccine Designed to Protect through Hepatic CD8+ T Cell Immunity. Science 334:475-480.
48. Purcell, L A et al (2008). Chemical Attenuation of *Plasmodium berghei* Sporozoites Induces Sterile Immunity in Mice. Infect. and Immun. 76:1193-1199.
49. Seder, R A, et al (2013). Protection Against Malaria by Intravenous Immunization with a Nonreplicating Sporozoite Vaccine. Science 341:1359-1365.
50. Spring, M et al (2013). First-in-human Evaluation of Genetically Attenuated *Plasmodium falciparum* Sporozoites Administered by Bite of Anopheles Mosquitoes to Adult Volunteers. Vaccine 31:4975-4983.
51. Gerloff D L, Creasey A, Maslau S, Carter R (2005) Structural models for the protein family characterized by gamete surface protein Pfs230 of *Plasmodium falciparum*. Proc Natl Acad Sci USA 102: 13598-13603. 0502378102 [pii]; 10.1073/pnas.0502378102 [doi].
52. Thompson J, Janse C J, Waters A P (2001) Comparative genomics in *Plasmodium*: a tool for the identification of genes and functional analysis. Molecular and Biochemical Parasitology 118: 147-154.
53. Arredondo S A, Cai M, Takayama Y, MacDonald N J, Anderson D E, Aravind L, Clore G M, Miller L H (2012) Structure of the *Plasmodium* 6-cysteine s48/45 domain. Proc Natl Acad Sci USA 109: 6692-6697. 1204363109 [pii]; 10.1073/pnas.1204363109 [doi].
54. Carter R, Coulson A, Bhatti S, Taylor B J, Elliott J F (1995) Predicted disulfide-bonded structures for three uniquely related proteins of *Plasmodium falciparum*, Pfs230, Pfs48/45 and Pf12. Mol Biochem Parasitol 71: 203-210. 0166-6851(94)00054-Q [pii].
55. Ecker, A., Bushell, E. S., Tewari, R., Sinden, R. E. (2008) Reverse genetics screen identifies six proteins important for malaria development in the mosquito. Mol. Microbiol. 70.209-220
56. Provinciali, M et al (1992) Optimization of cytotoxic assay by target cell retention of the fluorescent dye carboxyflurorescein diacetate (CFDA) and comparison with conventional $^{51}$CR release assay. J. Immunol. Meth. 155: 19-24.
57. Sajid M, McKerrow J H, Hansell E, Mathieu M A, Lucas K D, Hsieh I, Greenbaum D, Bogyo M, Salter J P, Lim K C, Franklin C, Kim J H, Caffrey C R (2003) Functional expression and characterization of *Schistosoma mansoni* cathepsin B and its trans-activation by an endogenous asparaginyl endopeptidase. Mol Biochem Parasitol 131: 65-75. S0166685103001944 [pii].
58. Vollenweider et al. (1992) J. Immunol. Meth. 149: 133-135.
59. Ploemen, I H J et al. (2012) *Plasmodium berghei* Δp52 & p36 Parasites Develop Independent of a Parasitophorous Vacuole Membrane in Huh-7 Liver Cells. PLoS ONE 7(12): e50772.
60. VanBuskirk, K. M., O'Neill, M. T., De, L., V, Maier, A. G., Krzych, U., Williams, J., Dowler, M. G., Sacci, J. B., Jr., Kangwanrangsan, N., Tsuboi, T., Kneteman, N. M., Heppner, D. G., Jr., Murdock, B. A., Mikolajczak, S. A., Aly, A. S., Cowman, A. F., Kappe, S. H. (2009) Preerythrocytic, live-attenuated *Plasmodium falciparum* vaccine candidates by design. Proc. Natl. Acad. Sci. U.S.A 106, 13004-13009.
61. van Dijk M R, van Schaijk B C, Khan S M, van Dooren M W, Ramesar J, Kaczanowski S, van Gemert G J, Kroeze H, Stunnenberg H G, Eling W M, Sauerwein R W, Waters A P, Janse C J (2010) Three members of the 6-cys protein family of *Plasmodium* play a role in gamete fertility. PLoS Pathog 6: e1000853. 10.1371/journal.ppat.1000853 [doi].
62. Tonkin, M. L., Arredondo, S. A., Loveless, B. C., Serpa, J. J., Makepeace, K. A., Sundar, N., Petrotchenko, E. V., Miller, L. H., Grigg, M. E., Boulanger, M. J. (2013) Structural and Biochemical Characterization of *Plasmodium falciparum* 12 (Pf12) Reveals a Unique Interdomain Organization and the Potential for an Antiparallel Arrangement with Pf41. J. Biol. Chem. 288, 12805-12817.
63. Helm, S., Lehmann, C., Nagel, A., Stanway, R. R., Horstmann, S., Llinas, M., Heussler, V. T. (2010) Identification and characterization of a liver stage-specific promoter region of the malaria parasite *Plasmodium*. PLoS. One. 5, e13653.
64. Orito, Y., Ishino, T., Iwanaga, S., Kaneko, I., Kato, T., Menard, R., Chinzei, Y., Yuda, M. (2013) Liver-specific protein 2: a *Plasmodium* protein exported to the hepatocyte cytoplasm and required for merozoite formation. Mol. Microbiol. 87, 66-79.
65. Lin, J. W., Annoura, T., Sajid, M., Chevalley-Maurel, S., Ramesar, J., Klop, O., Franke-Fayard, B. M., Janse, C. J., Khan, S. M. (2011) A novel 'gene insertion/marker out' (GIMO) method for transgene expression and gene complementation in rodent malaria parasites. PLoS. One. 6, e29289.
66. Loeffler et al (1992) Analysis of distribution of tumor- and preneoplasia-infiltrating lymphocytes using simultaneous Hoechst 33342 labeling and immunophenotyping. Cytom. 13: 169-174.
67. Rivoltini et al. (1992) Phenotyping and functional analysis of lymphocytes infiltrating paediatric tumours with a characterization of the tumour phenotype. Cancer Immunol. Immunother. 34: 241-251.
68. Chang et al. (1993) Clinical observations on adoptive immunotherapy with vaccine-primed T-lymphocytes secondarily sensitized to tumor in vitro. Cancer Res. 53: 1043-1050.
69. Lootens, L, et al (2009) The uPA(+/+)-SCID mouse with Humanized liver as a model for in Vivo metabolism of 4-Androstene-3,17-dione. Drug Metabolism and Disposition 37(12): 2367-2374.

What is claimed is:

1. A mutant *Plasmodium*-species organism genetically engineered to disrupt the functions of a first gene and a second gene, wherein said first gene is a *Plasmodium* 6-Cys gene selected from the group consisting of b9 and lisp2, and expression of said second gene is essential for passage of a wild type of said *Plasmodium*-species organism through the liver stage and into the blood stage of development of said *Plasmodium*-species organism; wherein said mutant *Plasmodium*-species organism can infect a host subject and invade host hepatocytes of said subject but said mutant organism developmentally arrests during liver stage and does not enter blood stage.

2. The mutant *Plasmodium*-species organism of claim 1 wherein said first gene is b9.

3. The mutant *Plasmodium*-species organism of claim 2 wherein said second gene is selected from the group consisting of slarp, lisp1, lisp2, lsa1, and lsa3.

4. The mutant *Plasmodium*-species organism of claim 3 wherein said second gene is slarp.

5. The mutant *Plasmodium*-species organism of claim 1 wherein the species is selected from the group consisting of *P. falciparum, P. vivax, P. ovale, P. malariae* and *P. knowlesi.*

6. The mutant *Plasmodium*-species organism of claim 5 wherein the species is *P. falciparum.*

7. A method of generating protection from malaria caused by a *Plasmodium*-species parasite of human host range, said method comprising administering to one or more human subjects a pharmaceutical composition comprising the mutant *Plasmodium*-species organism of claim 1, wherein the first gene is b9 and the second gene is slarp, wherein upon subsequent exposure of said human subject to pathogenic *Plasmodium*-species parasites adequate to cause malaria in a human, one or more human subjects are protected from said malaria.

8. The method of claim 7 wherein said administration is subcutaneous, intradermal, intramuscular or intravenous.

9. The method of claim 8 wherein said administration is intravenous.

10. The method of claim 7 comprising a dosage of 50,000 to 2,000,000 of the mutant *Plasmodium*-species organism.

11. A genetically attenuated *Plasmodium*-species parasite (GAP) comprising one or more mutations disrupting the function of a first gene and one or more mutations disrupting the function of a second gene, wherein said first gene is a *Plasmodium* 6-Cys gene selected from the group consisting of b9 and lisp2 and wherein said second gene is essential for passage through the liver stage and into the blood stage of *Plasmodium*-species parasite development of the wild type from which said GAP was derived; wherein said GAP is capable of infecting a host and invading hepatocytes of said host but said GAP developmentally arrests during the liver stage of parasite development and does not enter the blood stage of *Plasmodium*-species parasite development.

12. The GAP of claim 11, wherein said first gene is b9.

13. The GAP of claim 11, wherein said second gene is slarp.

14. The GAP of claim 11, wherein the species of said *Plasmodium* organism is selected from the group consisting of *P. falciparum, P. vivax, P. ovale, P. malariae* and *P. knowlesi.*

* * * * *

SEQUENCE LISTING

<160> NUMBER OF SEQ ID NOS: 104

<210> SEQ ID NO 1
<211> LENGTH: 31
<212> TYPE: DNA
<213> ORGANISM: artificial sequence
<220> FEATURE:
<223> OTHER INFORMATION: delta-b9 5' target F primer

<400> SEQUENCE: 1
ggggtaccta aataacatga tgaaacgtca c                                    31

<210> SEQ ID NO 2
<211> LENGTH: 31
<212> TYPE: DNA
<213> ORGANISM: artificial sequence
<220> FEATURE:
<223> OTHER INFORMATION: delta-b9 5' target R primer

<400> SEQUENCE: 2
cccaagcttt ctatgcatta cttctaccct c                                    31

<210> SEQ ID NO 3
<211> LENGTH: 29
<212> TYPE: DNA
<213> ORGANISM: artificial sequence
<220> FEATURE:
<223> OTHER INFORMATION: delta-b9 3' target F primer

<400> SEQUENCE: 3
ggaattcgat atgcttgaaa ttcctagac                                       29

<210> SEQ ID NO 4
<211> LENGTH: 30
<212> TYPE: DNA
<213> ORGANISM: artificial sequence
<220> FEATURE:
<223> OTHER INFORMATION: delta-b9 3' target R primer

<400> SEQUENCE: 4
tcccccgggg cgcttgtggt tgcatacatc                                      30

<210> SEQ ID NO 5
<211> LENGTH: 21
<212> TYPE: DNA
<213> ORGANISM: artificial sequence
<220> FEATURE:
<223> OTHER INFORMATION: delta-b9 5' integration F primer

<400> SEQUENCE: 5
caaatccaca gacacttact c                                               21

<210> SEQ ID NO 6
<211> LENGTH: 24
<212> TYPE: DNA
<213> ORGANISM: artificial sequence
<220> FEATURE:
<223> OTHER INFORMATION: delta-b9 5' integration R from KO construct
    pL1439 primer

<400> SEQUENCE: 6
atgcacaaaa aaaaatatgc acac                                            24

<210> SEQ ID NO 7
<211> LENGTH: 30
<212> TYPE: DNA

```
<213> ORGANISM: artificial sequence
<220> FEATURE:
<223> OTHER INFORMATION: delta-b9 3' integration F from KO construct
      pL1439 primer

<400> SEQUENCE: 7
gattttaaaa atgtttataa tatgattagc                                              30

<210> SEQ ID NO 8
<211> LENGTH: 19
<212> TYPE: DNA
<213> ORGANISM: artificial sequence
<220> FEATURE:
<223> OTHER INFORMATION: delta-b9 3' integration R primer

<400> SEQUENCE: 8
caaccttttg ccttgcatg                                                          19

<210> SEQ ID NO 9
<211> LENGTH: 20
<212> TYPE: DNA
<213> ORGANISM: artificial sequence
<220> FEATURE:
<223> OTHER INFORMATION: delta-b9 orf F primer

<400> SEQUENCE: 9
cgcattattc gaggtagacc                                                         20

<210> SEQ ID NO 10
<211> LENGTH: 21
<212> TYPE: DNA
<213> ORGANISM: artificial sequence
<220> FEATURE:
<223> OTHER INFORMATION: delta-b9 orf R primer

<400> SEQUENCE: 10
acgggtttca cttacatact c                                                       21

<210> SEQ ID NO 11
<211> LENGTH: 20
<212> TYPE: DNA
<213> ORGANISM: artificial sequence
<220> FEATURE:
<223> OTHER INFORMATION: hdhfr F primer

<400> SEQUENCE: 11
gttcgctaaa ctgcatcgtc                                                         20

<210> SEQ ID NO 12
<211> LENGTH: 21
<212> TYPE: DNA
<213> ORGANISM: artificial sequence
<220> FEATURE:
<223> OTHER INFORMATION: yfcu R primer

<400> SEQUENCE: 12
gtttgaggta gcaagtagac g                                                       21

<210> SEQ ID NO 13
<211> LENGTH: 22
<212> TYPE: DNA
<213> ORGANISM: artificial sequence
<220> FEATURE:
<223> OTHER INFORMATION: delta-b9 negative selection 5' target F primer

<400> SEQUENCE: 13
```
atgagcataa atgtgagcat gg                                                    22

<210> SEQ ID NO 14
<211> LENGTH: 22
<212> TYPE: DNA
<213> ORGANISM: artificial sequence
<220> FEATURE:
<223> OTHER INFORMATION: delta-b9 negative selection 3' target R primer

<400> SEQUENCE: 14
cttgaaccta gattgggtgt ag                                                    22

<210> SEQ ID NO 15
<211> LENGTH: 51
<212> TYPE: DNA
<213> ORGANISM: artificial sequence
<220> FEATURE:
<223> OTHER INFORMATION: delta-b9 5' target F primer

<400> SEQUENCE: 15
gaactcgtac tccttggtga cgggtaccta aataacatga tgaaacgtca c                    51

<210> SEQ ID NO 16
<211> LENGTH: 45
<212> TYPE: DNA
<213> ORGANISM: artificial sequence
<220> FEATURE:
<223> OTHER INFORMATION: delta-b9 5' target R primer

<400> SEQUENCE: 16
catctacaag catcgtcgac ctctctatgc attacttcta ccctc                           45

<210> SEQ ID NO 17
<211> LENGTH: 44
<212> TYPE: DNA
<213> ORGANISM: artificial sequence
<220> FEATURE:
<223> OTHER INFORMATION: delta-b9 3' target F primer

<400> SEQUENCE: 17
ccttcaattt cggatccact aggatatgct tgaaattcct agac                            44

<210> SEQ ID NO 18
<211> LENGTH: 48
<212> TYPE: DNA
<213> ORGANISM: artificial sequence
<220> FEATURE:
<223> OTHER INFORMATION: delta-b9 3' target R primer

<400> SEQUENCE: 18
aggttggtca ttgacactca gcagtactcg cttgtggttg catacatc                        48

<210> SEQ ID NO 19
<211> LENGTH: 22
<212> TYPE: DNA
<213> ORGANISM: artificial sequence
<220> FEATURE:
<223> OTHER INFORMATION: primer for 2nd PCR

<400> SEQUENCE: 19
gaactcgtac tccttggtga cg                                                    22

<210> SEQ ID NO 20
<211> LENGTH: 22
<212> TYPE: DNA
<213> ORGANISM: artificial sequence

```
<220> FEATURE:
<223> OTHER INFORMATION: primer for 2nd PCR

<400> SEQUENCE: 20
aggttggtca ttgacactca gc                                               22

<210> SEQ ID NO 21
<211> LENGTH: 21
<212> TYPE: DNA
<213> ORGANISM: artificial sequence
<220> FEATURE:
<223> OTHER INFORMATION: delta-b9 5' integration F primer

<400> SEQUENCE: 21
caaatccaca gacacttact c                                                21

<210> SEQ ID NO 22
<211> LENGTH: 23
<212> TYPE: DNA
<213> ORGANISM: artificial sequence
<220> FEATURE:
<223> OTHER INFORMATION: delta-b9 5' integration R from KO construct
      pL1499 primer

<400> SEQUENCE: 22
catctacaag catcgtcgac ctc                                              23

<210> SEQ ID NO 23
<211> LENGTH: 22
<212> TYPE: DNA
<213> ORGANISM: artificial sequence
<220> FEATURE:
<223> OTHER INFORMATION: delta-b9 3' integration F from KO construct
      pL1499 primer

<400> SEQUENCE: 23
ccttcaattt cggatccact ag                                               22

<210> SEQ ID NO 24
<211> LENGTH: 19
<212> TYPE: DNA
<213> ORGANISM: artificial sequence
<220> FEATURE:
<223> OTHER INFORMATION: delta-b9 3' integration R primer

<400> SEQUENCE: 24 caacctttg ccttgcatg                                                    19

<210> SEQ ID NO 25
<211> LENGTH: 20
<212> TYPE: DNA
<213> ORGANISM: artificial sequence
<220> FEATURE:
<223> OTHER INFORMATION: delta-b9 orf F primer

<400> SEQUENCE: 25
cgcattattc gaggtagacc                                                  20

<210> SEQ ID NO 26
<211> LENGTH: 21
<212> TYPE: DNA
<213> ORGANISM: artificial sequence
<220> FEATURE:
<223> OTHER INFORMATION: delta-b9 orf R primer

<400> SEQUENCE: 26
```
acgggtttca cttacatact c                                        21

<210> SEQ ID NO 27
<211> LENGTH: 20
<212> TYPE: DNA
<213> ORGANISM: artificial sequence
<220> FEATURE:
<223> OTHER INFORMATION: hdhfr F primer

<400> SEQUENCE: 27
gcttaattct tttcgagctc                                          20

<210> SEQ ID NO 28
<211> LENGTH: 21
<212> TYPE: DNA
<213> ORGANISM: artificial sequence
<220> FEATURE:
<223> OTHER INFORMATION: hdhfr R primer

<400> SEQUENCE: 28
gtgtcacttt caaagtcttg c                                        21

<210> SEQ ID NO 29
<211> LENGTH: 21
<212> TYPE: DNA
<213> ORGANISM: artificial sequence
<220> FEATURE:
<223> OTHER INFORMATION: CS for RT primer

<400> SEQUENCE: 29
ataccagaac cacatgttac g                                        21

<210> SEQ ID NO 30
<211> LENGTH: 21
<212> TYPE: DNA
<213> ORGANISM: artificial sequence
<220> FEATURE:
<223> OTHER INFORMATION: CS F for RT-PCT primer

<400> SEQUENCE: 30
ctctacttcc aggatatgga c                                        21

<210> SEQ ID NO 31
<211> LENGTH: 21
<212> TYPE: DNA
<213> ORGANISM: artificial sequence
<220> FEATURE:
<223> OTHER INFORMATION: CS R for RT-PCR primer

<400> SEQUENCE: 31
cattgagacc attcctctgt g                                        21

<210> SEQ ID NO 32
<211> LENGTH: 22
<212> TYPE: DNA
<213> ORGANISM: artificial sequence
<220> FEATURE:
<223> OTHER INFORMATION: b9 for RT primer

<400> SEQUENCE: 32
ccattctggg tagaacaaat gc                                       22

<210> SEQ ID NO 33
<211> LENGTH: 21
<212> TYPE: DNA
<213> ORGANISM: artificial sequence
<220> FEATURE:
<223> OTHER INFORMATION: b9 F for RT-PCT primer

<400> SEQUENCE: 33
tatcccatca ctcataccta g                                            21

<210> SEQ ID NO 34
<211> LENGTH: 21
<212> TYPE: DNA
<213> ORGANISM: artificial sequence
<220> FEATURE:
<223> OTHER INFORMATION: b9 R for RT-PCR primer

<400> SEQUENCE: 34
acgggtttca cttacatact c                                            21

<210> SEQ ID NO 35
<211> LENGTH: 48
<212> TYPE: DNA
<213> ORGANISM: artificial sequence
<220> FEATURE:
<223> OTHER INFORMATION: delta-slarp 5' target F primer

<400> SEQUENCE: 35
gaactcgtac tccttggtga cgggtaccgg gagtcaaaaa cggtatgc                48

<210> SEQ ID NO 36
<211> LENGTH: 43
<212> TYPE: DNA
<213> ORGANISM: artificial sequence
<220> FEATURE:
<223> OTHER INFORMATION: delta-slarp 5' target R primer

<400> SEQUENCE: 36
catctacaag catcgtcgac ctctcctata gtacatgccc acg                    43

<210> SEQ ID NO 37
<211> LENGTH: 42
<212> TYPE: DNA
<213> ORGANISM: artificial sequence
<220> FEATURE:
<223> OTHER INFORMATION: delta-slarp 3' target F primer

<400> SEQUENCE: 37
ccttcaattt cggatccact agcatgttag gagcacgaaa cc                     42

<210> SEQ ID NO 38
<211> LENGTH: 51
<212> TYPE: DNA
<213> ORGANISM: artificial sequence
<220> FEATURE:
<223> OTHER INFORMATION: delta-slarp 3' target R primer

<400> SEQUENCE: 38
aggttggtca ttgacactca gcagtactct aaaattgtgg gaatccactt g            51

<210> SEQ ID NO 39
<211> LENGTH: 22
<212> TYPE: DNA
<213> ORGANISM: artificial sequence
<220> FEATURE:
<223> OTHER INFORMATION: primer for 2nd PCR

<400> SEQUENCE: 39
gaactcgtac tccttggtga cg                                           22

-continued

<210> SEQ ID NO 40
<211> LENGTH: 22
<212> TYPE: DNA
<213> ORGANISM: artificial sequence
<220> FEATURE:
<223> OTHER INFORMATION: primer for 2nd PCR

<400> SEQUENCE: 40
aggttggtca ttgacactca gc                                              22

<210> SEQ ID NO 41
<211> LENGTH: 20
<212> TYPE: DNA
<213> ORGANISM: artificial sequence
<220> FEATURE:
<223> OTHER INFORMATION: delta-slarp 5' integration F primer

<400> SEQUENCE: 41
catgtctctt tgcatgtggc                                                 20

<210> SEQ ID NO 42
<211> LENGTH: 20
<212> TYPE: DNA
<213> ORGANISM: artificial sequence
<220> FEATURE:
<223> OTHER INFORMATION: delta-slarp 5' integration R from KO construct
      primer

<400> SEQUENCE: 42
ctcatctaca agcatcgtcg                                                 20

<210> SEQ ID NO 43
<211> LENGTH: 22
<212> TYPE: DNA
<213> ORGANISM: artificial sequence
<220> FEATURE:
<223> OTHER INFORMATION: delta-slarp 3' integration F from KO construct
      primer

<400> SEQUENCE: 43
ccttcaattt cggatccact ag                                              22

<210> SEQ ID NO 44
<211> LENGTH: 22
<212> TYPE: DNA
<213> ORGANISM: artificial sequence
<220> FEATURE:
<223> OTHER INFORMATION: delta-slarp 3' integration R primer

<400> SEQUENCE: 44
gtcgtcctat agtaagttga gc                                              22

<210> SEQ ID NO 45
<211> LENGTH: 20
<212> TYPE: DNA
<213> ORGANISM: artificial sequence
<220> FEATURE:
<223> OTHER INFORMATION: slarp orf F primer

<400> SEQUENCE: 45
cccaaatgat caagcaccag                                                 20

<210> SEQ ID NO 46
<211> LENGTH: 21
<212> TYPE: DNA
<213> ORGANISM: artificial sequence

```
<220> FEATURE:
<223> OTHER INFORMATION: slarp orf R primer

<400> SEQUENCE: 46
caatttgaat cggcacaagg c                                              21

<210> SEQ ID NO 47
<211> LENGTH: 20
<212> TYPE: DNA
<213> ORGANISM: artificial sequence
<220> FEATURE:
<223> OTHER INFORMATION: hdhfr-yfcu F primer

<400> SEQUENCE: 47
tggacattgc ctatgaggag                                                20

<210> SEQ ID NO 48
<211> LENGTH: 21
<212> TYPE: DNA
<213> ORGANISM: artificial sequence
<220> FEATURE:
<223> OTHER INFORMATION: hdhfr-yfcu R primer

<400> SEQUENCE: 48
aacacagtag tatctgtcac c                                              21

<210> SEQ ID NO 49
<211> LENGTH: 20
<212> TYPE: DNA
<213> ORGANISM: artificial sequence
<220> FEATURE:
<223> OTHER INFORMATION: b9 orf F primer

<400> SEQUENCE: 49
cgcattattc gaggtagacc                                                20

<210> SEQ ID NO 50
<211> LENGTH: 21
<212> TYPE: DNA
<213> ORGANISM: artificial sequence
<220> FEATURE:
<223> OTHER INFORMATION: b9 orf R primer

<400> SEQUENCE: 50
acgggtttca cttacatact c                                              21

<210> SEQ ID NO 51
<211> LENGTH: 48
<212> TYPE: PRT
<213> ORGANISM: Artificial Sequence
<220> FEATURE:
<223> OTHER INFORMATION: P12p primer

<400> SEQUENCE: 51

Met Met Ser Ile Tyr Phe Trp Val Ala Ile His Ile Phe Ser Ser Phe
1               5                   10                  15

Trp Met Ile Gln Asn Ile Glu Ile Cys Asp Phe Ser Arg Gly Ser Leu
            20                  25                  30

Asp Val Ala Leu Met Asn Asn Lys Ile Leu Ile Asp Asn Asn Leu Lys
        35                  40                  45

<210> SEQ ID NO 52
<211> LENGTH: 48
<212> TYPE: PRT
<213> ORGANISM: Artificial Sequence
```

<220> FEATURE:
<223> OTHER INFORMATION: P230p primer

<400> SEQUENCE: 52

Met Gly Lys Lys Ile Leu Phe Tyr Phe Thr Tyr Gly Ile Phe
1               5                   10                  15

Ile Leu Ile Leu Ile Asn Tyr Glu Tyr Ala Asn Asn Leu Val Lys Lys
            20                  25                  30

Lys Phe Gln Lys Lys Asp Gly Glu Asn Ile Lys Arg Asn Glu Glu Pro
        35                  40                  45

<210> SEQ ID NO 53
<211> LENGTH: 48
<212> TYPE: PRT
<213> ORGANISM: Artificial Sequence
<220> FEATURE:
<223> OTHER INFORMATION: P230 primer

<400> SEQUENCE: 53

Met Arg Lys Pro Ile Leu Ile Val Tyr Leu Phe Phe Ser Tyr Phe Phe
1               5                   10                  15

Leu Tyr Ile Phe Ala Lys Lys Asn Asp Ile Asn Tyr Gly Asp Ile Gly
            20                  25                  30

Ile Glu Gln Pro Tyr Cys Ser Phe Met Phe Leu Glu Lys Asn Ile Leu
        35                  40                  45

<210> SEQ ID NO 54
<211> LENGTH: 48
<212> TYPE: PRT
<213> ORGANISM: Artificial Sequence
<220> FEATURE:
<223> OTHER INFORMATION: B9 primer

<400> SEQUENCE: 54

Met Ser Glu Ser Lys Lys Tyr Lys Trp Asn Pro Val Arg Cys Leu Val
1               5                   10                  15

Cys Trp Ile Met Leu Tyr Leu Ile Leu Trp Thr Asn Phe Leu Asp Gly
            20                  25                  30

Leu Asn Lys Phe Asn Pro Ile Ile Lys Glu Glu Gly Tyr Leu Tyr Leu
        35                  40                  45

<210> SEQ ID NO 55
<211> LENGTH: 48
<212> TYPE: PRT
<213> ORGANISM: Artificial Sequence
<220> FEATURE:
<223> OTHER INFORMATION: conserved Plasmodium protein primer, unknown
       function

<400> SEQUENCE: 55

Met Glu Ile Ile Ile Ala Ile Val Leu Leu Phe Leu Ile Lys Leu Ile
1               5                   10                  15

Tyr Cys Asn Asn His Asn Glu Tyr Ile Ser Tyr Asp Lys Thr Tyr Glu
            20                  25                  30

Tyr Leu Val Asp Ile Ser Lys Asn Asn Asn Arg Leu Ile Cys Val Glu
        35                  40                  45

<210> SEQ ID NO 56
<211> LENGTH: 48
<212> TYPE: PRT
<213> ORGANISM: Artificial Sequence
<220> FEATURE:
<223> OTHER INFORMATION: P36 primer

<400> SEQUENCE: 56

Met Lys Gln Tyr Glu Phe Ala Arg His Ile Asn Thr Tyr Phe Ser Val
1               5                   10                  15

Ala Gln Asn Met Leu Phe Ser Ile Phe Leu Tyr Tyr Ala Phe Ser Leu
            20                  25                  30

Leu Ile Phe Leu Ser Ile Phe Val Phe Lys Met Arg Lys Ala Leu Tyr
        35                  40                  45

<210> SEQ ID NO 57
<211> LENGTH: 48
<212> TYPE: PRT
<213> ORGANISM: Artificial Sequence
<220> FEATURE:
<223> OTHER INFORMATION: p52(p36p) primer

<400> SEQUENCE: 57

Met Met Lys Arg Arg Arg Ile Phe Met Tyr Tyr Cys Phe Cys Phe Leu
1               5                   10                  15

Leu Lys Tyr Val Ala Phe Ser Asn Val Thr Asn Pro Asn Thr Thr Leu
            20                  25                  30

Gly His Phe Glu Ile Cys Lys Ile Asn Ile Tyr Ser Gly Asp Ala Glu
        35                  40                  45

<210> SEQ ID NO 58
<211> LENGTH: 48
<212> TYPE: PRT
<213> ORGANISM: Artificial Sequence
<220> FEATURE:
<223> OTHER INFORMATION: P41 primer

<400> SEQUENCE: 58

Met Lys Gly Leu Leu Ile Tyr Thr Phe Ile Phe Leu Leu Lys Gln Leu
1               5                   10                  15

Ser Val Arg Ser Glu Glu Tyr Val Cys Asp Phe Arg Ala Lys Asn Tyr
            20                  25                  30

Leu Tyr Asp Asn Lys Asp Ile Leu Tyr Cys Thr Ile Asn Ala Lys Pro
        35                  40                  45

<210> SEQ ID NO 59
<211> LENGTH: 48
<212> TYPE: PRT
<213> ORGANISM: Artificial Sequence
<220> FEATURE:
<223> OTHER INFORMATION: Seq primer

<400> SEQUENCE: 59

Met Lys Asp His Ile Lys Asn Val Cys Phe Arg Lys Thr Leu Leu Ile
1               5                   10                  15

Ser Leu Leu Leu Ile Ile Leu Lys Tyr Thr Lys Tyr Asp Tyr Leu Glu
            20                  25                  30

Lys Glu Asn Asp Glu Lys Gln Lys Tyr Asn Ser Asn Ile Ser Ser Pro
        35                  40                  45

<210> SEQ ID NO 60
<211> LENGTH: 48
<212> TYPE: PRT
<213> ORGANISM: Artificial Sequence
<220> FEATURE:
<223> OTHER INFORMATION: P38 primer

<400> SEQUENCE: 60

Met Ser Lys Met Ile His Val Lys Asn Ile Ile Thr Ser Ile Leu Val
1               5                   10                  15

Ile Val Ile Leu Cys Leu Asn Gly Ile Thr Ser Lys Lys Ser Val Asp
            20                  25                  30

Leu Ala Asn Leu Val Lys Asn Ile Ile Thr Leu Asn Ala Ser Pro Gly
        35                  40                  45

<210> SEQ ID NO 61
<211> LENGTH: 48
<212> TYPE: PRT
<213> ORGANISM: Artificial Sequence
<220> FEATURE:
<223> OTHER INFORMATION: PSOP12 primer

<400> SEQUENCE: 61

Met Ser Lys Met Ile His Val Lys Asn Ile Ile Thr Ser Ile Leu Val
1               5                   10                  15

Ile Val Ile Leu Cys Leu Asn Gly Ile Thr Ser Lys Lys Ser Val Asp
            20                  25                  30

Leu Ala Asn Leu Val Lys Asn Ile Ile Thr Leu Asn Ala Ser Pro Gly
        35                  40                  45

<210> SEQ ID NO 62
<211> LENGTH: 48
<212> TYPE: PRT
<213> ORGANISM: Artificial Sequence
<220> FEATURE:
<223> OTHER INFORMATION: conserved Plasmodium protein primer, unknown
      function

<400> SEQUENCE: 62

Met Phe Thr Phe Phe Phe Phe Leu Leu Thr Met Tyr Leu Leu Phe Ala
1               5                   10                  15

Thr Arg Val Val Asn Val Lys Ala Gln Ser Glu Gly Ile Ile Lys Thr
            20                  25                  30

Lys Ser Ile Glu Ile Ser Tyr Asp Glu Asn Ser Arg His Leu Tyr Ile
        35                  40                  45

<210> SEQ ID NO 63
<211> LENGTH: 48
<212> TYPE: PRT
<213> ORGANISM: Artificial Sequence
<220> FEATURE:
<223> OTHER INFORMATION: Oocyst capsule protein (Cap380) primer

<400> SEQUENCE: 63

Met Tyr Val Ile Asn Ile Val Tyr Val Leu Ile Val Cys Leu Leu Gly
1               5                   10                  15

Thr Val Leu Ser Ser Pro Tyr Trp Gly Asp Pro Leu Asn Asp Phe
            20                  25                  30

Gly Asn Glu Glu Leu Asn Thr Asn Lys Lys Lys Arg Leu His Ser Thr
        35                  40                  45

<210> SEQ ID NO 64
<211> LENGTH: 48
<212> TYPE: PRT
<213> ORGANISM: Artificial Sequence
<220> FEATURE:
<223> OTHER INFORMATION: P48/45 primer

<400> SEQUENCE: 64

Met Leu Tyr Phe Phe Gly Asn Ser Arg Phe Phe Leu Phe Phe Phe Tyr
1               5                   10                  15

Phe Phe Phe Tyr Phe Val Leu Val Ile Lys Ser Ser Val Gly Lys Asn
            20                  25                  30

Glu Tyr Val Ser Pro Asp Glu Leu Asn Ile Lys Thr Ser Gly Phe Leu
        35                  40                  45

<210> SEQ ID NO 65
<211> LENGTH: 48
<212> TYPE: PRT
<213> ORGANISM: Artificial Sequence
<220> FEATURE:
<223> OTHER INFORMATION: P47 primer

<400> SEQUENCE: 65

Met Lys Gly Phe Thr Gly Ala Ser Ile Ile Val Phe Tyr Leu Ile Lys
1               5                   10                  15

Gly Tyr Leu Ser Tyr Ile Ile Phe Pro Asn Gly Tyr Val Cys Asp Phe
            20                  25                  30

Lys Phe Asn Pro Leu Val Asn Val Leu Pro Ser Ile Asn Thr Thr Gly
        35                  40                  45

<210> SEQ ID NO 66
<211> LENGTH: 30
<212> TYPE: DNA
<213> ORGANISM: Artificial Sequence
<220> FEATURE:
<223> OTHER INFORMATION: b9 promoter F primer

<400> SEQUENCE: 66
gcgccttaag tttccacata tgtgcaggtg                                    30

<210> SEQ ID NO 67
<211> LENGTH: 38
<212> TYPE: DNA
<213> ORGANISM: Artificial Sequence
<220> FEATURE:
<223> OTHER INFORMATION: b9 promoter R primer

<400> SEQUENCE: 67
cgggatcctt atatatttaa cactattaat ttatctta                           38

<210> SEQ ID NO 68
<211> LENGTH: 51
<212> TYPE: DNA
<213> ORGANISM: Artificial Sequence
<220> FEATURE:
<223> OTHER INFORMATION: b9 3' utr F primer

<400> SEQUENCE: 68
aaggaaaaaa gcggccgcaa attgtaataa tataaaagaa tgagaaattc g            51

<210> SEQ ID NO 69
<211> LENGTH: 51
<212> TYPE: DNA
<213> ORGANISM: Artificial Sequence
<220> FEATURE:
<223> OTHER INFORMATION: b9 3' utr R primer

<400> SEQUENCE: 69
aaggaaaaaa gcggccgcaa attgtaataa tataaaagaa tgagaaattc g            51

<210> SEQ ID NO 70
<211> LENGTH: 29
<212> TYPE: DNA
<213> ORGANISM: Artificial Sequence

```
<220> FEATURE:
<223> OTHER INFORMATION: delta-PBANKA_100300  5' target F primer

<400> SEQUENCE: 70
ggggtaccca acagcaatat atcgtcacc                                              29

<210> SEQ ID NO 71
<211> LENGTH: 31
<212> TYPE: DNA
<213> ORGANISM: Artificial Sequence
<220> FEATURE:
<223> OTHER INFORMATION: delta-PBANKA_100300  5'target R primer

<400> SEQUENCE: 71
cccaagcttc gtgtttcctt tcttttctc g                                            31

<210> SEQ ID NO 72
<211> LENGTH: 30
<212> TYPE: DNA
<213> ORGANISM: Artificial Sequence
<220> FEATURE:
<223> OTHER INFORMATION: delta- PBANKA_100300  3' target F primer

<400> SEQUENCE: 72
ggaattcgaa gaaaacaata aagagctacc                                             30

<210> SEQ ID NO 73
<211> LENGTH: 29
<212> TYPE: DNA
<213> ORGANISM: Artificial Sequence
<220> FEATURE:
<223> OTHER INFORMATION: delta-PBANKA_100300  3' target R primer

<400> SEQUENCE: 73
cgggatcccg atatcgacgt agcttaccg                                              29

<210> SEQ ID NO 74
<211> LENGTH: 22
<212> TYPE: DNA
<213> ORGANISM: Artificial Sequence
<220> FEATURE:
<223> OTHER INFORMATION: delta-PBANKA_100300  5' integration F primer

<400> SEQUENCE: 74
gtatgctttc ggaaaactct ac                                                     22

<210> SEQ ID NO 75
<211> LENGTH: 20
<212> TYPE: DNA
<213> ORGANISM: Artificial Sequence
<220> FEATURE:
<223> OTHER INFORMATION: delta-PBANKA_100300  5' integration R from KO
      construct pL1462 primer

<400> SEQUENCE: 75
attgttgacc tgcaggcatg                                                        20

<210> SEQ ID NO 76
<211> LENGTH: 22
<212> TYPE: DNA
<213> ORGANISM: Artificial Sequence
<220> FEATURE:
<223> OTHER INFORMATION: delta-PBANKA_100300  3' integration F from KO
      construct pL1462 primer

<400> SEQUENCE: 76
```
gattcataaa tagttggact tg                                             22

<210> SEQ ID NO 77
<211> LENGTH: 20
<212> TYPE: DNA
<213> ORGANISM: Artificial Sequence
<220> FEATURE:
<223> OTHER INFORMATION: delta-PBANKA_100300 3' integration R primer

<400> SEQUENCE: 77
gaagaagtat gaccatacgc                                                20

<210> SEQ ID NO 78
<211> LENGTH: 22
<212> TYPE: DNA
<213> ORGANISM: Artificial Sequence
<220> FEATURE:
<223> OTHER INFORMATION: delta-PBANKA_100300 orf F primer

<400> SEQUENCE: 78
atggaatggg aaagagaaag ag                                             22

<210> SEQ ID NO 79
<211> LENGTH: 23
<212> TYPE: DNA
<213> ORGANISM: Artificial Sequence
<220> FEATURE:
<223> OTHER INFORMATION: PBANKA_100300 orf R primer

<400> SEQUENCE: 79
gaaggtcttt taatgttgcc ctc                                            23

<210> SEQ ID NO 80
<211> LENGTH: 20
<212> TYPE: DNA
<213> ORGANISM: Artificial Sequence
<220> FEATURE:
<223> OTHER INFORMATION: tgdhfr/ts-F primer

<400> SEQUENCE: 80
ggacagattg aacatcgtcg                                                20

<210> SEQ ID NO 81
<211> LENGTH: 21
<212> TYPE: DNA
<213> ORGANISM: Artificial Sequence
<220> FEATURE:
<223> OTHER INFORMATION: tgdhfr/ts-R primer

<400> SEQUENCE: 81
gatcacattc ttcagctggt c                                              21

<210> SEQ ID NO 82
<211> LENGTH: 31
<212> TYPE: DNA
<213> ORGANISM: Artificial Sequence
<220> FEATURE:
<223> OTHER INFORMATION: delta-Pyb9 5' target F primer

<400> SEQUENCE: 82
catgggcccT TCCACATGT atgtgcaggt g                                    31

<210> SEQ ID NO 83
<211> LENGTH: 32
<212> TYPE: DNA
<213> ORGANISM: Artificial Sequence -continued
<220> FEATURE:
<223> OTHER INFORMATION: delta-Pyb9  5'target R primer

<400> SEQUENCE: 83
gcgccttaag aacaagtcat aaccacgttc tg                                    32

<210> SEQ ID NO 84
<211> LENGTH: 36
<212> TYPE: DNA
<213> ORGANISM: Artificial Sequence
<220> FEATURE:
<223> OTHER INFORMATION: delta-Pyb9 3' target F primer

<400> SEQUENCE: 84
atagtttagc ggccgcggac caagtaatga acccg                                 36

<210> SEQ ID NO 85
<211> LENGTH: 31
<212> TYPE: DNA
<213> ORGANISM: Artificial Sequence
<220> FEATURE:
<223> OTHER INFORMATION: delta-Pyb9  3' target R primer

<400> SEQUENCE: 85
ggaattctgc aaataatgtc gcatttaaga g                                     31

<210> SEQ ID NO 86
<211> LENGTH: 20
<212> TYPE: DNA
<213> ORGANISM: Artificial Sequence
<220> FEATURE:
<223> OTHER INFORMATION: Pyb9 5' integration F primer

<400> SEQUENCE: 86
aaagcccgag gcaaacaaac                                                  20

<210> SEQ ID NO 87
<211> LENGTH: 24
<212> TYPE: DNA
<213> ORGANISM: Artificial Sequence
<220> FEATURE:
<223> OTHER INFORMATION: Pyb9 5' integration R from KO construct primer

<400> SEQUENCE: 87
atgcacaaaa aaaatatgc acac                                              24

<210> SEQ ID NO 88
<211> LENGTH: 30
<212> TYPE: DNA
<213> ORGANISM: Artificial Sequence
<220> FEATURE:
<223> OTHER INFORMATION: delta-Pyb9  3' integration F from KO construct
     primer

<400> SEQUENCE: 88
gatttttaaa atgtttataa tatgattagc                                       30

<210> SEQ ID NO 89
<211> LENGTH: 22
<212> TYPE: DNA
<213> ORGANISM: Artificial Sequence
<220> FEATURE:
<223> OTHER INFORMATION: delta-Pyb9  3' integration R primer

<400> SEQUENCE: 89
gcttgtgatt gcatacatcg tg                                               22

```
<210> SEQ ID NO 90
<211> LENGTH: 23
<212> TYPE: DNA
<213> ORGANISM: Artificial Sequence
<220> FEATURE:
<223> OTHER INFORMATION: delta-Pyb9 orf F primer

<400> SEQUENCE: 90
ccgttaagtg tctagtatgg ttg                                              23

<210> SEQ ID NO 91
<211> LENGTH: 20
<212> TYPE: DNA
<213> ORGANISM: Artificial Sequence
<220> FEATURE:
<223> OTHER INFORMATION: delta-Pyb9 orf R primer

<400> SEQUENCE: 91
cctcgaacaa tgcgtagtac                                                  20

<210> SEQ ID NO 92
<211> LENGTH: 20
<212> TYPE: DNA
<213> ORGANISM: Artificial Sequence
<220> FEATURE:
<223> OTHER INFORMATION: hdhfr F primer

<400> SEQUENCE: 92
gttcgctaaa ctgcatcgtc                                                  20

<210> SEQ ID NO 93
<211> LENGTH: 21
<212> TYPE: DNA
<213> ORGANISM: Artificial Sequence
<220> FEATURE:
<223> OTHER INFORMATION: yfcu R primer

<400> SEQUENCE: 93
gtttgaggta gcaagtagac g                                                21

<210> SEQ ID NO 94
<211> LENGTH: 35
<212> TYPE: DNA
<213> ORGANISM: Artificial Sequence
<220> FEATURE:
<223> OTHER INFORMATION: Pf delta-b9  5' target F primer

<400> SEQUENCE: 94
ctaccatggt atgggagctt gggcataatg tcatg                                 35

<210> SEQ ID NO 95
<211> LENGTH: 34
<212> TYPE: DNA
<213> ORGANISM: Artificial Sequence
<220> FEATURE:
<223> OTHER INFORMATION: Pf delta-b9  5'target R primer

<400> SEQUENCE: 95
gtacccgggc gtgtcttatc atattcacaa aggc                                  34

<210> SEQ ID NO 96
<211> LENGTH: 33
<212> TYPE: DNA
<213> ORGANISM: Artificial Sequence
<220> FEATURE:
```

<223> OTHER INFORMATION: Pf delta-b9 3' target F primer

<400> SEQUENCE: 96
catacgcgtc ctatatgatc aatcaccacc tag                                    33

<210> SEQ ID NO 97
<211> LENGTH: 33
<212> TYPE: DNA
<213> ORGANISM: Artificial Sequence
<220> FEATURE:
<223> OTHER INFORMATION: Pf delta-b9 3' target R primer

<400> SEQUENCE: 97
atagcgcgct gtctatcata caaactggca tcc                                    33

<210> SEQ ID NO 98
<211> LENGTH: 22
<212> TYPE: DNA
<213> ORGANISM: Artificial Sequence
<220> FEATURE:
<223> OTHER INFORMATION: LR-PCR primer

<400> SEQUENCE: 98
tcatgggttt ttaaatagcc tc                                                22

<210> SEQ ID NO 99
<211> LENGTH: 25
<212> TYPE: DNA
<213> ORGANISM: Artificial Sequence
<220> FEATURE:
<223> OTHER INFORMATION: LR-PCR primer

<400> SEQUENCE: 99
gatgtacacc tacatttgaa tgaag                                             25

<210> SEQ ID NO 100
<211> LENGTH: 23
<212> TYPE: DNA
<213> ORGANISM: Artificial Sequence
<220> FEATURE:
<223> OTHER INFORMATION: RT-PCR primer

<400> SEQUENCE: 100
tccacatgga tgatatggta tgg                                               23

<210> SEQ ID NO 101
<211> LENGTH: 19
<212> TYPE: DNA
<213> ORGANISM: Artificial Sequence
<220> FEATURE:
<223> OTHER INFORMATION: RT-PCR primer

<400> SEQUENCE: 101
tgttgtgctc actagacgg                                                    19

<210> SEQ ID NO 102
<211> LENGTH: 29
<212> TYPE: DNA
<213> ORGANISM: Artificial Sequence
<220> FEATURE:
<223> OTHER INFORMATION: RT-PCR primer

<400> SEQUENCE: 102
gtaattggaa tgataggaat ttacaaggt                                         29

-continued

```
<210> SEQ ID NO 103
<211> LENGTH: 26
<212> TYPE: DNA
<213> ORGANISM: Artificial Sequence
<220> FEATURE:
<223> OTHER INFORMATION: RT-PCR primer

<400> SEQUENCE: 103
tcaactacga acgttttaac tgcaac                                          26

<210> SEQ ID NO 104
<211> LENGTH: 48
<212> TYPE: PRT
<213> ORGANISM: Artificial Sequence
<220> FEATURE:
<223> OTHER INFORMATION: P12

<400> SEQUENCE: 104

Met Val Gln Ile Lys Lys Asn Ile Leu Ile Tyr Thr Ile Leu Ser Tyr
1               5                   10                  15

Leu Val Tyr Thr Ile Lys Gly Leu Glu His Gln Cys Asp Phe Asn Glu
            20                  25                  30

Asn His Thr Ile Glu Ile Thr Asp Thr Glu Asn His Asp Ile Asp Asn
        35                  40                  45
```